(12) United States Patent
Barbie et al.

(10) Patent No.: US 11,874,276 B2
(45) Date of Patent: Jan. 16, 2024

(54) STING LEVELS AS A BIOMARKER FOR CANCER IMMUNOTHERAPY

(71) Applicants: Dana-Farber Cancer Institute, Inc., Boston, MA (US); The Brigham and Women's Hospital, Inc., Boston, MA (US)

(72) Inventors: David Barbie, Andover, MA (US); Israel Cañadas, Brookline, MA (US); Shunsuke Kitajima, Allston, MA (US); Thanh Barbie, Andover, MA (US)

(73) Assignees: Dana-Farber Cancer Institute, Inc., Boston, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 17/045,148

(22) PCT Filed: Apr. 5, 2019

(86) PCT No.: PCT/US2019/025959
§ 371 (c)(1),
(2) Date: Oct. 2, 2020

(87) PCT Pub. No.: WO2019/195658
PCT Pub. Date: Oct. 10, 2019

(65) Prior Publication Data
US 2021/0025893 A1  Jan. 28, 2021

Related U.S. Application Data

(60) Provisional application No. 62/653,223, filed on Apr. 5, 2018.

(51) Int. Cl.
| | | |
|---|---|---|
| *G01N 33/574* | (2006.01) | |
| *A61K 38/00* | (2006.01) | |
| *A61K 38/21* | (2006.01) | |
| *A61P 35/00* | (2006.01) | |
| *C07K 14/05* | (2006.01) | |
| *G01N 33/68* | (2006.01) | |
| *C07K 14/57* | (2006.01) | |

(52) U.S. Cl.
CPC ..... *G01N 33/57484* (2013.01); *A61K 38/005* (2013.01); *A61K 38/21* (2013.01); *A61K 38/217* (2013.01); *A61P 35/00* (2018.01); *C07K 14/57* (2013.01); *G01N 33/57423* (2013.01); *G01N 33/6866* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,464,871 A | 11/1995 | Kun et al. | |
| 5,484,951 A | 1/1996 | Kun et al. | |
| 5,595,756 A * | 1/1997 | Bally | A61K 9/1272 264/4.1 |
| 5,670,518 A | 9/1997 | Kun et al. | |
| 5,736,576 A | 4/1998 | Kun et al. | |
| 5,922,775 A | 7/1999 | Kun et al. | |
| 6,004,978 A | 12/1999 | Kun et al. | |
| 6,017,958 A | 1/2000 | Kun et al. | |
| 6,100,283 A | 8/2000 | Griffin et al. | |
| 6,169,104 B1 | 1/2001 | Tuse et al. | |
| 6,310,082 B1 | 10/2001 | Griffin et al. | |
| 8,734,804 B2 | 5/2014 | Marcus | |
| 9,643,922 B2 | 5/2017 | Jorgensen et al. | |
| 10,004,711 B2 | 6/2018 | Weiser et al. | |
| 10,045,961 B2 | 8/2018 | Chang et al. | |
| 10,093,623 B2 | 10/2018 | Heinrich et al. | |
| 10,106,574 B2 | 10/2018 | Altman et al. | |
| 2002/0028815 A1 | 3/2002 | Ator et al. | |
| 2002/0156050 A1 | 10/2002 | Li et al. | |
| 2005/0032839 A1 | 2/2005 | Fancelli et al. | |
| 2005/0054631 A1 | 3/2005 | Jiang et al. | |
| 2005/0256102 A1 | 11/2005 | Claiborne et al. | |
| 2007/0185087 A1 | 8/2007 | Claiborne et al. | |
| 2008/0045501 A1 | 2/2008 | Claiborne et al. | |
| 2008/0167292 A1 | 7/2008 | Claiborne et al. | |
| 2009/0055944 A1 | 2/2009 | Korman et al. | |
| 2010/0203056 A1 | 8/2010 | Irving et al. | |
| 2011/0119776 A1 | 5/2011 | Wong et al. | |
| 2011/0152206 A1 | 6/2011 | Narayan et al. | |

(Continued)

FOREIGN PATENT DOCUMENTS

| | | |
|---|---|---|
| EP | 0841924 A1 | 5/1998 |
| EP | 1127052 A1 | 8/2001 |

(Continued)

OTHER PUBLICATIONS

Waiker et al (J Am Soc Nephrol. Jan. 2012; 23(1): 13-21) (Year: 2012).*
Brooks (Genome Res. Feb. 2012;22(2):183-7) (Year: 2012).*
Skolnick et al (Trends Biotechnol. Jan. 2000;18(1):34-9) (Year: 2000).*
Burgess et al. (J. Cell Biol. 111:2129-2138, 1990) (Year: 1990).*
Lazar et al. (Mol. Cell. Biol., 8:1247-1252, 1988) (Year: 1988).*
Miosge (Proc Natl Acad Sci U S A. Sep. 15, 2015;112(37):E5189-98) (Year: 2015).*
Bork (Genome Research, 2000, 10:398-400) (Year: 2000).*
Guido et al (Curr Med Chem. 2008; 15(1):37-46) (Year: 2008).*

(Continued)

*Primary Examiner* — Brian Gangle
*Assistant Examiner* — Andrea K McCollum
(74) *Attorney, Agent, or Firm* — Wolf, Greenfield & Sacks, P.C.

(57) ABSTRACT

Provided herein are Stimulator of Interferon Genes (STING) and Stimulated 3 Prime Antisense Retroviral Coding Sequences (SPARCS) genes as biomarkers for determining an effective therapy for treating cancer. Further provided are methods for treating cancer using said biomarkers.

17 Claims, 59 Drawing Sheets

Specification includes a Sequence Listing.

(56) References Cited

U.S. PATENT DOCUMENTS

| | | |
|---|---|---|
| 2011/0271358 A1 | 11/2011 | Freeman et al. |
| 2012/0039906 A1 | 2/2012 | Olive et al. |
| 2012/0251537 A1 | 10/2012 | Ahmed et al. |
| 2013/0017199 A1 | 1/2013 | Langermann |
| 2013/0045202 A1 | 2/2013 | Irving et al. |
| 2013/0108651 A1 | 5/2013 | Carven et al. |
| 2013/0109843 A1 | 5/2013 | Carven et al. |
| 2013/0230514 A1 | 9/2013 | Langermann et al. |
| 2013/0237580 A1 | 9/2013 | Sasikumar et al. |
| 2013/0280265 A1 | 10/2013 | Rolland et al. |
| 2013/0309250 A1 | 11/2013 | Cogswell et al. |
| 2014/0034197 A1 | 2/2014 | Sippel et al. |
| 2014/0329889 A1 | 11/2014 | Vance et al. |
| 2015/0056224 A1 | 2/2015 | Dubensky et al. |
| 2016/0108123 A1 | 4/2016 | Freeman et al. |
| 2016/0287623 A1 | 10/2016 | Gajewski et al. |
| 2016/0312294 A1 | 10/2016 | Walker et al. |
| 2016/0331810 A1 | 11/2016 | Slingluff et al. |
| 2017/0158772 A1 | 6/2017 | Thompson et al. |
| 2018/0230115 A1 | 8/2018 | Zhong et al. |
| 2018/0230171 A1 | 8/2018 | Sanchez et al. |
| 2018/0230177 A1 | 8/2018 | Zhong et al. |
| 2019/0031708 A1 | 1/2019 | Glick et al. |
| 2019/0185511 A1 | 6/2019 | Kanne et al. |
| 2022/0305048 A1 | 9/2022 | Shriram et al. |

FOREIGN PATENT DOCUMENTS

| | | | |
|---|---|---|---|
| EP | 1644376 B1 | 4/2006 | |
| EP | 2170959 A1 | 4/2010 | |
| GB | 1501462 A | 2/1978 | |
| WO | WO 1999/011628 A1 | 3/1999 | |
| WO | WO 2000/050032 A1 | 8/2000 | |
| WO | WO 2004/000833 A1 | 12/2003 | |
| WO | WO 2004/043953 A1 | 5/2004 | |
| WO | WO 2004/058781 A1 | 7/2004 | |
| WO | WO 2004/071507 A1 | 8/2004 | |
| WO | WO 2005/002552 A2 | 1/2005 | |
| WO | WO 2005/002576 A2 | 1/2005 | |
| WO | WO 2005/005427 A1 | 1/2005 | |
| WO | WO 2005/012305 A2 | 2/2005 | |
| WO | WO 2005/013996 A2 | 2/2005 | |
| WO | WO 2005/111039 A2 | 11/2005 | |
| WO | WO 2005/118544 A2 | 12/2005 | |
| WO | WO 2006/003440 A1 | 1/2006 | |
| WO | WO 2006/036266 A1 | 4/2006 | |
| WO | WO 2006/055528 A2 | 5/2006 | |
| WO | WO 2006/055561 A2 | 5/2006 | |
| WO | WO 2006/070192 A1 | 7/2006 | |
| WO | WO 2006/070195 A1 | 7/2006 | |
| WO | WO 2006/070198 A1 | 7/2006 | |
| WO | WO 2006/070202 A1 | 7/2006 | |
| WO | WO 2007/056164 A2 | 5/2007 | |
| WO | WO 2007/113212 A2 | 10/2007 | |
| WO | WO 2007/132220 A1 | 11/2007 | |
| WO | WO 2007/132221 A1 | 11/2007 | |
| WO | WO 2007/132228 A1 | 11/2007 | |
| WO | WO 2008/021038 A2 | 2/2008 | |
| WO | WO 2008/063525 A1 | 5/2008 | |
| WO | WO 2013/185052 A1 | 12/2013 | |
| WO | WO 2014/093936 A1 | 6/2014 | |
| WO | WO 2014/189805 A1 | 11/2014 | |
| WO | WO 2015/077354 A1 | 5/2015 | |
| WO | WO 2016/145102 A1 | 9/2016 | |
| WO | WO 2016/201450 A2 | 12/2016 | |
| WO | WO-2016201450 A2 * | 12/2016 | ........... A61K 35/763 |
| WO | WO 2017/011920 A1 | 1/2017 | |
| WO | WO 2017/106656 A1 | 6/2017 | |
| WO | WO 2017/186711 A1 | 11/2017 | |

OTHER PUBLICATIONS

Clark et al (J. Med. Chem., 2014, 57 (12), pp. 5023-5038) (Year: 2014).*

Vajdos et al. (J Mol Biol. Jul. 5, 2002;320(2):415-28 (Year: 2002).*

Brown et al. (J Immunol. May 1996; 156(9):3285-91 (Year: 1996).*

Aagaard et al (Advanced Drug Delivery Reviews 59 (2007) 75-86) (Year: 2007).*

Warzocha et al (Leukemia and Lymphoma (1997) vol. 24. pp. 267-281) (Year: 1997).*

McKeague et al (J Nucleic Acids. 2012;2012:748913. Epub Oct. 24, 2012) (Year: 2012).*

Sporn et al, "Chemoprevention of Cancer," Carcinogenesis, vol. 21 (2000), 525-530 (Year: 2000).*

Auerbach et al (Cancer and Metastasis Reviews, 2000, 19: 167-172) (Year: 2000).*

Gura T (Science, 1997, 278(5340): 1041-1042, encloses 1-5) (Year: 1997).*

Jain RK (Scientific American, Jul. 1994,58-65) (Year: 1994).*

Hogenesch et al (J Control Release. Dec. 10, 2012; 164(2): 183-186.) (Year: 2012).*

Holmes et al ("The Potential of STING Agonists Is Explored in Cancer," Targeted Therapies in Oncology, Mar. 2022; downloaded from https://www.targetedonc.com/view/the-potential-of-sting-agonists-is-explored-in-cancer on Feb. 15, 2023) (Year: 2022).*

International Search Report and Written Opinion for PCT/US2019/025959 dated Jun. 18, 2019.

International Preliminary Report on Patentability for PCT/US2019/025959 dated Oct. 15, 2020.

Bindea et al., Spatiotemporal dynamics of intratumoral immune cells reveal the immune landscape in human cancer. Immunity. Oct. 17, 2013;39(4):782-95. doi: 10.1016/j.immuni.2013.10.003. PMID: 24138885.

Calbo et al., A functional role for tumor cell heterogeneity in a mouse model of small cell lung cancer. Cancer Cell. Feb. 15, 2011;19(2):244-56. doi: 10.1016/j.ccr.2010.12.021.

Cañadas et al., Targeting epithelial-to-mesenchymal transition with Met inhibitors reverts chemoresistance in small cell lung cancer. Clin Cancer Res. Feb. 15, 2014;20(4):938-50. doi: 10.1158/1078-0432.CCR-13-1330. Epub Nov. 27, 2013. PMID: 24284055.

Chen et al., Over 20% of human transcripts might form sense-antisense pairs. Nucleic Acids Res. Sep. 8, 2004;32(16):4812-20. doi: 10.1093/nar/gkh818. PMID: 15356298.

Chiappinelli et al., Inhibiting DNA Methylation Causes an Interferon Response in Cancer via dsRNA Including Endogenous Retroviruses. Cell. Aug. 27, 2015;162(5):974-86. doi: 10.1016/j.cell.2015.07.011. Erratum in: Cell. Feb. 25, 2016;164(5):1073. Buhu, Sadna [corrected to Budhu, Sadna]; Mergoub, Taha [corrected to Merghoub, Taha]. Erratum in: Cell. Apr. 6, 2017;169(2):361. PMID: 26317466; PMCID: PMC4556003.

Christensen et al., Targeting transcriptional addictions in small cell lung cancer with a covalent CDK7 inhibitor. Cancer Cell. Dec. 8, 2014;26(6):909-922. doi: 10.1016/j.ccell.2014.10.019. Erratum in: Cancer Cell. Jan. 12, 2015;27(1):149. PMID: 25490451.

Corrales et al., Innate immune signaling and regulation in cancer immunotherapy. Cell Res. Jan. 2017;27(1):96-108. doi: 10.1038/cr.2016.149. Epub Dec. 16, 2016.

Hanahan et al., Hallmarks of cancer: the next generation. Cell. Mar. 4, 2011;144(5):646-74. doi: 10.1016/j.cell.2011.02.013. PMID: 21376230.

Henke et al., Selective expression of sense and antisense transcripts of the sushi-ichi-related retrotransposon—derived family during mouse placentogenesis. Retrovirology. Feb. 3, 2015;12:9. doi: 10.1186/s12977-015-0138-8. PMID: 25888968; PMCID: PMC4340606.

Hoadley et al., Multiplatform analysis of 12 cancer types reveals molecular classification within and across tissues of origin. Cell. Aug. 14, 2014;158(4):929-944. doi: 10.1016/j.cell.2014.06.049. Epub Aug. 7, 2014. PMID: 25109877; PMCID: PMC4152462.

Konieczkowski et al., A melanoma cell state distinction influences sensitivity to MAPK pathway inhibitors. Cancer Discov. Jul. 2014;4(7):816-27. doi: 10.1158/2159-8290.CD-13-0424. Epub Apr. 25, 2014. PMID: 24771846; PMCID: PMC4154497.

Kottakis et al., LKB1 loss links serine metabolism to DNA methylation and tumorigenesis. Nature. Nov. 17, 2016;539(7629):390-395. doi: 10.1038/nature20132. Epub Oct. 31, 2016. Erratum in: Nature. Nov. 2019;575(7783):E5. PMID: 27799657; PMCID: PMC5988435.

(56) References Cited

OTHER PUBLICATIONS

Koyama et al., STK11/LKB1 Deficiency Promotes Neutrophil Recruitment and Proinflammatory Cytokine Production to Suppress T-cell Activity in the Lung Tumor Microenvironment. Cancer Res. Mar. 1, 2016;76(5):999-1008. doi: 10.1158/0008-5472.CAN-15-1439. Epub Feb. 1, 2016. PMID: 26833127; PMCID: PMC4775354.

Manguso et al., In vivo CRISPR screening identifies Ptpn2 as a cancer immunotherapy target. Nature. Jul. 27, 2017;547(7664):413-418. doi: 10.1038/nature23270. Epub Jul. 19, 2017.

Marusyk et al., Non-cell-autonomous driving of tumour growth supports sub-clonal heterogeneity. Nature. Oct. 2, 2014;514(7520):54-8. doi: 10.1038/nature13556. Epub Jul. 30, 2014.

Miao et al., Genomic correlates of response to immune checkpoint therapies in clear cell renal cell carcinoma. Science. Feb. 16, 2018;359(6377):801-806. doi: 10.1126/science.aan5951. Epub Jan. 4, 2018. PMID: 29301960; PMCID: PMC6035749.

Pan et al., A major chromatin regulator determines resistance of tumor cells to T cell-mediated killing. Science. Feb. 16, 2018;359(6377):770-775. doi: 10.1126/science.aao1710. Epub Jan. 4, 2018. PMID: 29301958; PMCID: PMC5953516.

Peng et al., Epigenetic silencing of TH1-type chemokines shapes tumour immunity and immunotherapy. Nature. Nov. 12, 2015;527(7577):249-53. doi: 10.1038/nature15520. Epub Oct. 26, 2015. PMID: 26503055; PMCID: PMC4779053.

Perocchi et al., Antisense artifacts in transcriptome microarray experiments are resolved by actinomycin D. Nucleic Acids Res. 2007;35(19):e128. doi: 10.1093/nar/gkm683. Epub Sep. 26, 2007. PMID: 17897965; PMCID: PMC2095812.

Poirier et al., DNA methylation in small cell lung cancer defines distinct disease subtypes and correlates with high expression of EZH2. Oncogene. Nov. 26, 2015;34(48):5869-78. doi: 10.1038/onc.2015.38. Epub Mar. 9, 2015. PMID: 25746006; PMCID: PMC4564363.

Sanjana et al., Improved vectors and genome-wide libraries for CRISPR screening. Nat Methods. Aug. 2014;11(8):783-784. doi: 10.1038/nmeth.3047.

Shalem et al., Genome-scale CRISPR-Cas9 knockout screening in human cells. Science. Jan. 3, 2014;343(6166):84-87. doi: 10.1126/science.1247005. Epub Dec. 12, 2013.

Skoulidis et al., Co-occurring genomic alterations define major subsets of KRAS-mutant lung adenocarcinoma with distinct biology, immune profiles, and therapeutic vulnerabilities. Cancer Discov. Aug. 2015;5(8):860-77. doi: 10.1158/2159-8290.CD-14-1236. Epub Jun. 11, 2015.

Tirosh et al. Dissecting the multicellular ecosystem of metastatic melanoma by single-cell RNA-seq. Science. 2016;352(6282):189-196. doi: 10.1126/science.aad0501.

Wu et al., AXL kinase as a novel target for cancer therapy. Oncotarget. Oct. 30, 2014;5(20):9546-63. doi: 10.18632/oncotarget.2542. PMID: 25337673; PMCID: PMC4259419.

International Preliminary Report on Patentability for PCT/US2020/047985 dated Mar. 10, 2022.

International Search Report and Written Opinion for PCT/US2020/047985 dated Nov. 12, 2020.

Amouzegar et al., 2021. STING Agonists as Cancer Therapeutics. Cancers (Basel). May 30, 2021;13(11):2695. doi: 10.3390/cancers13112695.

Aref et al. 3D microfluidic ex vivo culture of organotypic tumor spheroids to model immune checkpoint blockade. Lab Chip. Oct. 9, 2018;18(20):3129-3143. doi: 10.1039/c8lc00322j.

Aref et al., Screening therapeutic EMT blocking agents in a three-dimensional microenvironment. Integr Biol (Camb). Feb. 2013;5(2):381-9. doi: 10.1039/c2ib20209c. PMID: 23172153; PMCID: PMC4039387.

Bankhead et al. QuPath: Open source software for digital pathology image analysis. Sci Rep. Dec. 4, 2017;7(1):16878. doi: 10.1038/s41598-017-17204-5.

Barber, Sting: infection, inflammation and cancer. Nat Rev Immunol. Dec. 2015;15(12):760-70. doi: 10.1038/nri3921. PMID: 26603901; PMCID: PMC5004891.

Barretina et al., The Cancer Cell Line Encyclopedia enables predictive modelling of anticancer drug sensitivity. Nature. Mar. 28, 2012;483(7391):603-7. doi: 10.1038/nature11003. Erratum in: Nature. Dec. 13, 2012;492(7428):290. Erratum in: Nature. Jan. 2019;565(7738):E5-E6. PMID: 22460905; PMCID: PMC3320027.

Barrowcliffe et al., The anticoagulant activity of heparin: measurement and relationship to chemical structure. J Pharm Biomed Anal. 1989;7(2):217-26. doi: 10.1016/0731-7085(89)80086-x. PMID: 2562205.

Berge et al. Pharmaceutical salts. J Pharm Sci. Jan. 1977;66(1):1-19. doi: 10.1002/jps.2600660104.

Brahmer et al., Safety and activity of anti-PD-L1 antibody in patients with advanced cancer. N Engl J Med. Jun. 28, 2012;366(26):2455-65. doi: 10.1056/NEJMoa1200694. Epub Jun. 2, 2012. PMID: 22658128; PMCID: PMC3563263.

Calabrese et al., Anticancer chemosensitization and radiosensitization by the novel poly(ADP-ribose) polymerase-1 inhibitor AG14361. J Natl Cancer Inst. Jan. 7, 2004;96(1):56-67. doi: 10.1093/jnci/djh005. PMID: 14709739.

Calabrese et al., Identification of potent nontoxic poly(ADP-Ribose) polymerase-1 inhibitors: chemopotentiation and pharmacological studies. Clin Cancer Res. Jul. 2003;9(7):2711-8. PMID: 12855651.

Campisi et al., Tumor-Derived cGAMP Regulates Activation of the Vasculature. Front Immunol. Sep. 4, 2020;11:2090. doi: 10.3389/fimmu.2020.02090.

Canadas et al., Tumor innate immunity primed by specific interferon-stimulated endogenous retroviruses. Nat Med. Aug. 2018;24(8):1143-1150. doi: 10.1038/s41591-018-0116-5. Epub Jul. 23, 2018.

Carey et al., Topological analysis reveals a PD-L1-associated microenvironmental niche for Reed-Sternberg cells in Hodgkin lymphoma. Blood. Nov. 30, 2017;130(22):2420-2430. doi: 10.1182/blood-2017-03-770719. Epub Sep. 11, 2017. PMID: 28893733; PMCID: PMC5766840.

Chin et al., Antitumor activity of a systemic STING-activating non-nucleotide cGAMP mimetic. Science. Aug. 21, 2020;369(6506):993-999. doi: 10.1126/science.abb4255.

Chuong et al., Regulatory evolution of innate immunity through co-option of endogenous retroviruses. Science. Mar. 4, 2016;351(6277):1083-7. doi: 10.1126/science.aad5497.

Cordova et al., Human SLC46A2 Is the Dominant cGAMP Importer in Extracellular cGAMP-Sensing Macrophages and Monocytes. ACS Cent Sci. Jun. 23, 2021;7(6):1073-1088. doi: 10.1021/acscentsci.1c00440. Epub Jun. 7, 2021.

Crescenzo et al., Convergent mutations and kinase fusions lead to oncogenic STAT3 activation in anaplastic large cell lymphoma. Cancer Cell. Apr. 13, 2015;27(4):516-32. doi: 10.1016/j.ccell.2015.03.006. Erratum in: Cancer Cell. May 11, 2015;27(5):744.

Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80. doi: 10.1073/pnas.0915174107. Epub Feb. 16, 2010. PMID: 20160101; PMCID: PMC2840093.

Dai et al., Acetylation Blocks cGAS Activity and Inhibits Self-DNA-Induced Autoimmunity. Cell. Mar. 7, 2019;176(6):1447-1460.e14. doi: 10.1016/j.cell.2019.01.016. Epub Feb. 21, 2019.

Deng et al., STING-Dependent Cytosolic DNA Sensing Promotes Radiation-Induced Type I Interferon-Dependent Antitumor Immunity in Immunogenic Tumors. Immunity. Nov. 20, 2014;41(5):843-52. doi: 10.1016/j.immuni.2014.10.019. Epub Nov. 6, 2014.

Deng et al., ULK1 inhibition overcomes compromised antigen presentation and restores antitumor immunity in LKB1 mutant lung cancer. Nat Cancer. May 2021;2(5):503-514. doi: 10.1038/s43018-021-00208-6. Epub May 17, 2021.

Ding et al., PARP Inhibition Elicits STING-Dependent Antitumor Immunity in Brca1-Deficient Ovarian Cancer. Cell Rep. Dec. 11, 2018;25(11):2972-2980.e5. doi: 10.1016/j.celrep.2018.11.054.

Doench et al., Optimized sgRNA design to maximize activity and minimize off-target effects of CRISPR-Cas9. Nat Biotechnol. Feb. 2016;34(2):184-191. doi: 10.1038/nbt.3437. Epub Jan. 18, 2016. PMID: 26780180; PMCID: PMC4744125.

Dolan et al., PD-1 pathway inhibitors: changing the landscape of cancer immunotherapy. Cancer Control. Jul. 2014;21(3):231-7. doi: 10.1177/107327481402100308. PMID: 24955707.

(56) References Cited

OTHER PUBLICATIONS

Falahat et al., STING Signaling in Melanoma Cells Shapes Antigenicity and Can Promote Antitumor T-cell Activity. Cancer Immunol Res. Nov. 2019;7(11):1837-1848. doi: 10.1158/2326-6066.CIR-19-0229. Epub Aug. 28, 2019.
Falahat et al., Epigenetic reprogramming of tumor cell-intrinsic STING function sculpts antigenicity and T cell recognition of melanoma. Proc Natl Acad Sci U S A. Apr. 13, 2021;118(15):e2013598118. doi: 10.1073/pnas.2013598118.
Gao et al., Cyclic GMP-AMP synthase is an innate immune sensor of HIV and other retroviruses. Science. Aug. 23, 2013;341(6148):903-6. doi: 10.1126/science.1240933. Epub Aug. 8, 2013. PMID: 23929945; PMCID: PMC3860819.
GENBANK Submission; NIH/NCBI, Accession No. NM_001100422.1, *Homo sapiens* spermatogenesis associated serine rich 2 like (SPATS2L), transcript variant 2, mRNA, Reddy et al., Mar. 14, 2018. 6 Pages.
GENBANK Submission; NIH/NCBI, Accession No. NM_001308078.1, *Homo sapiens* interleukin 32 (IL32), transcript variant 9, mRNA, Shamoun et al., Mar. 29, 2018. 4 Pages.
GENBANK Submission; NIH/NCBI, Accession No. NM_004155.5, *Homo sapiens* serpin family B member 9 (SERPINB9), mRNA, Lauricella et al., Mar. 15, 2018. 4 Pages.
GENBANK Submission; NIH/NCBI, Accession No. NM_005233.5, *Homo sapiens* EPH receptor A3 (EPHA3), transcript variant 1, mRNA, Caivano et al., Mar. 17, 2018. 5 Pages.
GENBANK Submission; NIH/NCBI, Accession No. NM_006074.4, *Homo sapiens* tripartite motif containing 22 (TRIM22), transcript variant 1, mRNA, Lim et al., Dec. 29, 2017. 4 Pages.
GENBANK Submission; NIH/NCBI, Accession No. NM_006355.4, *Homo sapiens* tripartite motif containing 38 (TRIM38), mRNA, Lin et al., Feb. 11, 2018. 4 Pages.
GENBANK Submission; NIH/NCBI, Accession No. NM_006820.3, *Homo sapiens* interferon induced protein 44 like (IFI44L), mRNA, Haralambieva et al., Oct. 3, 2017. 4 Pages.
GENBANK Submission; NIH/NCBI, Accession No. NM_012228.3, *Homo sapiens* methionine sulfoxide reductase B2 (MSRB2), mRNA, Cudic et al., Feb. 5, 2018. 3 Pages.
GENBANK Submission; NIH/NCBI, Accession No. NM_014606.2, *Homo sapiens* HECT and RLD domain containing E3 ubiquitin protein ligase 3 (HERC3), transcript variant 1, mRNA, Hochrainer et al., Apr. 2, 2018. 5 Pages.
GENBANK Submission; NIH/NCBI, Accession No. NM_016108.3, *Homo sapiens* androgen induced 1 (AIG1), transcript variant 1, mRNA, Parsons et al., Feb. 5, 2018. 3 Pages.
GENBANK Submission; NIH/NCBI, Accession No. NM_021138.3, *Homo sapiens* TNF receptor associated factor 2 (TRAF2), mRNA, Ceccarelli et al., Mar. 29, 2018. 5 Pages.
GENBANK Submission; NIH/NCBI, Accession No. NM_032208.2, *Homo sapiens* anthrax toxin receptor 1 (ANTXR1), transcript variant 1, mRNA, Miles et al., Mar. 4, 2018. 5 Pages.
GENBANK Submission; NIH/NCBI, Accession No. NM_033274.4, *Homo sapiens* ADAM metallopeptidase domain 19 (ADAM19), mRNA, Perez-Rubio et al., Apr. 2, 2018. 6 Pages.
GENBANK Submission; NIH/NCBI, Accession No. NM_152731.2, *Homo sapiens* BEN domain containing 6 (BEND6), transcript variant 1, mRNA, Dai et al., Oct. 2, 2017. 2 Pages.
GENBANK Submission; NIH/NCBI, Accession No. NM_198282.3, *Homo sapiens* transmembrane protein 173 (TMEM173), transcript variant 1, mRNA, Choi et al., Mar. 17, 2018. 5 Pages.
GENBANK Submission; NIH/NCBI, Accession No. NP_001093892.1, SPATS2-like protein isoform a [*Homo sapiens*], Reddy et al., Mar. 14, 2018. 4 Pages.
GENBANK Submission; NIH/NCBI, Accession No. NP_001295007.1, interleukin-32 isoform E precursor [*Homo sapiens*], Shamoun et al., Mar. 29, 2018. 3 Pages.
GENBANK Submission; NIH/NCBI, Accession No. NP_004146.1, serpin B9 [*Homo sapiens*], Lauricella et al., Mar. 15, 2018. 3 Pages.
GENBANK Submission; NIH/NCBI, Accession No. NP_004976.2, GTPase KRas isoform b [*Homo sapiens*], Nikolaev et al., Mar. 29, 2018. 3 Pages.
GENBANK Submission; NIH/NCBI, Accession No. NP_005224.2, ephrin type-A receptor 3 isoform a precursor [*Homo sapiens*], Caivano et al., Mar. 17, 2018. 3 Pages.
GENBANK Submission; NIH/NCBI, Accession No. NP_006065.2, E3 ubiquitin-protein ligase TRIM22 isoform 1 [*Homo sapiens*], Lim et al., Dec. 29, 2017. 3 Pages.
GENBANK Submission; NIH/NCBI, Accession No. NP_006346.1, E3 ubiquitin-protein ligase TRIM38 [*Homo sapiens*], Lin et al., Feb. 11, 2018. 3 Pages.
GENBANK Submission; NIH/NCBI, Accession No. NP_006811.2, interferon-induced protein 44-like [*Homo sapiens*], Haralambieva et al., Oct. 3, 2017. 2 Pages.
GENBANK Submission; NIH/NCBI, Accession No. NP_036360.3, methionine-R-sulfoxide reductase B2, mitochondrial precursor [*Homo sapiens*], Cudic et al., Feb. 5, 2018. 3 Pages.
GENBANK Submission; NIH/NCBI, Accession No. NP_055421.1, probable E3 ubiquitin-protein ligase HERC3 isoform 1 [*Homo sapiens*], Hochrainer et al., Apr. 2, 2018. 3 Pages.
GENBANK Submission; NIH/NCBI, Accession No. NP_057192.2, androgen-induced gene 1 protein isoform a [*Homo sapiens*], Parsons et al., Feb. 5, 2018. 2 Pages.
GENBANK Submission; NIH/NCBI, Accession No. NP_066961.2, TNF receptor-associated factor 2 [*Homo sapiens*], Ceccarelli et al., Mar. 29, 2018. 3 Pages.
GENBANK Submission; NIH/NCBI, Accession No. NP_115584.1, anthrax toxin receptor 1 isoform 1 precursor [*Homo sapiens*], Miles et al., Mar. 4, 2018. 3 Pages.
GENBANK Submission; NIH/NCBI, Accession No. NP_150377.1, disintegrin and metalloproteinase domain-containing protein 19 preproprotein [*Homo sapiens*], Perez-Rubio et al., Apr. 2, 2018. 3 Pages.
GENBANK Submission; NIH/NCBI, Accession No. NP_689944.2, BEN domain-containing protein 6 isoform 1 [*Homo sapiens*], Dai et al., Oct. 2, 2017. 1 Page.
GENBANK Submission; NIH/NCBI, Accession No. NP_938023.1, stimulator of interferon genes protein isoform 1 [*Homo sapiens*], Choi et al., Mar. 17, 2018. 4 Pages.
Grabosch et al. Cisplatin-induced immune modulation in ovarian cancer mouse models with distinct inflammation profiles. Oncogene. Mar. 2019;38(13):2380-2393. doi: 10.1038/s41388-018-0581-9. Epub Dec. 5, 2018.
Guan et al. MLH1 Deficiency-Triggered DNA Hyperexcision by Exonuclease 1 Activates the cGAS-STING Pathway. Cancer Cell. Jan. 11, 2021;39(1):109-121.e5. doi: 10.1016/j.ccell.2020.11.004. Epub Dec. 17, 2020.
Gulen et al., Signalling strength determines proapoptotic functions of STING. Nat Commun. Sep. 5, 2017;8(1):427. doi: 10.1038/s41467-017-00573-w.
Harding et al., Mitotic progression following DNA damage enables pattern recognition within micronuclei. Nature. Aug. 24, 2017;548(7668):466-470. doi: 10.1038/nature23470. Epub Jul. 31, 2017.
Hopfner et al. Molecular mechanisms and cellular functions of cGAS-STING signalling. Nat Rev Mol Cell Biol. Sep. 2020;21(9):501-521. doi: 10.1038/s41580-020-0244-x. Epub May 18, 2020.
Jagtap et al., Poly(ADP-ribose) polymerase and the therapeutic effects of its inhibitors. Nat Rev Drug Discov. May 2005;4(5):421-40. doi: 10.1038/nrd1718. PMID: 15864271.
Jenkins et al., Ex Vivo Profiling of PD-1 Blockade Using Organotypic Tumor Spheroids. Cancer Discov. Feb. 2018;8(2):196-215. doi: 10.1158/2159-8290.CD-17-0833. Epub Nov. 3, 2017. PMID: 29101162; PMCID: PMC5809290.
Junttila et al., Influence of tumour micro-environment heterogeneity on therapeutic response. Nature. Sep. 19, 2013;501(7467):346-54. doi: 10.1038/nature12626. PMID: 24048067.
Kaufman et al. A Transcriptional Signature Identifies LKB1 Functional Status as a Novel Determinant of MEK Sensitivity in Lung Adenocarcinoma. Cancer Res. Jan. 1, 2017;77(1):153-163. doi: 10.1158/0008-5472.CAN-16-1639. Epub Nov. 7, 2016.

(56) References Cited

OTHER PUBLICATIONS

Keenan et al., Genomic correlates of response to immune checkpoint blockade. Nat Med. Mar. 2019;25(3):389-402. doi: 10.1038/s41591-019-0382-x. Epub Mar. 6, 2019.
Kim et al., Characterizing genomic alterations in cancer by complementary functional associations. Nat Biotechnol. May 2016;34(5):539-46. doi: 10.1038/nbt.3527. Epub Apr. 18, 2016. PMID: 27088724; PMCID: PMC4868596.
Kitajima et al., Overcoming Resistance to Dual Innate Immune and MEK Inhibition Downstream of KRAS. Cancer Cell. Sep. 10, 2018;34(3):439-452.e6. doi: 10.1016/j.ccell.2018.08.009.
Kitajima et al. Suppression of STING Associated with LKB1 Loss in KRAS-Driven Lung Cancer. Cancer Discov. Jan. 2019;9(1):34-45. doi: 10.1158/2159-8290.CD-18-0689. Epub Oct. 8, 2018.
Konno et al. Suppression of STING signaling through epigenetic silencing and missense mutation impedes DNA damage mediated cytokine production. Oncogene. Apr. 2018;37(15):2037-2051. doi: 10.1038/s41388-017-0120-0. Epub Jan. 25, 2018.
Koyama et al. Stk11/lkb1 deficiency promotes neutrophil recruitment and proinflammatory cytokine production to suppress t-cell activity in the lung tumor microenvironment. cancer res. Mar. 1, 2016;76(5):999-1008. doi: 10.1158/0008-5472.CAN-15-1439. Epub Feb. 1, 2016.
Kwon et al., The Cytosolic DNA-Sensing cGAS-STING Pathway in Cancer. Cancer Discov. Jan. 2020;10(1):26-39. doi: 10.1158/2159-8290.CD-19-0761. Epub Dec. 18, 2019.
Li et al., The cGAS-cGAMP-STING pathway connects DNA damage to inflammation, senescence, and cancer. J Exp Med. May 7, 2018;215(5):1287-1299. doi: 10.1084/jem.20180139. Epub Apr. 5, 2018.
Linhardt et al., Differential anticoagulant activity of heparin fragments prepared using microbial heparinase. J Biol Chem. Jul. 10, 1982;257(13):7310-3. PMID: 7085627.
London et al., Signalling dynamics in the spindle checkpoint response. Nat Rev Mol Cell Biol. Nov. 2014;15(11):736-47. doi: 10.1038/nrm3888. Epub Oct. 10, 2014.
Lu et al., Engineered PLGA microparticles for long-term, pulsatile release of STING agonist for cancer immunotherapy. Sci Transl Med. Aug. 12, 2020;12(556):eaaz6606. doi: 10.1126/scitranslmed.aaz6606. PMID: 32801144; PMCID: PMC9019818.
Lu et al., DNA Sensing in Mismatch Repair-Deficient Tumor Cells Is Essential for Anti-tumor Immunity. Cancer Cell. Jan. 11, 2021;39(1):96-108.e6. doi: 10.1016/j.ccell.2020.11.006. Epub Dec. 17, 2020.
Luo et al., HPV16 drives cancer immune escape via NLRX1-mediated degradation of STING. J Clin Invest. Apr. 1, 2020;130(4):1635-1652. doi: 10.1172/JCI129497.
Luteijn,, et al., SLC19A1 transports immunoreactive cyclic dinucleotides. Nature. Sep. 2019;573(7774):434-438. doi: 10.1038/s41586-019-1553-0. Epub Sep. 11, 2019. Erratum in: Nature. Mar. 2020;579(7800):E12.
Mackenzie et al., cGAS surveillance of micronuclei links genome instability to innate immunity. Nature. Aug. 24, 2017;548(7668):461-465. doi: 10.1038/nature23449. Epub Jul. 24, 2017.
Mahadevan et al., Intrinsic Immunogenicity of Small Cell Lung Carcinoma Revealed by Its Cellular Plasticity. Cancer Discov. Aug. 2021;11(8):1952-1969. doi: 10.1158/2159-8290.CD-20-0913. Epub Mar. 11, 2021.
Maia et al., Mps1 inhibitors synergise with low doses of taxanes in promoting tumour cell death by enhancement of errors in cell division. Br J Cancer. Jun. 2018;118(12):1586-1595. doi: 10.1038/s41416-018-0081-2. Epub May 8, 2018.
Marabelle et al., Starting the fight in the tumor: expert recommendations for the development of human intratumoral immunotherapy (HIT-IT). Ann Oncol. Nov. 1, 2018;29(11):2163-2174. doi: 10.1093/annonc/mdy423. PMID: 30295695; PMCID: PMC6290929.
Mason et al., Functional characterization of CFI-402257, a potent and selective Mps1/TTK kinase inhibitor, for the treatment of cancer. Proc Natl Acad Sci U S A. Mar. 21, 2017;114(12):3127-3132. doi: 10.1073/pnas.1700234114. Epub Mar. 7, 2017.

Mohr et al., ER-directed TREX1 limits cGAS activation at micronuclei. Mol Cell. Feb. 18, 2021;81(4):724-738.e9. doi: 10.1016/j.molcel.2020.12.037. Epub Jan. 20, 2021.
Morel et al., EZH2 inhibition activates a dsRNA-STING-interferon stress axis that potentiates response to PD-1 checkpoint blockade in prostate cancer. Nat Cancer. Apr. 2021;2(4):444-456. doi: 10.1038/s43018-021-00185-w. Epub Mar. 22, 2021.
Oser et al., The KDM5A/RBP2 histone demethylase represses NOTCH signaling to sustain neuroendocrine differentiation and promote small cell lung cancer tumorigenesis. Genes Dev. Dec. 1, 2019;33(23-24):1718-1738. doi: 10.1101/gad.328336.119. Epub Nov. 14, 2019. PMID: 31727771; PMCID: PMC6942053.
Pan et al., An orally available non-nucleotide STING agonist with antitumor activity. Science. Aug. 21, 2020;369(6506):eaba6098. doi: 10.1126/science.aba6098.
Pantelidou et al., PARP Inhibitor Efficacy Depends on CD8+ T-cell Recruitment via Intratumoral STING Pathway Activation in BRCA-Deficient Models of Triple-Negative Breast Cancer. Cancer Discov. Jun. 2019;9(6):722-737. doi: 10.1158/2159-8290.CD-18-1218. Epub Apr. 23, 2019.
Poli et al., Glycol-split nonanticoagulant heparins are inhibitors of hepcidin expression in vitro and in vivo. Blood. Mar. 6, 2014;123(10):1564-73. doi: 10.1182/blood-2013-07-515221. Epub Jan. 7, 2014. PMID: 24398330; PMCID: PMC3945865.
Rao et al., Low anticoagulant heparin targets multiple sites of inflammation, suppresses heparin-induced thrombocytopenia, and inhibits interaction of RAGE with its ligands. Am J Physiol Cell Physiol. Jul. 2010;299(1):C97-110. doi: 10.1152/ajpcell.00009.2010. Epub Apr. 7, 2010. PMID: 20375277.
Reislander et al., DNA Damage and Cancer Immunotherapy: A STING in the Tale. Mol Cell. Oct. 1, 2020;80(1):21-28. doi: 10.1016/j.molcel.2020.07.026. Epub Aug. 17, 2020.
Reislander et al., BRCA2 abrogation triggers innate immune responses potentiated by treatment with PARP inhibitors. Nat Commun. Jul. 17, 2019;10(1):3143. doi: 10.1038/s41467-019-11048-5.
Rhodes et al., Regulation of Immunity by Butyrophilins. Annu Rev Immunol. May 20, 2016;34:151-72. doi: 10.1146/annurev-immunol-041015-055435. Epub Jan. 11, 2016. PMID: 26772212.
Ritchie et al., SLC19A1 Is an Importer of the Immunotransmitter cGAMP. Mol Cell. Jul. 25, 2019;75(2):372-381.e5. doi: 10.1016/j.molcel.2019.05.006. Epub May 21, 2019.
Ritter et al., Phosphorylation of RAB7 by TBK1/IKKε Regulates Innate Immune Signaling in Triple-Negative Breast Cancer. Cancer Res. Jan. 1, 2020;80(1):44-56. doi: 10.1158/0008-5472.CAN-19-1310. Epub Oct. 29, 2019.
Rizvi et al., Molecular Determinants of Response to Anti-Programmed Cell Death (PD)-1 and Anti-Programmed Death-Ligand 1 (PD-L1) Blockade in Patients With Non-Small-Cell Lung Cancer Profiled With Targeted Next-Generation Sequencing. J Clin Oncol. Mar. 1, 2018;36(7):633-641. doi: 10.1200/JCO.2017.75.3384. Epub Jan. 16, 2018. Erratum in: J Clin Oncol. Jun. 1, 2018;36(16):1645.
Roulois et al., DNA-Demethylating Agents Target Colorectal Cancer Cells by Inducing Viral Mimicry by Endogenous Transcripts. Cell. Aug. 27, 2015;162(5):961-73. doi: 10.1016/j.cell.2015.07.056. PMID: 26317465; PMCID: PMC4843502.
Saibil et al., Targeting T Cell Activation in Immuno-Oncology. Current Oncology. 2020; 27(s2):98-105.
Sholl, Molecular diagnostics of lung cancer in the clinic. Transl Lung Cancer Res. Oct. 2017;6(5):560-569. doi: 10.21037/tlcr.2017.08.03.
Skoulidis et al., STK11/LKB1 Mutations and PD-1 Inhibitor Resistance in KRAS-Mutant Lung Adenocarcinoma. Cancer Discov. Jul. 2018;8(7):822-835. doi: 10.1158/2159-8290.CD-18-0099. Epub May 17, 2018.
Spranger et al. Impact of oncogenic pathways on evasion of antitumour immune responses. Nat Rev Cancer. Mar. 2018;18(3):139-147. doi: 10.1038/nrc.2017.117. Epub Jan. 12, 2018.
Sunshine et al., PD-1/PD-L1 inhibitors. Curr Opin Pharmacol. Aug. 2015;23:32-8. doi: 10.1016/j.coph.2015.05.011. Epub Jun. 2, 2015. PMID: 26047524; PMCID: PMC4516625.

(56) References Cited

OTHER PUBLICATIONS

Tabassum et al., Tumorigenesis: it takes a village. Nat Rev Cancer. Aug. 2015;15(8):473-83. doi: 10.1038/nrc3971. Epub Jul. 2, 2015. PMID: 26156638.

Topalian et al., Safety, activity, and immune correlates of anti-PD-1 antibody in cancer. N Engl J Med. Jun. 28, 2012;366(26):2443-54. doi: 10.1056/NEJMoa1200690. Epub Jun. 2, 2012. PMID: 22658127; PMCID: PMC3544539.

Topper et al., The emerging role of epigenetic therapeutics in immuno-oncology. Nat Rev Clin Oncol. Feb. 2020;17(2):75-90. doi: 10.1038/s41571-019-0266-5. Epub Sep. 23, 2019.

Veuger et al., Radiosensitization and DNA repair inhibition by the combined use of novel inhibitors of DNA-dependent protein kinase and poly(ADP-ribose) polymerase-1. Cancer Res. Sep. 15, 2003;63(18):6008-15. PMID: 14522929.

Wang et al., Tumour sensitization via the extended intratumoural release of a STING agonist and camptothecin from a self-assembled hydrogel. Nat Biomed Eng. Nov. 2020;4(11):1090-1101. doi: 10.1038/s41551-020-0597-7. Epub Aug. 10, 2020. PMID: 32778697; PMCID: PMC8848303.

Wengner et al., Novel Mps1 Kinase Inhibitors with Potent Antitumor Activity. Mol Cancer Ther. Apr. 2016;15(4):583-92. doi: 10.1158/1535-7163.MCT-15-0500. Epub Feb. 1, 2016.

Woo et al., STING-dependent cytosolic DNA sensing mediates innate immune recognition of immunogenic tumors. Immunity. Nov. 20, 2014;41(5):830-42. doi: 10.1016/j.immuni.2014.10.017. Epub Nov. 5, 2014. Erratum in: Immunity. Jan. 20, 2015;42(1):199.

Xia et al., Deregulation of STING Signaling in Colorectal Carcinoma Constrains DNA Damage Responses and Correlates With Tumorigenesis. Cell Rep. Jan. 12, 2016;14(2):282-97. doi: 10.1016/j.celrep.2015.12.029. Epub Dec. 31, 2015.

Xia et al., Recurrent Loss of STING Signaling in Melanoma Correlates with Susceptibility to Viral Oncolysis. Cancer Res. Nov. 15, 2016;76(22):6747-6759. doi: 10.1158/0008-5472.CAN-16-1404. Epub Sep. 28, 2016.

Yau et al., DNA hypomethylating agents increase activation and cytolytic activity of CD8+ T cells. Mol Cell. Apr. 1, 2021;81(7):1469-1483.e8. doi: 10.1016/j.molcel.2021.01.038. Epub Feb. 19, 2021.

Zhang et al., Structures and Mechanisms in the cGAS-STING Innate Immunity Pathway. Immunity. Jul. 14, 2020;53(1):43-53. doi: 10.1016/j.immuni.2020.05.013.

Zierhut et al., Regulation and Consequences of cGAS Activation by Self-DNA. Trends Cell Biol. Aug. 2020;30(8):594-605. doi: 10.1016/j.tcb.2020.05.006. Epub Jun. 13, 2020.

Zierhut, et al., The Cytoplasmic DNA Sensor cGAS Promotes Mitotic Cell Death. Cell. Jul. 11, 2019;178(2):302-315.e23. doi: 10.1016/j.cell.2019.05.035.

* cited by examiner

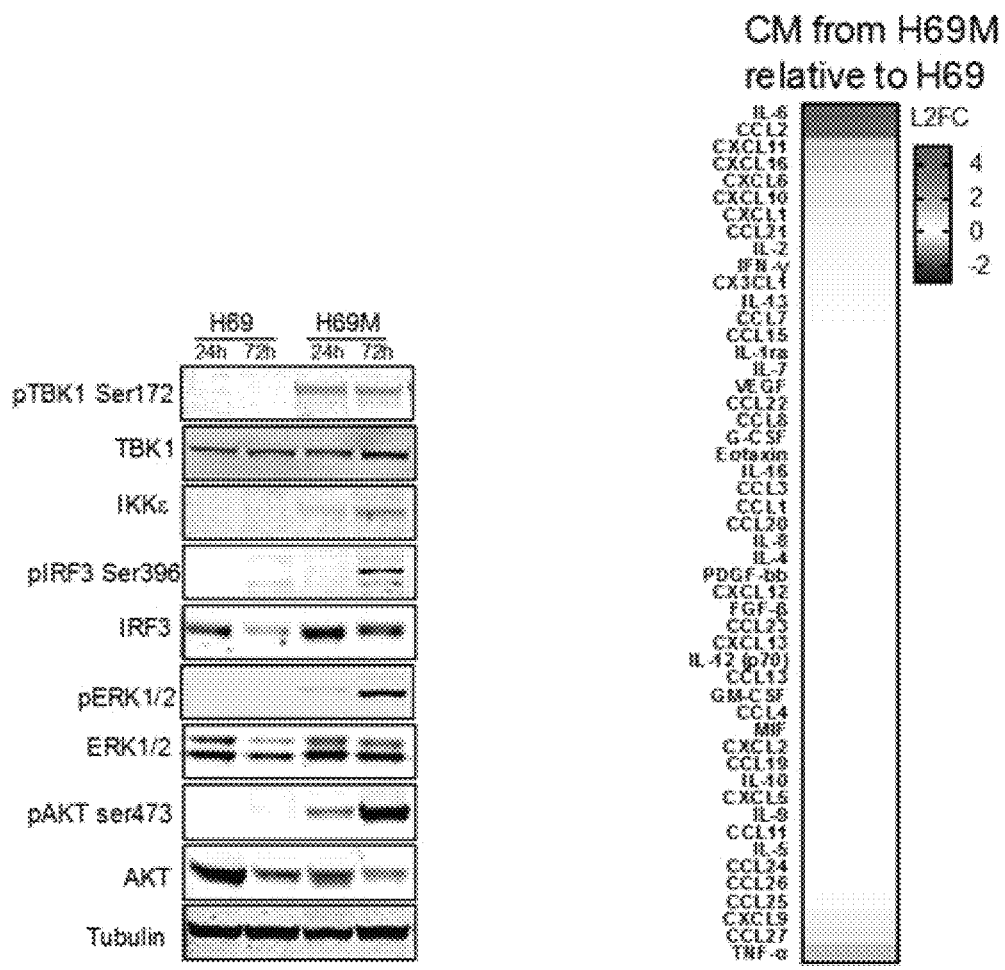
Figure 1A
Figure 1B
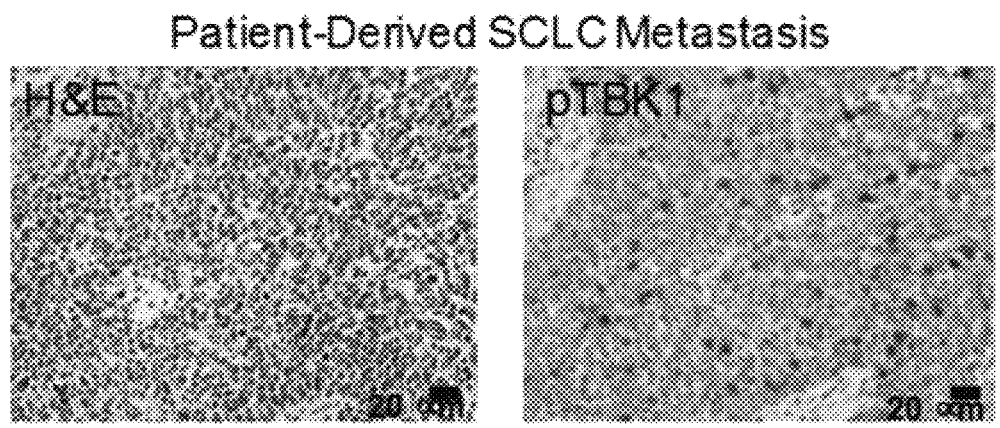
Figure 1C

| | | | IC | FDR |
|---|---|---|---|---|
| | TCGA (Pancan12) | SPARCS Signature | | |
| Epigenetic | | NUYTTEN EZH2 TARGETS UP | 0.8 | <0.1 |
| | | PASINI SUZ12 TARGETS DN | 0.595 | <0.1 |
| | | LIANG SILENCED BY METHYLATION 2 | 0.605 | <0.1 |
| | | MIKKELSEN MEF LCP WITH H3K4ME3 | 0.701 | <0.1 |
| | | JACKSON DNMT1 TARGETS UP | 0.493 | <0.1 |
| TNF/NF-KB | | PHONG TNF RESPONSE NOT VIA P38 | 0.72 | <0.1 |
| | | SANA TNF SIGNALING UP | 0.765 | <0.1 |
| | | HINATA NFKB TARGETS KERATINOCYTE UP | 0.652 | <0.1 |
| | | ZHANG RESPONSE TO IKK INHIBITOR AND TNF UP | 0.658 | <0.1 |
| | | SCHOEN NFKB SIGNALING | 0.655 | <0.1 |
| | | HINATA NFKB TARGETS FIBROBLAST UP | 0.62 | <0.1 |
| Inflammation/Innate | | DER IFN GAMMA RESPONSE UP | 0.654 | <0.1 |
| | | SEKI INFLAMMATORY RESPONSE LPS UP | 0.712 | <0.1 |
| | | DER IFN BETA RESPONSE UP | 0.599 | <0.1 |
| | | DER IFN ALPHA RESPONSE UP | 0.507 | <0.1 |
| | | GEISS RESPONSE TO DSRNA UP | 0.673 | <0.1 |
| | | KEGG CYTOKINE CYTOKINE RECEPTOR INTERACTION | 0.737 | <0.1 |
| | | FULCHER INFLAMMATORY RESPONSE LECTIN VS LPS UP | 0.741 | <0.1 |
| | | NEMETH INFLAMMATORY RESPONSE LPS UP | 0.575 | <0.1 |
| | | WIELAND UP BY HBV INFECTION | 0.681 | <0.1 |
| RTK/RAS | | RUTELLA RESPONSE TO HGF UP | 0.690 | <0.1 |
| | | PID INTEGRIN1 PATHWAY | 0.695 | <0.1 |
| | | XU HGF SIGNALING NOT VIA AKT1 6HR | 0.497 | <0.1 |
| | | BILD HRAS ONCOGENIC SIGNATURE | 0.443 | <0.1 |
| | | SWEET KRAS TARGETS UP | 0.635 | <0.1 |

Figure 3A

| Immune signature | q value |
|---|---|
| IIR | 9.68E-275 |
| MDSC | 7.73E-257 |
| AIR | 1.41E-201 |
| Neutrophils | 2.41E-131 |
| Macrophages | 4.60E-126 |
Figure 4C
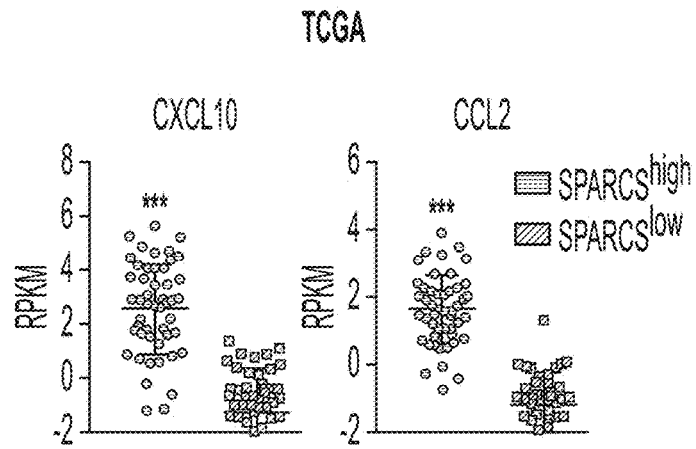
Figure 4D
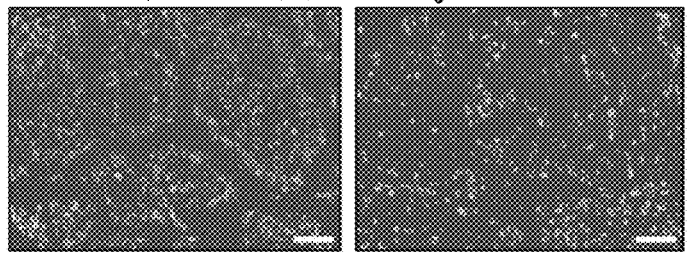
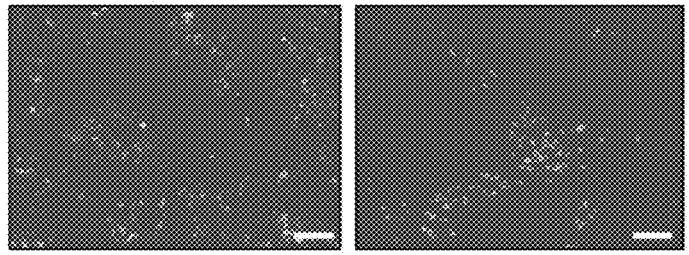
Figure 4E

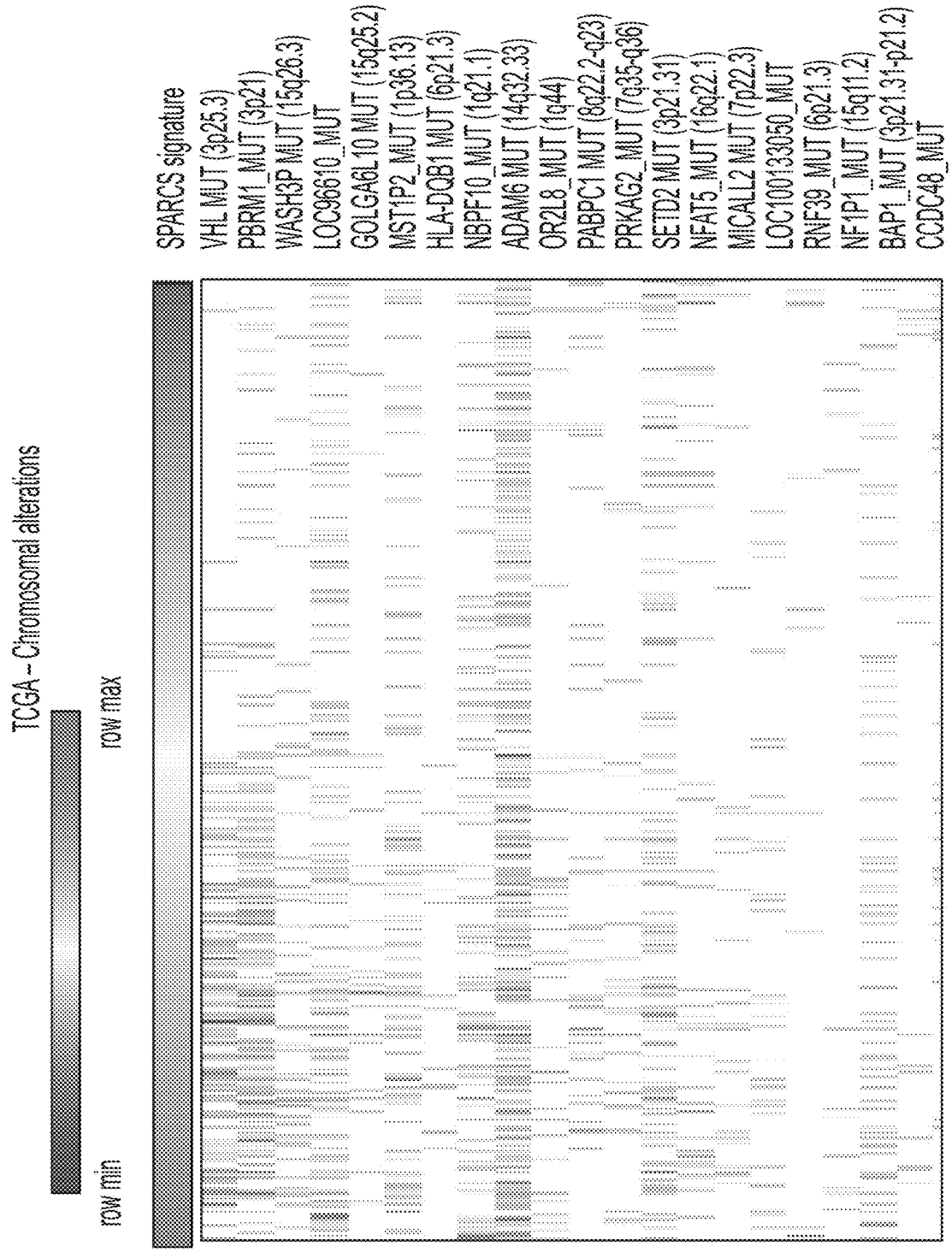
Figure 12.A

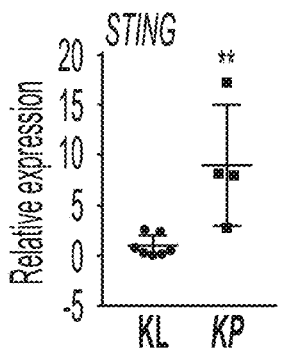
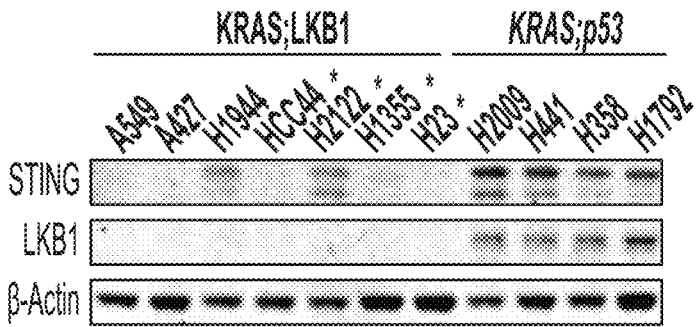
Figure 15A  Figure 15B
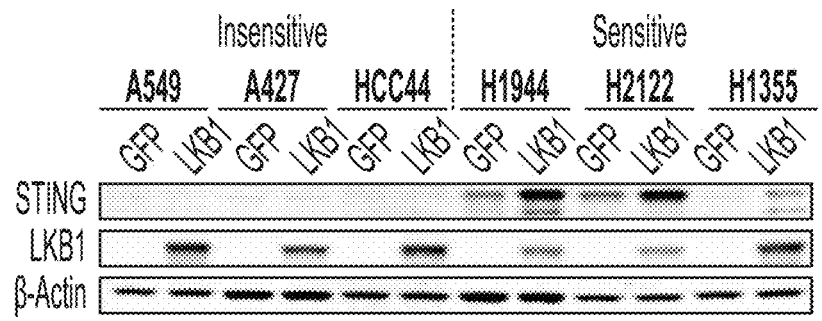
Figure 16A
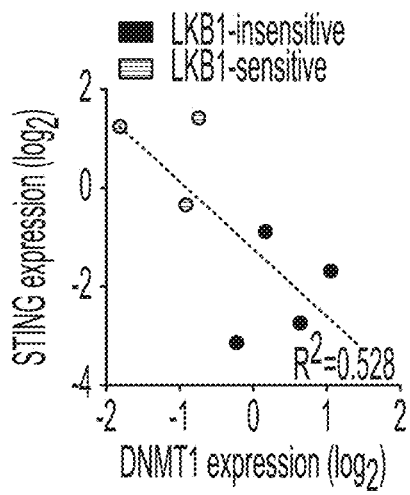
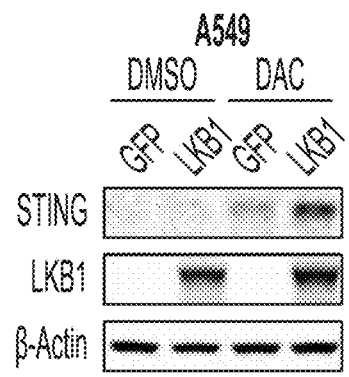
Figure 16B  Figure 16C

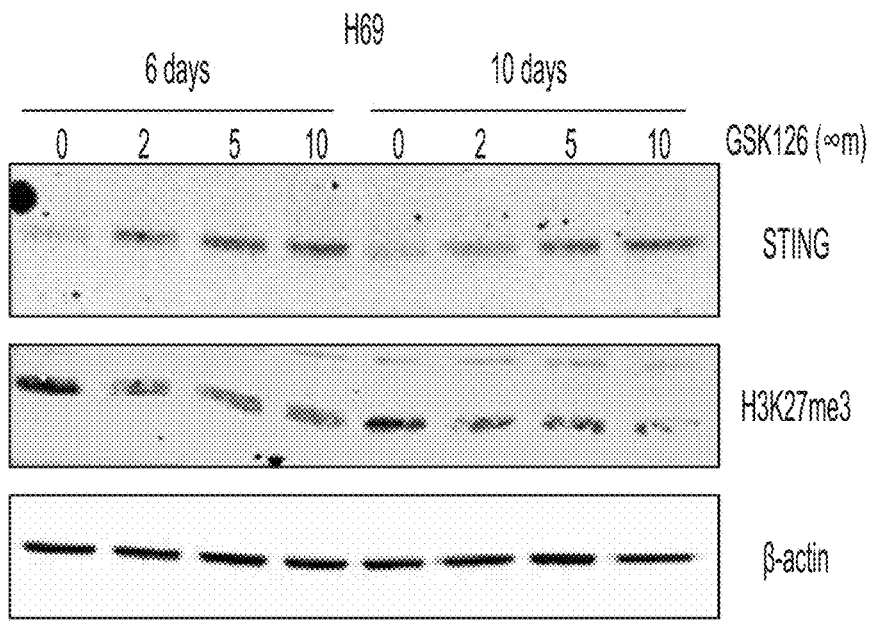
Figure 19
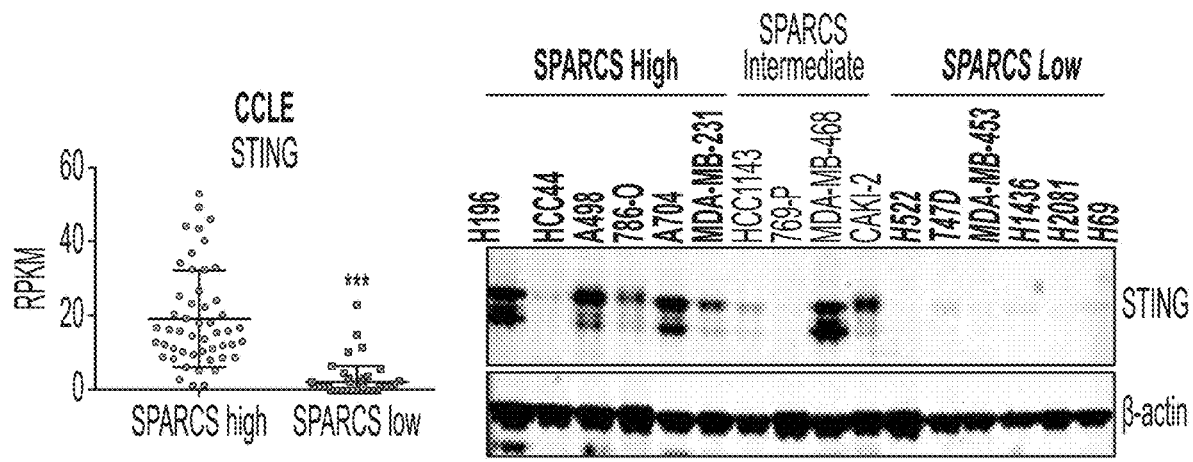
Figure 20A
Figure 20B

Breast cancer cell line
| | |
|---|---|
| MDAMB231 | ER-/PR-/HER2- |
| MDAMB468 | ER-/PR-/HER2- |
| HCC70 | ER-/PR-/HER2- |
| HCC1143 | ER-/PR-/HER2- |
| HCC1187 | ER-/PR-/HER2- |
| HCC1937 | ER-/PR-/HER2- |
| MCF7 | ER+/PR+/HER2- |
| T47D | ER+/PR+/HER2- |
| CAMA1 | ER+/PR+/HER2- |
| MDAMB175 | ER+/PR-/HER2- |
| ZR751 | ER+/PR-/HER2- |
| MDAMB361 | ER+/PR+/HER2+ |
| BT474 | ER+/PR+/HER2+ |
| SKBR3 | ER-/PR-/HER2+ |
| HCC1569 | ER-/PR-/HER2+ |

STING LEVELS AS A BIOMARKER FOR CANCER IMMUNOTHERAPY

RELATED APPLICATIONS

This application is a national stage filing under 35 U.S.C. § 371 of International PCT Application PCT/US2019/025959, filed Apr. 5, 2019, which claims the benefit under 35 U.S.C. § 119(e) of U.S. Provisional Patent Application No. 62/653,223, filed on Apr. 5, 2018, entitled "STING LEVELS AS A BIOMARKER FOR CANCER IMMUNOTHERAPY," the entire contents of each of which is are incorporated by reference herein.

FEDERALLY SPONSORED RESEARCH

This invention was made with government support under R01 CA190394 awarded by the National Institutes of Health. The government has certain rights in the invention.

BACKGROUND OF INVENTION

Tumor cell heterogeneity promotes cancer progression, as subclones can exhibit different growth properties, metastatic capacity, and drug sensitivity, and provide paracrine immune signals. One type of tumor cell heterogeneity accompanies the epithelial-mesenchymal transition (EMT). The EMT is a process by which epithelial cells lose their cell polarity and cell-cell adhesion, and gain migratory and invasive properties to become mesenchymal stem cells. EMT is essential for initiation of metastasis in cancer progression. Carcinoma cells in a primary tumor lose cell-cell adhesion mediated by E-cadherin repression and break through the basement membrane with increased invasive properties, and enter the bloodstream through intravasation. Later, when these circulating tumor cells (CTCs) exit the bloodstream to form micro-metastases, they undergo MET for clonal outgrowth at these metastatic sites. Thus, EMT and MET form the initiation and completion of the invasion-metastasis cascade. A mesenchymal AXL/NF-kB high state associates with therapeutic resistance across multiple cancer types. Accordingly, new methods are needed for identifying and treating cancer cells according to cell state.

BRIEF SUMMARY OF INVENTION

The present disclosure is based on the surprising discovery that the level of STING and/or one or more SPARCS genes can be used as a biomarker to determine an effective cancer therapy. For example, certain cancer cells, e.g., certain tumor cells, possess high levels of STING and/or high levels of expression of one or more SPARCS genes, and that high levels of STING and/or high levels of expression of one or more SPARCS genes is a biomarker for susceptibility of cancer cells to treatment with one or more of (i) a STING agonist; (ii) an Immune Checkpoint Blockade (ICB) agent; and (iii) an interferon gamma signaling agonist. Other cancer cells, e.g., certain tumor cells, possess low levels of STING and/or low levels of expression of one or more SPARCS genes, and that low levels of STING and/or low levels of expression of one or more SPARCS genes is a biomarker for susceptibility of cancer cells to treatment with at least one of a DNA methyltransferase inhibitor and an EZH2 inhibitor and, optionally, one or more of (i) a STING agonist; (ii) an Immune Checkpoint Blockade (ICB) agent; and (iii) an interferon gamma signaling agonist.

In one aspect, provided herein is a method for determining a treatment for cancer. The method comprises: (i) obtaining a biological sample obtained from a subject having cancer; (ii) determining the level of Stimulator of IFN Genes (STING); and (iii) selecting a therapy based on the level of STING.

In some embodiments, the therapy is selected from at least one of: (i) a STING agonist; (ii) an Immune Checkpoint Blockade (ICB) agent; and (iii) an interferon gamma signaling agonist; if the level of STING is above a reference value. In some embodiments, the therapy comprises a STING agonist and an Immune Checkpoint Blockade (ICB) agent. In some embodiments, the therapy comprises a STING agonist and an interferon gamma signaling agonist.

In some embodiments, the therapy is selected from at least one of a DNA methyltransferase inhibitor and an EZH2 inhibitor if the level of STING is below a reference value. In some embodiments, the therapy further comprises at least one of: (i) a STING agonist; (ii) an Immune Checkpoint Blockade (ICB) agent; and (iii) an interferon gamma signaling agonist.

In another aspect, provided herein is a method for treating cancer. The method comprises: (i) obtaining a biological sample obtained from a subject having cancer; (ii) determining the level of Stimulator of IFN Genes (STING); (iii) selecting a therapy based on the level of STING; and (iv) administering the therapy to the subject.

In some embodiments, the therapy is selected from at least one of: (i) a STING agonist; (ii) an Immune Checkpoint Blockade (ICB) agent; and (iii) an interferon gamma signaling agonist; if the level of STING is above a reference value. In some embodiments, the therapy comprises a STING agonist and an Immune Checkpoint Blockade (ICB) agent. In some embodiments, the therapy comprises a STING agonist and an interferon gamma signaling agonist.

In some embodiments, the therapy is selected from at least one of a DNA methyltransferase inhibitor and an EZH2 inhibitor if the level of STING is below a reference value. In some embodiments, the therapy further comprises at least one of: (i) a STING agonist; (ii) an Immune Checkpoint Blockade (ICB) agent; and (iii) an interferon gamma signaling agonist.

In yet another aspect, provided herein is a method of treating a subject having KRAS lung cancer. The method comprises: obtaining a biopsy sample from the subject; determining if the sample has KRAS;LKB1+ or KRAS;LKB1 mutant cancer cells; administering a STING agonist if the cancer cells are KRAS;LKB1+ cancer cells; and administering a STING agonist and at least one of a DNA methyltransferase inhibitor and an EZH2 inhibitor if the cancer cells are LKB1 mutant cancer cells.

In some embodiments, the method further comprises administering one or both of: (i) an Immune Checkpoint Blockade (ICB) agent; and (ii) an interferon gamma signaling agonist.

In yet another aspect, provided herein is a method of treating a subject having breast cancer. The method comprises: obtaining a biopsy sample from the subject comprising breast cancer cells; determining if the breast cancer cells in the sample are triple negative, HER2+, or luminal B breast cancer cells; administering a STING agonist if the breast cancer cells are triple negative, HER2+, or luminal B breast cancer cells; and administering a STING agonist and at least one of a DNA methyltransferase inhibitor and an EZH2 inhibitor if the breast cancer cells are not triple negative, HER2+, or luminal B breast cancer cells.

In some embodiments, the method further comprises administering one or both of: (i) an Immune Checkpoint Blockade (ICB) agent; and (ii) an interferon gamma signaling agonist.

In yet another aspect, provided herein is a method for determining a treatment for cancer. The method comprises: (i) obtaining a biological sample obtained from a subject having cancer; (ii) determining the level of one or more SPARCS genes; and (iii) selecting a therapy based on the level of the one or more SPARCS genes.

In some embodiments, the therapy is selected from at least one of: (i) a STING agonist; (ii) an Immune Checkpoint Blockade (ICB) agent; and (iii) an interferon gamma signaling agonist; if the level of one or more SPARCS genes is above a reference value. In some embodiments, the therapy comprises a STING agonist and an Immune Checkpoint Blockade (ICB) agent. In some embodiments, the therapy comprises a STING agonist and an interferon gamma signaling agonist.

In some embodiments, the therapy is selected from at least one of a DNA methyltransferase inhibitor and an EZH2 inhibitor if the level of one or more SPARCS genes is below a reference value. In some embodiments, the therapy further comprises at least one of: (i) a STING agonist; (ii) an Immune Checkpoint Blockade (ICB) agent; and (iii) an interferon gamma signaling agonist.

In yet another aspect, provided herein is a method for treating cancer. The method comprises: (i) obtaining a biological sample obtained from a subject having cancer; (ii) determining the level of one or more SPARCS genes; (iii) selecting a therapy based on the level of the one or more SPARCS genes; and (iv) administering the therapy to the subject.

In some embodiments, the therapy is selected from at least one of: (i) a STING agonist; (ii) an Immune Checkpoint Blockade (ICB) agent; and (iii) an interferon gamma signaling agonist; if the level of one or more SPARCS genes is above a reference value. In some embodiments, the therapy comprises a STING agonist and an Immune Checkpoint Blockade (ICB) agent. In some embodiments, the therapy comprises a STING agonist and an interferon gamma signaling agonist.

In some embodiments, the therapy is selected from at least one of a DNA methyltransferase inhibitor and an EZH2 inhibitor if the level of one or more SPARCS genes is below a reference value. In some embodiments, the therapy further comprises at least one of: (i) a STING agonist; (ii) an Immune Checkpoint Blockade (ICB) agent; and (iii) an interferon gamma signaling agonist.

In some embodiments, the level of STING is the level of STING mRNA. In some embodiments, the level of STING is the level of STING protein.

In some embodiments, the level of the one or more SPARCS genes is the level of mRNA. In some embodiments, the level of the one or more SPARCS genes is the level of protein.

In some embodiments, the one or more SPARCS genes are selected from TRIM22, TRIM38, IL32, SPATS2L, EPHA3, HERC3, ADAM19, SERPINB9, IFI44L, F3, BEND6, AIG1, MSRB2, TNFRSF9, and ANTXR1.

In some embodiments, the biological sample is a biopsy sample.

In some embodiments, the cancer is breast cancer, lung cancer, or kidney cancer.

In some embodiments, the STING agonist is selected from SB 11285, MK-1454, or ADU-S100.

In some embodiments, the Immune Checkpoint Blockade (ICB) agent is selected from anti-PD1, anti-PD-L1, or anti-CTLA-4.

In some embodiments, the interferon gamma signaling agonist is selected from poly I:C or PTPN2 inhibitors.

In some embodiments, the DNA methyltransferase inhibitor or EZH2 inhibitor is GSK126, azacitidine, or decitabine.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 1A-1L show discovery of an IFN-inducible subclass of ERVs. FIG. 1A: Immunoblot of pTBK1, TBK1, IKKε, pIRF3, pERK, ERK, pAKT, AKT and tubulin levels in H69 and H69M cells after 24 or 72 h culture. FIG. 1B: Log-2 fold change cytokine/chemokine differences between H69M/H69 CM. FIG. 1C: H&E and pTBK1 IHC of a patient-derived SCLC brain metastasis. Scale bar indicates 20 μm. FIG. 1D: Isotype control versus PD-L1 or CD44 surface expression on H69 and H69M cells±200 ng/mL 24 h IFNγ stimulation (representative of n=3 biological replicates). FIG. 1E: Immunoblot of pTBK1, TBK1, pERK, ERK, pAKT, AKT and β-actin levels in H69, H69M, H69M-PD-L1$^{low}$, and H69M-PD-L1$^{high}$ cells. FIG. 1F: Log-2 fold change cytokine/chemokines differences between H69M-PD-L1$^{high}$ or H69M-PD-L1$^{low}$/H69 CM. FIG. 1G: qRT-PCR of ERVs in H69M-PD-L1$^{high}$ normalized to H69M-PD-L1$^{low}$ cells, averaged from three independent experiments. FIG. 1H: TRIM22 promoter and antisense orientation of MLT1C49 in the 3'UTR. FIG. 1I: Overlap of 3'UTR antisense ERVs with H69M upregulated genes (log-2 fold change relative to H69>2). FIG. 1J: Immunoblot of STING, MAVS, pTBK1, TBK1, pIRF3, IRF3, E-Cadherin, Vimentin and β-actin levels in H69M cells after CRISPR mediated deletion of MAVS and/or STING. FIG. 1K: Log-2 fold change cytokine/chemokine differences in CM from H69M cells after CRISPR mediated deletion of MAVS and/or STING compared to sgCTRL (Scramble). FIG. 1L: CXCL10 Luminex absolute levels (pg/mL) in Scramble, STING KO, MAVS KO and double KO (dKO) H69M cells. Mean±SD of duplicate samples shown. *p<0.05; p<0.005; *p<0.001; n.s., not significant (Student's t test).

FIG. 2A: Isotype control versus PD-L1 or CD44 surface expression on H69AR cells±200 ng/mL 24 h IFNγ stimulation (representative of n=3 biological replicates). FIG. 2N: Photograph of representative excised tumors from sgCTRL and sgMAVS H69AR cells and tumor volumes measurements after 38 days of injection. Each data point represents mean±s.e.m. tumor volumes (n=6 in sgCTRL group (top line) and n=6 in sgMAVS group (bottom line); Two-way ANOVA). $*p<0.05$; $p<0.005$; $*p<0.001$; n.s., not significant (Student's t test).

FIGS. 3A-3E show SPARCS expression across cancers. FIG. 3A: ssGSEA of SPARCS signature across TCGA (n=3602 tumors) and significantly associated gene sets grouped based on biological annotations. IC=information coefficient. FDR=false discovery rate. FIG. 3B: Intersection of top 1000 genes co-regulated with SPARCS in TCGA and CCLE datasets. MHC class I pathway genes in top 40 highlighted in red, EMT related genes in blue and immune evasion markers in green. FIG. 3C: Distribution of high versus low SPARCS expression by TCGA cancer histology. FIG. 3D: Immunoblot of AXL, MET, Vimentin, STING, MAVS and β-actin levels in cell lines with high, intermediate, or low SPARCS signature expression after 72 h culture. FIG. 3E: qRT-PCR of MLT1C49, CXCL10, PD-L1 and CD44 in SPARCS$^{high}$ (H196, HCC44, A498, 786-0, A704, MDA-MB-231, HCC1143, 769P, and MDA-MB-468) and SPARCS$^{low}$ (CAKI-2, H522, T47D, MDA-MB-453, H1436, H2081, and H69) cell lines±IFNγ 10 min pulse–24 h chase. Mean±SD of triplicate samples shown (Mann Whitney U test).

FIGS. 4A-4H show that SPARCS expression is associated with adaptive and immune suppressive signatures. FIG. 4A: ssGSEA of immune signatures in SPARCS$^{high}$ and SPARCS$^{low}$ primary tumors across TCGA (n=3602 tumors) and ranked based on q value significance. FIG. 4B: Scatterplot representing difference in SPARCS$^{high}$ vs SPARCS$^{low}$ tumors of ssGSEA of immune signatures. $-\log_{10}$ (FDR q-value) for a Student's t test with equal variances for enrichment of ssGSEA of immune signatures in SPARCS$^{high}$ vs SPARCS$^{low}$ is shown on the y-axis. Signatures more highly represented in SPARCS$^{high}$ are shown on the right, while those more commonly represented in SPARCS$^{low}$ are shown on the left. FIG. 4C: q value significances of ssGSEA of immune signatures in SPARCS$^{high}$ vs SPARCS$^{low}$ primary tumors across TCGA. FIG. 4D: TCGA RPKM values of CXCL10 and CCL2 in primary tumors grouped in SPARCS$^{high}$ (n=50) and SPARCS$^{low}$ (n=50), from left to right in each graph.

FIG. 4E: Multiplexed immunofluorescence staining of Cytokeratin, CD8 and CD4 in KRAS mutant NSCLC human specimens used to generate PDOTS. Genomic features are shown. Scale bar indicates 100 µm. FIG. 4F: Cytokine/chemokine heatmap for NSCLC PDOTS treated with Nivolumab (100 µg/mL), IFNγ (200 ng/mL), or Nivolumab+IFNγ plotted as Log-2 FC relative to control. FIG. 4G: CXCL10 Luminex absolute levels (pg/mL) after treatment with control, Nivolumab, IFNγ, or Nivolumab+IFNγ, from left to right in each graph. Mean±SD of duplicate samples shown. FIG. 4H: Phase contrast images and viability quantification analysis of NSCLC PDOTS performed on Day 6 following treatment with Nivolumab (100 µg/mL), IFNγ (200 ng/mL) or Nivolumab+IFNγ Scale bar indicates 100 µm. $*p<0.05$; $p<0.005$; $*p<0.001$; n.s., not significant (Student's t test).

FIG. 5A: Schematic of H69M and H69AR subclone generation. FIG. 5B: Heatmap showing top signatures differentially expressed in H69M versus H69 cells. FIG. 5C: Cytokine antibody arrays of 72 h CM from H69 and H69M cells. FIG. 5D: Cytokine antibody arrays of 72 h CM from H187, H345, H524 (neuroendocrine phenotype) and H841, SHP77 (mesenchymal phenotype). FIG. 5E: Immunoblot of pTBK1, TBK1, IKKε, pIRF3, IRF3 pERK, ERK, pAKT, AKT and tubulin levels in H841 and SHP77 cells versus H187, H345, and H524 cells after 24 or 72 h in culture. FIG. 5F: Representative IHC image of weak and moderate 5172 pTBK1 expression of hepatic tumor nodules obtained from a GEM model of SCLC. FIG. 5G: Representative low- and high-magnification images of S172 pTBK1 heterogenous staining in metastatic lung nodules from SCLC GEMM. FIG. 5H: H&E and S172 pTBK1 IHC of representative sections from lung and liver tumor nodules from another SCLC GEMM. Scale bars indicates 100 µm or 20 µm.

FIG. 6A: Schematics of co-culture of H69, H69M and H69AR spheroids with CFSE labeled Jurkat T cells or THP1 monocytes. FIGS. 6B and 6C: 4× and 10× phase-contrast and fluorescent imaging of H69 and H69AR in 3D microfluidic device co-cultured with CFSE labeled Jurkat T cells and THP1 monocytes. Fluorescence staining shows CFSE labeled Jurkat and THP1 cell migration into the collagen. Scale bars indicates 500 µm (4× images) or 100 µm (10× images). FIG. 6D: 10× phase-contrast and fluorescent imaging of H69M in 3D microfluidic device co-cultured with CFSE labeled THP1 monocytes or Jurkat T cells. Fluorescence staining shows CFSE THP1 and Jurkat cell migration into the collagen. Scale bar indicates 100 µm. FIG. 6E: Quantification of fluorescence intensity of migrated immune cells in collagen with H69, H69M and H69AR. Mean±SD of triplicate samples shown. $*p<0.05$; $p<0.005$; $*p<0.001$ (Student's t test).

FIG. 7A: Schematics of PD-L1 cell sorting in H69M cells. FIG. 7B: Sorting of H69M-PD-L1$^{high}$ and PD-L$^{low}$ subclones (phase contrast images 10×). Scale bar indicates 100 µm. FIG. 7C: Phase contrast images of H69M-PD-L1 high cells at different passages. Scale bar indicates 100 FIG. 7D: OncoPanel Assay of 300 cancer genes and 113 introns across 35 genes for mutation and copy number detection. Mutation and copy number profiles showed no significant differences. FIG. 7E: Immunoblot of STING, MAVS and β-actin levels in H69, H69AR and H69M subclones. FIG. 7F: 10× phase-contrast and fluorescent imaging of H69M Scramble or STING/MAVS KO cells in 3D microfluidic device co-cultured with CFSE labeled THP1 monocytes or Jurkat T cells. Fluorescence staining shows CFSE THP1 and Jurkat cell migration into the collagen. Scale bar indicates 100 μm. FIG. 7G: Quantification of fluorescence intensity of migrated immune cells in collagen with H69M Scramble or STING/MAVS KO cells. Mean±SD of triplicate samples shown. FIG. 7H: Phase contrast images of H69M cells after CRISPR mediated deletion of MAVS and/or STING. Scale bar indicates 100 FIG. 7I: qRT-PCR of E-Cadherin and Vimentin in H69M cells after CRISPR mediated deletion of MAVS and/or STING. Mean±SD of duplicate samples shown. Scramble, STING KO, MAVS KO, and dKO are shown from left to right for each of E-Cadherin and Vimentin. $*p<0.05$; $p<0.005$; $*p<0.001$ (Student's t test).

FIG. 8A: qRT-PCR of ERV panel in H69, H69M, H69M-PD-L$^{high}$, H69M-PD-L$^{low}$ and H69AR cells, shown from left to right for each ERV, averaged over three independent experiments. FIG. 8B: qRT-PCR of TRIM22 and PD-L1 H69 and H69AR cells±200 ng/mL IFNγ pulse–24 h chase. Control, IFNγ pulse 10 min, IFNγ pulse 30 min, IFNγ pulse 1 hour, and IFN' pulse 3 hour are shown from left to right in each cell type in each graph. Mean±SD of triplicate samples shown. FIG. 8C: Log-2-fold change cytokine/chemokine differences between IFNγ pulsed H69AR/H69 CM. FIG. 8D: ATAC-seq insertion tracks of H69 and H69AR cells around SPARCS genes, CXCL10 and CCL2. Differentially accessible regions indicated with arrows. SPARCS genes highlighted in red. $*p<0.05$; $p<0.005$; $*p<0.001$ (Student's t test).

FIG. 9A: qRT-PCR of 12 different SPARCS in H69 and H69AR cells (from left to right for each gene)±200 ng/mL IFNγ pulse–24 h chase. Mean±SD of triplicate samples shown. FIG. 9B: qRT-PCR of 12 different SPARCS in EZH2i treated H69 cells exposed to IFNγ 24 hours. Mean±SD of triplicate samples shown. For each SPARCS gene, DMSO treated cells are shown on the left and GSK126 treated cells are shown on the right. FIG. 9C: Sense/antisense transcript quantification of MLT1C49, MLT1A, MLT1J and/3-actin in H69AR cells+10 min IFNγ pulse –24 h chase. Mean±SD of triplicate samples shown. FIG. 9D: Immunoblot of pTBK1, pSTAT1 and β-actin levels in H69AR cells±200 ng/mL IFNγ 10 min pulse followed by 1, 2, 3, 4, 5, 6 days' chase. FIG. 9E: qRT-PCR of MLT1A and MLT1J in H69AR cells±10 min IFN-γ pulse–24 h chase. In each graph, for control and IFN-γ pulsed cells, days 1, 3, and 5 chase are shown from left to right. Mean±SD of triplicate samples shown. FIG. 9F: qRT-PCR of MLT1C49, IFNα, IFNβ and IFNγ in H69AR cells 72 h following Poly(I:C) transfection. For each of control and poly (I:C) transfection, MLT1C49, IFNα, IFNβ and IFNγ in H69AR cells are shown from left to right. Mean±SD of triplicate samples shown. FIG. 9G: qRT-PCR of MLT1C49 and MLT1A in H69AR cells±10 min IFN-α or IFN-β pulse with indicated chase. Mean±SD of triplicate samples shown. $*p<0.05$; $p<0.005$; $*p<0.001$; n.s., not significant (Student's t test).

FIG. 10A: Schematic of H69AR conditioned media experiment. FIG. 10B: Immunoblot of pTBK1, TBK1, pSTAT1, STAT1 and β-actin levels in H69AR cells±10 min IFN-γ pulsed CM for 48 and 72 h. FIG. 10C: qRT-PCR of IFN-β (left) and CXCL10 (right) from 48 h CM treated cells. Mean±SD of triplicate samples shown. FIG. 10D: qRT-PCR of ERVs from same conditions (for each of control and IFN-γ pulsed CM, MLT1C49, MLT1A, and MLT1J from left to right). Mean±SD of triplicate samples shown. FIG. 10E: Immunoblot of pSTAT1, STAT1 and β-actin levels in H69AR cells±200 ng/mL IFNγ 10 min pulse followed by 24 h chase in media with DMSO, Ruxolitinib (100 nM) or MRT67307 μM). Figure qRT-PCR of CXCL10, MLT1C49, MLT1A and MLT1J in H69AR cells+10 min IFNγ–24 h chase in media with DMSO, MRT67307 (μM) or Ruxolitinib (100 nM). For each of control and IFN-γ pulsed cells, DMSO, MRT67307 and Ruxolitinib are shown from left to right. Mean±SD of triplicate samples shown. FIG. 10G: CXCL10 ELISA in H69AR cells+10 min IFNγ–24 h chase in media with DMSO, MRT67307 (μM) or Ruxolitinib (100 nM). Mean±SD of triplicate samples shown. For each of control and IFN-γ pulsed cells, DMSO, MRT67307 and Ruxolitinib are shown from left to right. FIG. 10H: Immunoblot of MAVS, STING and β-actin levels in H69AR cells after CRISPR mediated deletion of MAVS and/or STING. FIG. 10I: qRT-PCR of IFN/3 and IFNγ in sgCTRL (on left in each graph) and sgMAVS-H69AR cells (on right in each graph) 72 h following Poly(I:C) transfection. Mean±SD of triplicate samples shown. $*p<0.05$; $p<0.005$; $*p<0.001$; n.s., not significant (Student's t test).

FIG. 11B: ssGSEA of a control 3'UTR antisense ERV gene set across TCGA (n=3602 tumors) reveals lack of correlation with top SPARCS transcriptomic features.

FIGS. 12A-12D show that SPARCS association with multiple markers on chromosome 3p, MHC class I induction, mesenchymal state and EZH2 and SWI/SNF loss across TCGA and CCLE. FIG. 12A: Heatmap showing top 20 genomic alterations associated with SPARCS signature across TCGA data set (n=3602 tumors). FIG. 12B: Heatmap showing top 20 genomic alterations associated with SPARCS signature across CCLE data set (n=585 cell lines). FIG. 12C: Heatmap showing top and bottom 1000 genes with expression associated with the SPARCS signature across TCGA RNA-seq datasets (n=3602 tumors). Highlighted are the positions of specific genes positively and negatively associated with the SPARCS signature. FIG. 12D: Heatmap showing top and bottom 1000 genes with expression associated with the SPARCS signature across CCLE RNA-seq datasets (n=585 cell lines). Highlighted are the positions of specific genes positively and negatively associated with the SPARCS signature.

FIG. 13A: CCLE RPKM values of mesenchymal and epigenetic associated genes and dsRNA/dsDNA sensors in cell lines grouped in SPARCS$^{high}$ (n=50) and SPARCS$^{low}$ (n=50). FIG. 13B: Phase contrast images of SPARCS$^{high}$ and SPARCS$^{low}$ cell lines. Scale bar indicates 100 μm. $*p<0.05$; $p<0.005$; $*$ $p<0.001$; n.s., not significant (Student's t test).

FIG. 14A: Isotype control versus PD-L1 or CD44 surface expression on H196 (SPARCS$^{high}$) and T47D (SPARCS$^{low}$) cell lines±200 ng/mL 24 h IFNγ stimulation. FIG. 14B: Classification of TCGA primary tumors based on SPARCS signature score (ssGSEA) into SPARCS$^{high}$ (N=2225) and SPARCS$^{low}$ groups (N=1377). FIG. 14C: Cytokine/chemokines heatmap for human NSCLC PDOTS treated with Nivolumab (100 µg/mL), Poly (I:C), or Nivolumab+Poly (I:C) plotted as Log-2 FC relative to control. FIG. 14D: CXCL10 Luminex absolute levels (pg/mL) in human NSCLC PDOTS treated with control, Nivolumab (100 µg/mL), Poly (I:C), or Nivolumab+Poly (I:C), from left to right. Mean±SD of duplicate samples shown. FIG. 14E: Phase contrast images and viability quantification analysis of NSCLC PDOTS performed on Day 6 following treatment with Nivolumab (100 pg/mL), Poly (I:C), or Nivolumab+Poly (I:C). Scale bar indicates 100 µm. *p<0.05; p<0.005; *p<0.001; n.s., not significant (Student's t test).

FIGS. 15A and 15B. FIG. 15A: qRT-PCR of STING in KL and KP cell lines. FIG. 15B: Immunoblot of the indicated proteins in KL and KP cell lines. * indicates tcell lines with p53 mutation in addition to LKB1 mutation.

FIGS. 16A to 16C. FIG. 16A: Immunoblot of the indicated proteins in KL cell lines transduced with the indicated vector. FIG. 16B: Correlation between STING and DNMT1 expression in KL cell lines. FIG. 16C: Immunoblot of the indicated proteins in KL cell lines transduced with the indicated vector with or without 100 nM 5-aza-2'-deoxycytidine (DAC) treatment for 7 days.

FIG. 17A: Immunoblot of the indicated proteins in KL cell lines transduced with the indicated vector with or without 1 ug/ml poly(dA:dT) or poly(I:C) treatment for 3 h. FIG. 17B: ELISA of human CXCL10 levels in conditioned medium derived from KL cell lines transduced with the indicated vector with or without 1 ug/ml poly(dA:dT) or poly(I:C) treatment for 24 h.

FIG. 19 shows that EZH2 pharmacological inhibition induces STING protein expression in H69 cell line. Immunoblot of STING, histone H3K27me3 and β-actin levels in H69 cells after GSK126 (EZH2 inhibitor) treatment at the indicated concentrations and for the indicated number of days.

FIGS. 20A and 20B. Increased STING expression in SPARCS$^{high}$ cell lines. Figure CCLE RPKM values of STING gene expression in cancer cell lines grouped in SPARCS$^{high}$ (n=50) and SPARCS$^{low}$ (n=50). FIG. 20B: Immunoblot of STING and β-actin levels in lung, breast, and kidney cancer cell lines with high, intermediate and low SPARCS signature expression.

FIG. 22A shows increased STING expression in TNBC and luminal B breast cancer cell lines via western blot. FIG. 22B shows the genotypes of the cell lines tested in FIGS. 22A and 22C. FIG. 22C shows increased STING expression in TNBC and luminal B breast cancer cell lines via western blot. FIG. 22D shows increased CXCL10 production by TNBC cell lines treated with AduroS100 relative to controls.

DETAILED DESCRIPTION OF INVENTION

Figure 1D:
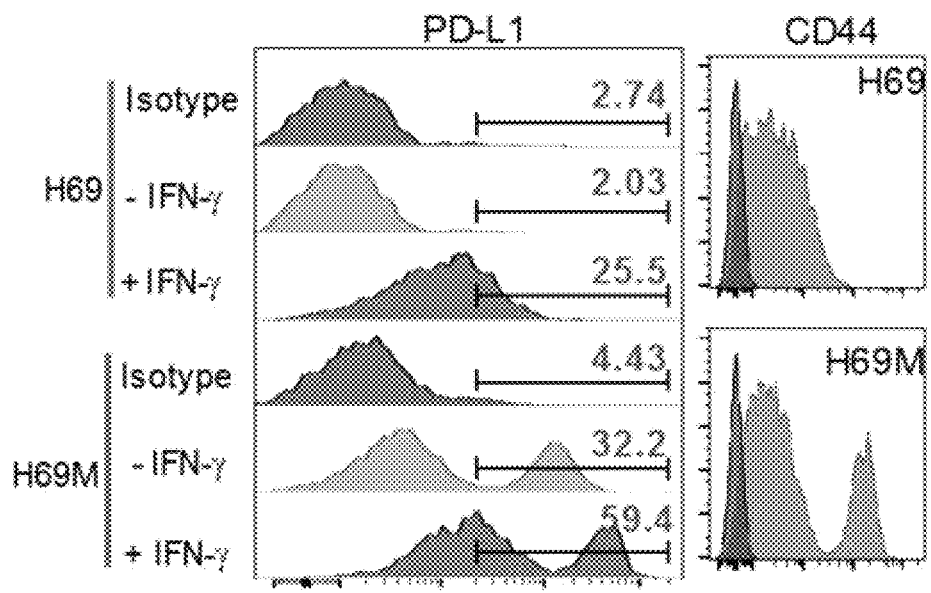

The present disclosure is based on the surprising discovery that the level of STING and/or one or more SPARCS genes can be used as a biomarker to determine an effective cancer therapy. Certain cancer cells, e.g., certain tumor cells, possess high levels of STING and that said cancer cells are susceptible to treatment with STING agonists. STING (Stimulator of interferon genes), encoded by TMEM173, has emerged as a critical regulator of the innate immune response to cytoplasmic double stranded DNA (dsDNA), and has been recognized to play an increasingly important role in cancer pathogenesis and cancer immunotherapy. STING agonists, which, in some embodiments, are analogues of the specific cyclic dinucleotide (CDN) that directly activates STING in response to cytoplasmic dsDNA, have entered the clinic in phase 1 trials both alone and in combination with immune checkpoint blockade.

Surprisingly, it has been demonstrated herein that STING levels are tightly regulated in cancer cells, and that specific cell states are associated with STING upregulation or lack thereof. Furthermore, it has been discovered that the genomic locus encoding STING (TMEM173) is epigenetically regulated, and that STING expression can be induced by DNMT and EZH2 inhibition. These findings suggest that STING agonists would be most effectively deployed in specific tumor contexts with high STING levels, and that treatment with specific epigenetic inhibitors are likely to induce STING and promote sensitivity in tumors with otherwise low STING levels. Moreover, it has been found that elevated levels of STING are associated with elevated levels of one or more SPARCS genes. Accordingly, presented herein are methods for treating cancer having elevated levels of one or more SPARCS genes with STING agonists.

Elevated STING levels and/or elevated levels of one or more SPARCS genes have surprisingly been found to be associated with elevated levels of immune checkpoint proteins, e.g., PD-L1. Accordingly, presented herein are methods for treating cancer having elevated STING levels and/or elevated levels of one or more SPARCS genes with an Immune Checkpoint Blockade (ICB) agent.

Elevated STING levels and/or elevated levels of one or more SPARCS genes have surprisingly been found to be associated with elevated levels of interferon gamma. Accordingly, presented herein are methods for treating cancer having elevated STING levels and/or elevated levels of one or more SPARCS genes with an interferon gamma signaling agonist.

Moreover, it has been surprisingly found that expression of STING and/or expression of one or more SPARCS genes is inhibited by DNA methyltransferase and/or PRC2, e.g., EZH2. Accordingly, presented herein are methods for treating cancer cells having low levels of STING and/or low levels of one or more SPARCS genes with at least one of a DNA methyltransferase inhibitor and an EZH2 inhibitor and, optionally, one or more of (i) a STING agonist; (ii) an Immune Checkpoint Blockade (ICB) agent; and (iii) an interferon gamma signaling agonist.

STING Biomarker

Stimulator of interferon genes (STING) is a ubiquitously produced transmembrane protein encoded by the TMEM173 gene. The longest isoform of STING has 379 amino acids. STING plays a key role as a mediator of innate immune signaling. It induces the innate immune signaling in response to the detection of bacterial and viral DNA in the cytoplasm, and promotes the production of type I interferon (IFN-alpha and IFN-beta). Multiple studies have involved STING in the development of conditions including infectious diseases and certain cancers.

The STING amino acid sequence is:

```
                                            (SEQ ID NO: 1)
MPHSSLHPSIPCPRGHGAQKAALVLLSACLVTLWGLGEPPEHTLRYLVLH

LASLQLGLLLNGVCSLAEELRHIHSRYRGSYWRTVRACLGCPLRRGALLL

LSIYFYYSLPNAVGPPFTWMLALLGLSQALNILLGLKGLAPAEISAVCEK

GNFNVAHGLAWSYYIGYLRLILPELQARIRTYNQHYNNLLRGAVSQRLYI

LLPLDCGVPDNLSMADPNIRFLDKLPQQTGDHAGIKDRVYSNSIYELLEN

GQRAGTCVLEYATPLQTLFAMSQYSQAGFSREDRLEQAKLFCRTLEDILA

DAPESQNNCRLIAYQEPADDSSFSLSQEVLRHLRQEEKEEVTVGSLKTSA

VPSTSTMSQEPELLISGMEKPLPLRTDFS
```

The STING amino acid sequence has GenBank Accession Number NP_938023.1. The STING nucleotide sequence has GenBank Accession Number NM_198282.3.

In some embodiments, STING is upregulated (or is elevated, as the terms are used interchangeably) in a biological sample relative to controls. As used herein, an upregulated or elevated level includes a level that is above a control level or reference value as defined herein. An upregulated or elevated level may be, for example, 1%, 5%, 10%, 20%, 30%, 40%, 50%, 60%, 70%, 80%, 90%, 100%, 150%, 200%, 300%, 400%, 500% or more above a control level or reference value as defined herein.

In some embodiments, a cancer, e.g., a tumor or cancer cell, with upregulated STING levels is susceptible to (i) a STING agonist; (ii) an Immune Checkpoint Blockade (ICB) agent; and/or (iii) an interferon gamma signaling agonist.

In some embodiments, STING is downregulated in a biological sample (or is reduced, as the terms are used interchangeably) relative to controls. As used herein, an downregulated or reduced level includes a level that is below a control level or reference value as defined herein. An downregulated or reduced level may be, for example, 1%, 5%, 10%, 20%, 30%, 40%, 50%, 60%, 70%, 80%, 90%, 100%, 150%, 200%, 300%, 400%, 500% or more below a control level or reference value as defined herein. In some embodiments, STING levels are unchanged relative to controls.

In some embodiments, a cancer, e.g., a tumor or cancer cell, with downregulated or unchanged STING levels is susceptible to one or more of a DNA methyltransferase inhibitor and an EZH2 inhibitor, and optionally (i) a STING agonist; (ii) an Immune Checkpoint Blockade (ICB) agent; and/or (iii) an interferon gamma signaling agonist.

In some embodiments, a level of mRNA is upregulated. In some embodiments, a protein level is upregulated.

SPARCS Biomarkers

As is described in Example 1, Stimulated 3 Prime Antisense Retroviral Coding Sequences (SPARCS) genes were identified as genes upregulated in cancer cells having undergone the epithelial-mesenchymal transition and having an endogenous retrovirus in the 3' UTR. These genes are interferon-inducible genes silenced by EZH2.

In some embodiments, one or more SPARCS genes are selected from TRIM22, TRIM38, IL32, SPATS2L, EPHA3, HERC3, ADAM19, SERPINB9, IFI44L, F3, BEND6, AIG1, MSRB2, TNFRSF9, and ANTXR1. The GenBank Accession Nos. for the SPARCS genes are shown in Table 1 and Table 2.

In some embodiments, one or more SPARCS genes are upregulated in a biological sample (or is elevated, as the terms are used interchangeably) relative to controls. As used herein, an upregulated or elevated level includes a level that is above a control level or reference value as defined herein. An upregulated or elevated level may be, for example, 1%, 5%, 10%, 20%, 30%, 40%, 50%, 60%, 70%, 80%, 90%, 100%, 150%, 200%, 300%, 400%, 500% or more above a control level or reference value as defined herein.

In some embodiments, the level of 1, 2, 3, 4, 5, 6, 7, 8, 9, 10, 11, 12, 13, or 14 SPARCS genes is upregulated. In some embodiments, the level of all 15 SPARCS genes is upregulated.

In some embodiments, a cancer, e.g., a tumor or cancer cell, with upregulated SPARCS gene levels is susceptible to (i) a STING agonist; (ii) an Immune Checkpoint Blockade (ICB) agent; and/or (iii) an interferon gamma signaling agonist.

In some embodiments, one or more SPARCS genes are downregulated in a biological sample (or is reduced, as the terms are used interchangeably) relative to controls. As used herein, an downregulated or reduced level includes a level that is below a control level or reference value as defined herein. An downregulated or reduced level may be, for example, 1%, 5%, 10%, 20%, 30%, 40%, 50%, 60%, 70%, 80%, 90%, 100%, 150%, 200%, 300%, 400%, 500% or more below a control level or reference value as defined herein.

In some embodiments, the level of 1, 2, 3, 4, 5, 6, 7, 8, 9, 10, 11, 12, 13, or 14 SPARCS genes is downregulated. In some embodiments, the level of all 15 SPARCS genes is downregulated.

In some embodiments, one or more SPARCS genes are unchanged relative to controls.

In some embodiments, a cancer, e.g., a tumor or cancer cell, with downregulated or unchanged SPARCS gene levels is susceptible to one or more of a DNA methyltransferase inhibitor and an EZH2 inhibitor, and optionally (i) a STING agonist; (ii) an Immune Checkpoint Blockade (ICB) agent; and/or (iii) an interferon gamma signaling agonist.

In some embodiments, a level of mRNA is upregulated. In some embodiments, a protein level is upregulated.

TABLE 1

| GenBank Accession Numbers for Protein Sequences ||
| Biomarker | GenBank Accession Number |
| --- | --- |
| TRIM 22 | NP_006065.2 |
| TRIM38 | NP_006346.1 |
| IL32 | NP_001295007.1 |
| SPATS2L | NP_001093892.1 |
| EPHA3 | NP_005224.2 |
| HERC3 | NP_055421.1 |

TABLE 1-continued

GenBank Accession Numbers for Protein Sequences

| Biomarker | GenBank Accession Number |
| --- | --- |
| ADAM19 | NP_150377.1 |
| SERPINB9 | NP_004146.1 |
| IFI44L | NP_006811.2 |
| F3 | NP_006811.2 |
| BEND6 | NP_689944.2 |
| AIG1 | NP_057192.2 |
| MSRB2 | NP_036360.3 |
| TNFRSF9 | NP_066961.2 |
| ANTXR1 | NP_115584.1 |

TABLE 2

GenBank Accession Numbers for Nucleotide Sequences

| Biomarker | GenBank Accession Number |
| --- | --- |
| TRIM 22 | NM_006074.4 |
| TRIM38 | NM_006355.4 |
| IL32 | NM_001308078.1 |
| SPATS2L | NM_001100422.1 |
| EPHA3 | NM_005233.5 |
| HERC3 | NM_014606.2 |
| ADAM19 | NM_033274.4 |
| SERPINB9 | NM_004155.5 |
| IFI44L | NM_006820.3 |
| F3 | NM_006820.3 |
| BEND6 | NM_152731.2 |
| AIG1 | NM_016108.3 |
| MSRB2 | NM_012228.3 |
| TNFRSF9 | NM_021138.3 |
| ANTXR1 | NM_032208.2 |

Detection Methods

The methods and devices of the invention may be protein or mRNA based. Examples of protein-based assays include immunoassays (also referred to herein as immune-based assays), immunohistochemistry, flow cytometry, mass spectrometry, Western blots, Western immunoblotting, multiplex bead-based assays, and assays involving aptamers (such as SOMAmer™ technology) and related affinity agents. Examples of mRNA-based assays include Northern analysis, quantitative RT-PCR, microarray hybridization, and multiplex bead-based assays. These assays generally and commonly detect and measure the level of the biomarker of interest. The level of the biomarker may then be compared to a control level. Control levels will be discussed in greater detail herein.

mRNA Detection

The art is familiar with various methods for analyzing mRNA levels. An exemplary quantitative RT-PCR assay may be carried out as follows: mRNA is extracted from cells in a biological sample (e.g., tumor cells) using the RNeasy kit (Qiagen). Total mRNA is used for subsequent reverse transcription using the SuperScript III First-Strand Synthesis SuperMix (Invitrogen) or the SuperScript VILO cDNA synthesis kit (Invitrogen). The RT reaction is used for quantitative PCR using SYBR Green PCR Master Mix and gene-specific primers, in triplicate, using an ABI 7300 Real Time PCR System.

Expression profiles of cells in a biological sample (e.g., tumor cells) can be carried out using an oligonucleotide microarray analysis. It is to be understood that such arrays may however also comprise positive and/or negative control markers such as housekeeping genes that can be used to determine if the array has been degraded and/or if the sample has been contaminated. The art is familiar with the construction of oligonucleotide arrays. See for example GeneChip Human Genome U133 Plus 2.0 Affymetrix expression array (Affymetrix). Other mRNA detection methods include multiplex detection assays well known in the art, e.g., xMAP® bead capture and detection (Luminex Corp., Austin, TX), and various oligonucleotide array assays (Illumina).

Subject. "Subject" means a mammal, such as a human, a nonhuman primate, a dog, a cat, a sheep, a horse, a cow, a pig or a goat. In an important embodiment, the mammal is a human. The subject as used herein can be an adult subject or a pediatric subject. In some embodiments, the subject has or is suspected of having cancer, e.g., any of the cancers described herein. In some embodiments, the subject is at elevated risk of developing cancer, for example, due to the presence of carcinogenic genetic mutations or exposure to carcinogens or radiation.

Biological sample. A "biological sample" from a subject can include any cellular, tissue, bone marrow, or blood sample from the subject. Any type of biological sample appropriate for conducting assays described herein can be compatible with aspects of the invention, as would be understood by one of ordinary skill in the art. In some embodiments, the biological sample is tumor tissue or a biopsy sample.

mRNA Detection Binding Partners mRNA detection binding partners include oligonucleotide or modified oligonucleotide (e.g. locked nucleic acid) probes that hybridize to a target mRNA. Probes may be designed against one or more of STING, TRIM22, TRIM38, IL32, SPATS2L, EPHA3, HERC3, ADAM19, SERPINB9, IFI44L, F3, BEND6, AIG1, MSRB2, TNFRSF9, and ANTXR1 or using the GenBank Accession Nos. in Table 1. Methods for designing and producing oligonucleotide probes are well known in the art (see, e.g., U.S. Pat. No. 8,036,835; Rimour et al. GoArrays: highly dynamic and efficient microarray probe design. Bioinformatics (2005) 21 (7): 1094-1103; and Wernersson et al. Probe selection for DNA microarrays using OligoWiz. Nat Protoc. 2007; 2(11): 2677-91).

Protein Detection

The art is familiar with various methods for analyzing protein levels. An exemplary immunoassay may be carried out as follows: A biological sample is applied to a substrate having bound to its surface biomarker-specific binding partners (i.e., immobilized biomarker-specific binding partners). The biomarker-specific binding partner (which may be referred to as a "capture ligand" because it functions to capture and immobilize the biomarker on the substrate) may be antibodies or antigen-binding antibody fragments such as Fab, F(ab)2, Fv, single chain antibodies, Fab and sFab fragments, F(ab')2, Fd fragments, scFv, and dAb fragments, although they are not so limited. Other binding partners are described herein. Biomarkers present in the biological sample bind to the capture ligands, and the substrate is washed to remove unbound material. The substrate is then exposed to soluble biomarker-specific binding partners (which may be identical to the binding partners used to immobilize the biomarker). The soluble biomarker-specific binding partners are allowed to bind to their respective biomarkers immobilized on the substrate, and then unbound material is washed away. The substrate is then exposed to a detectable binding partner of the soluble biomarker-specific binding partner. In one embodiment, the soluble biomarker-specific binding partner is an antibody having some or all of its Fc domain. Its detectable binding partner may be an anti-Fc domain antibody. As will be appreciated by those in the art, if more than one biomarker is being detected, the assay may be configured so that the soluble biomarker-specific binding partners are all antibodies of the same isotype. In this way, a single detectable binding partner, such as an antibody specific for the common isotype, may be used to bind to all of the soluble biomarker-specific binding partners bound to the substrate.

It is to be understood that the substrate may comprise capture ligands for one or more biomarkers, including two or more, three or more, four or more, five or more, etc. of the biomarkers provided by the invention.

In some instances, it may be preferable to measure biomarkers having the lowest detectable concentration. An example would be biomarkers having protein concentrations in the pg/ml range. In some instances, it may be preferable to measure, on a single substrate, biomarkers having protein concentrations that are in the same dynamic range (i.e., they are present in the biological sample in the same concentration range). Those of ordinary skill in the art will be able to devise multiplexing assays (i.e., assays that measure two or more markers) using the guidance provided herein and the knowledge in the art.

In some embodiments, the invention contemplates a substrate having a pre-determined amount of capture ligands for each biomarker. The pre-determined amount of capture ligand is may be based in part on prior measurements of biomarker levels in subjects that are STING high and STING low. The pre-determined amount of capture ligand is may be based in part on prior measurements of biomarker levels in subjects that are high for one or more SPARCS genes and low for one or more SPARCS genes. The assays may be designed such that if the subject is STING or SPARCS-positive, then one or more detectable signals appear, optionally on a biomarker-by-biomarker basis.

Other examples of protein detection methods include multiplexed immunoassays as described, e.g., in U.S. Pat. Nos. 6,939,720 and 8,148,171, and published US Patent Application No. 2008/0255766, and protein microarrays as described, e.g. in published US Patent Application No. 2009/0088329.

Protein Detection Binding Partners

Protein detection binding partners include biomarker-specific binding partners. In some embodiments, binding partners may be antibodies. As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')2, Fd fragments, Fv fragments, scFv, and dAb fragments) as well as complete antibodies. Methods for making antibodies and antigen-binding fragments are well known in the art (see, e.g. Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), WO2006/040153, WO2006/122786, and WO2003/002609).

In some embodiments, the binding partner for STING is the D2P2F Rabbit antibody 13647 from Cell Signaling Technology (cellsignal.com/products/primary-antibodies/sting-d2p2f-rabbit-mab/13647).

Binding partners also include proteins or peptides that bind to or interact with a target biomarker, e.g. through non-covalent bonding. For example, if the biomarker is a ligand, a binding partner may be a receptor for that ligand. In another example, if the biomarker is a receptor, a binding partner may be a ligand for that receptor. In yet another example, a binding partner may be a protein or peptide known to interact with a biomarker. Methods for producing proteins are well known in the art (see, e.g. Sambrook et al, "Molecular Cloning: A Laboratory Manual" (2nd Ed.), Cold Spring Harbor Laboratory Press (1989) and Lewin, "Genes IV", Oxford University Press, New York, (1990)) and can be used to produce binding partners such as ligands or receptors.

Binding partners also include aptamers and other related affinity agents. Aptamers include oligonucleic acid or peptide molecules that bind to a specific target molecule. Methods for producing aptamers to a target molecule are well known in the art (see, e.g., published US Patent Application No. 2009/0075834, U.S. Pat. Nos. 7,435,542, 7,807,351, and 7,239,742). Other examples of affinity agents include SOMAmer™ (Slow Off-rate Modified Aptamer, SomaLogic, Boulder, CO) modified nucleic acid-based protein binding reagents.

Binding partners also include any molecule capable of demonstrating selective binding to any one of the protein targets disclosed herein, e.g., peptoids (see, e.g., Reyna J Simon et al., "Peptoids: a modular approach to drug discovery" Proceedings of the National Academy of Sciences USA, (1992), 89(20), 9367-9371; U.S. Pat. No. 5,811,387; and M. Muralidhar Reddy et al., Identification of candidate IgG biomarkers for Alzheimer's disease via combinatorial library screening. Cell 144, 132-142, Jan. 7, 2011).

Detectable Labels

Detectable binding partners may be directly or indirectly detectable. A directly detectable binding partner may be labeled with a detectable label such as a fluorophore. An indirectly detectable binding partner may be labeled with a moiety that acts upon (e.g., an enzyme or a catalytic domain) or is acted upon (e.g., a substrate) by another moiety in order to generate a detectable signal. These various methods and moieties for detectable labeling are known in the art.

Controls

In some embodiments, methods provided herein involve measuring a level of a biomarker in a biological sample and comparing the biomarker level to a control level in order to characterize the level of STING or SPARCS expression in a subject. The control level is a level of the same biomarker in a control tissue, control subject, or a population of control subjects.

The "control" may be (or may be derived from) a normal subject (or normal subjects). Normal subjects, as used herein, refer to subjects that are apparently healthy and show no cancer symptoms. The control population may therefore be a population of normal subjects. In some embodiments, the control is from a normal healthy subject or subjects and is from the same tissue type as the biological sample.

In other instances, the control may be (or may be derived from) an ill subject (or ill subjects) that presents with one or more cancer without elevated or reduced STING or SPARCS expression.

In other instances, the control may be (or may be derived from) an ill subject (or ill subjects) that presents with one or more cancer with elevated or reduced STING or SPARCS expression.

In some embodiments, the control may be non-cancerous tissue from the subject being tested.

In still other instances, the control may be a biomarker level from a population of subjects regardless of whether they manifest or do not manifest cancer-like symptoms (e.g., a subset of the general population).

In any of the above embodiments, the control may be of the same tissue type as the biological sample.

It is to be understood however that the methods provided herein do not require that a control level be measured every time a subject is tested. In some embodiments, a control level be measured when a subject is tested. In other embodiments, it is contemplated that control levels of biomarkers are obtained and recorded and that any test level is compared to such a pre-determined level. Such pre-determined control levels may also be referred to herein as reference values which are discussed in greater detail herein.

Reference Values

A reference value describes a measurement value for a biomarker that aids in identifying a subject with a cancer susceptible to treatment with agents described herein.

The reference value may be calculated from control levels of each biomarker as measured from a control subject or population of subjects, or from non-cancerous tissue.

In some embodiments, the reference value for STING is the same as or 1%, 2%, 3%, 4%, 5%, 10%, 15%, 20%, 50%, 100%, or more above the control level. In some embodiments, the reference value for STING is 1%, 2%, 3%, 4%, or 5% below the control level. In some embodiments, the reference value for the one or more SPARCS genes is the same as or 1%, 2%, 3%, 4%, 5%, 10%, 15%, 20%, 50%, 100%, or more above the control level. In some embodiments, the reference value for the one or more SPARCS genes is 1%, 2%, 3%, 4%, or 5% below the control level.

The foregoing reference values are exemplary and it is to be understood that one of ordinary skill in the art is able to determine a control level based on the teachings provided herein and thereby establish new reference values that may be used in the methods provided herein.

Treatment

In some embodiments, a subject with a STING level or a level of one or more SPARCS genes above a reference value is treated with one or more of (i) a STING agonist; (ii) an Immune Checkpoint Blockade (ICB) agent; and (iii) an interferon gamma signaling agonist. In some embodiments, a subject with a STING level or a level of one or more SPARCS genes below a reference value is treated with one or more of a DNA methyltransferase inhibitor and an EZH2 inhibitor and optionally one or more of (i) a STING agonist; (ii) an Immune Checkpoint Blockade (ICB) agent; and (iii) an interferon gamma signaling agonist.

In some embodiments, the subject to be treated by the methods described herein is human. In some embodiments, a human subject who needs the treatment may be a human patient having, at risk for, or suspected of having cancer. A subject having cancer can be identified by routine medical examination, e.g., laboratory tests, functional tests, biopsy, CT scans, or ultrasounds. A subject suspected of having cancer might show one or more symptoms of the disorder. A subject at risk for cancer can be a subject having one or more of the risk factors for that disorder. For example, risk factors associated with cancer include (a) hereditary cancer, (b) age, and (c) family history of cancer.

Cancers include but are not limited to: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: non-small cell lung cancer (NSCLC), small cell lung cancer, bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), rectal, colon, colon-rectum, colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), head and neck cancer, meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertolI-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In some embodiments, the subject has KRAS lung cancer. In some embodiments, the subject has triple negative breast cancer, HER2+ breast cancer, or luminal B breast cancer. The data presented herein demonstrates that each of KRAS LKB1+ lung cancer, triple negative breast cancer, HER2+ breast cancer, and luminal B breast cancer are consistently associated with upregulated STING levels. As such, in some embodiments, a subject having KRAS LKB1+ lung cancer, triple negative breast cancer, HER2+ breast cancer, or luminal B breast cancer is treated with one or more of (i) a STING agonist; (ii) an Immune Checkpoint Blockade (ICB) agent; and (iii) an interferon gamma signaling agonist without measuring STING levels or the level of one or more SPARCs genes.

KRAS Lung Cancer

Non-small-cell lung cancer (NSCLC) is a heterogeneous disease, with multiple different oncogenic mutations. Approximately 25-30% of NSCLC patients present KRAS mutations, which confer poor prognosis and high risk of tumor recurrence. In the majority of cases, these KRAS mutations are missense mutations which introduce an amino acid substitution at position 12, 13, or 61 (e.g., an amino acid substitution at position 12, 13, or 61 of NCBI NP_004976.2). The result of these mutations is constitutive activation of KRAS signaling pathways. The role of KRAS mutations and their potential association with other common genetic lung cancer lesions (LKB1, P53) has recently been investigated in different cohorts of human lung adenocarcinomas using transcriptional, mutational, copy-number and proteomic data. These studies highlighted how LKB1 inactivation is significantly associated with KRAS mutations compared to P53 deletion and that co-occurrence of KRAS mutation with inactivation of LKB1 or P53 genes generates different tumor subsets with distinct biology, immune profiles, and therapeutic vulnerabilities. About half of NSCLCs with activating KRAS lesions also have deletions or inactivating mutations in the serine/threonine kinase 11 (LKB1) gene. Loss of LKB1 on a KRAS-mutant background may represent a significant source of heterogeneity contributing to poor response to therapy. LKB1 mutations associated with lung cancer are extensively characterized in the art. Exemplary LKB1 mutations can be found, for example, in Kaufman et al, Cancer Research, 2016, the entirety of which is incorporated herein by reference.

The genotype of lung cancer can be determined by means readily known to those of skill in the art for assessing the genotype and/or levels of the markers, e.g., KRAS, LKB1, and p53, as described, for example, in Sholl, (Transl Lung Cancer Res. 2017 6(5): 560-569) including but not limited to, determining the genomic sequence of marker, e.g., by DNA sequencing or allele specific PCR, determining expression of the marker, e.g., by northern analysis, quantative PCR, or microarray analysis, or determining protein levels of the marker, e.g., by western analysis, mass spectrometry, immunohistochemistry, ect.

Breast Cancer

Breast cancers can be classified at the molecular level based on their genes and proteins by dividing them into four main molecular subtypes: HER2-positive, luminal A, luminal B and triple-negative.

One in five invasive breast cancers is HER2-positive, making this one of the more common breast cancer subtypes in the United States. HER2-positive cancers are ER- and PR-negative and human epidermal growth factor receptor 2 (HER2)-positive. HER2-positive breast cancer cells carry excess copies of the HER2 gene, which makes HER2-protein receptors, found on breast cells.

Luminal A breast cancer is the most common subtype of breast cancer for every race and age. These tumors tend to be estrogen receptor (ER)-positive and progesterone receptor (PR)-positive and are typically slow growing.

Luminal B breast cancer includes tumors that are estrogen receptor positive, progesterone receptor negative and HER2 or Ki67 positive. These tumors tend to grow more quickly than luminal A tumors.

In triple negative breast cancer (TNBC), the cells do not contain receptors for estrogen, progesterone or HER2. This type of breast cancer is usually invasive and usually begins in the breast ducts.

The classification of breast cancer can be determined by means readily known to those of skill in the art and is described, e.g., in Russnes et al., (Am Jounal of Pathology 2017 187(10): 2152-2162) for assessing the genotype and/or levels of the markers, e.g., HER2, ER, PR, and Ki67 including but not limited to, determining the genomic sequence of marker, e.g., by DNA sequencing or allele specific PCR, determining expression of the marker, e.g., by northern analysis, quantative PCR, or microarray analysis, or determining protein levels of the marker, e.g., by western analysis, mass spectrometry, immunohistochemistry, ect.

The terms "administer," "administering," or "administration," as used herein refers to implanting, absorbing, ingesting, injecting, or inhaling the one or more therapeutic agents.

As used herein, the term "treating" refers to the application or administration of a composition including one or more active agents to a subject, who has cancer, a symptom of cancer, or a predisposition toward the disease, with the purpose to cure, heal, alleviate, relieve, alter, remedy, ameliorate, improve, or affect the disorder, the symptom of the disease, or the predisposition toward the disease.

Alleviating cancer includes delaying the development or progression of the disease, or reducing disease severity. Alleviating the disease does not necessarily require curative results. As used therein, "delaying" the development of a disease (such as cancer) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of cancer includes initial onset and/or recurrence.

An "effective amount" refers to an amount sufficient to elicit the desired biological response, i.e., treating the cancer. As will be appreciated by those of ordinary skill in this art, the effective amount of the compounds described herein may vary depending on such factors as the desired biological endpoint, the pharmacokinetics of the compound, the condition being treated, the mode of administration, and the age and health of the subject. An effective amount includes, but is not limited to, that amount necessary to slow, reduce, inhibit, ameliorate or reverse one or more symptoms associated with cancer. For example, in the treatment of cancer, such terms may refer to a reduction in the size of the tumor.

The compounds provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

As used herein, the term "in combination" refers to the use of more than one therapeutic agent. The use of the term "in combination" does not restrict the order in which the therapeutic agents are administered to a subject with neoplasia. A first therapeutic agent, such as (i) a STING agonist; (ii) an Immune Checkpoint Blockade (ICB) agent; (iii) an interferon gamma signaling agonist; (iv) a DNA methyltransferase inhibitor; or (v) an EZH2 inhibitor, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, such as (i) a STING agonist; (ii) an Immune Checkpoint Blockade (ICB) agent; (iii) an interferon gamma signaling agonist; (iv) a DNA methyltransferase inhibitor; or (v) an EZH2 inhibitor described herein, to a subject. Thus, a first agent can be administered separately, sequentially or simultaneously with the second therapeutic agent.

In some embodiments, levels of STING and/or levels of one or more SPARCS genes are determined in a subject and a therapy is selected based on the level(s). In some embodiments, the therapy is a STING agonist. In some embodiments, the therapy is an Immune Checkpoint Blockade (ICB) agent. In some embodiments, the therapy is an interferon gamma signaling agonist. In some embodiments, the therapy is a DNA methyltransferase inhibitor. In some embodiments, the therapy is an EZH2 inhibitor.

In one embodiment, the STING agonist is a cyclic dinucleotide or a chemical molecule that binds to and activates STING, e.g., a cyclic dinucleotide comprising purine or pyrimidine nucleobases (e.g., adenosine, guanine, uracil, thymine, or cytosine nucleobases). In some embodiments, the nucleobases of the cyclic dinucleotide comprise the same nucleobase or different nucleobases. In some embodiments, the STING agonist comprises an adenosine or a guanosine nucleobase. In some embodiments, the STING agonist comprises one adenosine nucleobase and one guanosine nucleobase. In some embodiments, the STING agonist comprises two adenosine nucleobases or two guanosine nucleobases. In some embodiments, the STING agonist comprises a modified cyclic dinucleotide, e.g., comprising a modified nucleobase, a modified ribose, or a modified phosphate linkage. In some embodiments, the modified cyclic dinucleotide comprises a modified phosphate linkage, e.g., a thiophosphate. In some embodiments, the STING agonist comprises a cyclic dinucleotide (e.g., a modified cyclic dinucleotide) with 2',5' or 3',5' phosphate linkages. In some embodiments, the STING agonist comprises a cyclic dinucleotide (e.g., a modified cyclic dinucleotide) with Rp or Sp stereochemistry around the phosphate linkages.

The bacteria-produced cyclic dinucleotides, c-di-AMP, c-di-GMP and 3'3'-cGAMP, are agonists of STING. Other exemplary STING agonists include, e.g., cGAMP, c-di-GAMP, 2',3'-cGAMP, 2'3'-c-di-AM(PS)2 (Rp,Rp), c-AIMP; (3',2')c-AIMP; (2',2')c-AIMP; (2',3')c-AIMP; c-AIMP(S); c-(dAMP-dITMP); c-(dAMP-2'FdIMP); c-(2'FdAMP-2'FdIMP); (2',3')c-(AMP-2'FdIMP); c-[2'FdAMP(S)-2'FdIMP(S)]; c-[2'FdAMP(S)-2'FdIMP(S)](POM)2; Rp,Rp dithio 2',3' c-di-AMP (e.g., Rp,Rp-dithio c-[A(2',5')pA(3',5')p]) or a cyclic dinucleotide analog thereof; c-[G(2',5')pG(3',5')p] or a dithio ribose 0-substituted derivative thereof; c-[A(2',5')pA(3',5')p] or a dithio ribose 0-substituted derivative thereof, 2'-O-propargyl-cyclic-[A(2',5')pA(3',5')p] (2'-O-propargyl-ML-CDA), CL614 (Invitrogen), CL614 (Invitrogen), CL656 (Invitrogen), 2'3'-cGAM(PS)2 (Rp/Sp), cyclic [FdG(3',5')pFdA(3',5')p], cyclic [FdA(3',5')pFdA(3',5')p], 2'3'-c-di-AMP, cyclic [FdG(3',5')pFdG(3',5')p], 2'3'-c-di-GMP, c-di-IMP, 5601 (Tocris), G10 (Tocris), SB 11285 (Spring Bank Pharmaceuticals), MK-1454 (Merck), or ADU-S100 (Aduro Biotech). In another embodiment, the unnatural or synthetic dinucleotide 2'2'-cGAMP is an agonist of STING In some embodiments, the STING agonist can comprise a flavonoid. In other embodiments, the STING agonist can consist of a flavonoid. Suitable flavonoids include, but are not limited to, 10-(carboxymethyl)-9(10H) acridone (CMA), acid (DMXAA), methoxyvone, 6,4'-dimethoxyflavone, 4'-methoxyflavone, 3',6'-dihydroxyflavone, 7,2'-dihydroxyflavone, daidzein, formononetin, retusin 7-methyl ether, xanthone, or any combination thereof. In some embodiments, the STING agonist is a dimeric amidobenzimidazole. In some embodiments, the STING agonist is SRCB-0074 (See Chin et al., Open 2018; 3). Other exemplary STING agonists are disclosed, e.g., in PCT Publication Nos. WO 2014/189805 and WO 2014/189806, and U.S. Publication Nos. 2015/0056225 2016/0287623 and 2018/0028553, each of which is incorporated by reference.

In some embodiments, a STING agonist comprises the STING protein or a fragment thereof. In some embodiments, a fragment of the STING protein comprises 10 or more consecutive amino acid residues of SEQ ID NO: 1, e.g., 15 or more, 20 or more, 25 or more, 30 or more, 35 or more, 50 or more, 100 or more, or 200 or more consecutive amino acid residues of SEQ ID NO: 1. In some embodiments, the STING agonist is a protein that is about 80%, 85%, 90%, 95%, or 99% identical to SEQ ID NO: 1.

In some embodiments, a STING agonist comprises an mRNA, e.g., a synthetic mRNA expressing the STING protein or a fragment thereof. As used herein the term, "synthetic mRNA" refers to a mRNA produced through an in vitro transcription reaction or through artificial (non-natural) chemical synthesis or through a combination thereof. In some embodiments, the synthetic RNA further comprises a poly A tail, a Kozak sequence, a 3' untranslated region, a 5' untranslated region, or any combination thereof. Poly A tails in particular can be added to a synthetic RNA using a variety of art-recognized techniques, e.g., using poly A polymerase (Yokoe, et al. Nature Biotechnology. 1996; 14:1252-1256), using transcription directly from PCR products, or by ligating to the 3' end of a synthetic RNA with RNA ligase (see, e.g., Molecular Cloning A Laboratory Manual, 2 nd Ed., ed. by Sambrook, Fritsch and Maniatis (Cold Spring Harbor Laboratory Press: 1991 edition)).

In some embodiments, a STING agonist comprises a vector encoding the STING protein or a fragment thereof. Viral vectors are engineered to transduce one or more desired nucleic acids into a cell. In some embodiments, the viral vector is a retroviral transfer vector, an adenoviral vector, a lentiviral vector or an adeno-associated viral vector. In some embodiments, the viral vector is an adenoviral vector, and the adenoviral vector is a subgroup A, subgroup B, subgroup C, subgroup D, subgroup E, or subgroup F adenoviral vector. In some embodiments, the viral vector is a lentiviral vector, and the lentiviral vector is an HIV, SIV, FIV, EIAVor ovine lentiviral vector. In some embodiments, the viral vector is an adeno-associated viral vector, and the adeno-associated viral vector is an AAV1, AAV2, AAV5, AAV6, AAV6.2, AAV7, AAV8, AAV9, AAV10 or AAV11 adeno-associated viral vector. In some embodiments, the viral vector is a chimeric viral vector. In one embodiment of any one of the methods provided herein, the chimeric viral vector is an AAV-adenoviral transfer vector.

In any of the foregoing aspects and following embodiments, an Immune Checkpoint Blockade (ICB) agent is, for example, an antagonist of surface proteins which are members of either the TNF receptor or B7 superfamilies, including without limitation, programmed death 1 (PD-1), programmed death ligand 1 (PD-L1), cytotoxic T-lymphocyte-associated antigen 4 (CTLA-4), V-domain Ig suppressor of T cell activation (VISTA), programmed death ligand 2 (PD-L2), indoleamine 2,3-dioxygenase (IDO), arginase, B7 family inhibitory ligand B7-H3, B7 family inhibitory ligand B7-H4, lymphocyte activation gene 3 (LAG3), 2B4, B and T lymphocyte attenuator (BTLA), T cell membrane protein 3 (TIM3; also known as HAVcr2), adenosine A2a receptor (A2aR), a killer inhibitory receptor, CD160, CD244, TIGIT, BMA, and/or signal transducer and activator of transcription (STAT)3. In some embodiments, the antagonist of the is agent that binds to and antagonizes the surface protein, e.g., PD-1, PD-L1, CTLA-4, VISTA, PD-L2, IDO, B7-143, B7-H4, LAG3, 2B4, BTLA, TIM3, A2aR, CD160, CD244, TIGIT, BMA, and/or STAT3 is (i) an antisense molecule directed against a nucleic acid encoding the surface protein, (ii) an adnectin directed against a nucleic acid encoding the surface protein, (iii) a single stranded or double stranded RNAi inhibitor of the surface protein, (iv) a small molecule inhibitor of the surface protein, or (v) an antibody that specifically binds the surface protein.

In any of the foregoing aspects and embodiments, the PD-1 antagonist is, for example, an agent that binds to and antagonizes PD-1. Such agents can be, for example, a peptide that binds PD-1. Such agents can be a humanized antibody that selectively binds PD-1. In some embodiments, the humanized antibody that selectively binds PD-1 is lambrolizumab, nivolumab, pembrolizumab, pidilizumab, MEDI-0680, REGN2810, or AMP-224. In some embodiments, the humanized antibody that selectively binds PD-1 is nivolumab, pembrolizumab, or pidilizumab. In some embodiments, the antagonist is (i) an antisense molecule directed against PD-1 nucleic acid, (ii) an adnectin directed against PD-1 nucleic acid, (iii) a single stranded or double stranded RNAi inhibitor of PD-1, and/or (iv) a small molecule inhibitor of PD-1.

In any of the foregoing aspects and embodiments, the PD-L1 antagonist is, for example, an agent that binds to and antagonizes PD-L1. Such agents can be, for example, a peptide that binds PD-L1. Such agents can be a humanized antibody that selectively binds PD-L1. In some embodiments, the humanized antibody that selectively binds PD-L1 is BMS-936559/MDX-1105, MPDL33280A/RG7446/atezolizumab, MSB0010718C/avelumab, MIH1, pembrolizumab, or MEDI4736/durvalumab. In some embodiments, the antagonist is (i) an antisense molecule directed against PD-L1, (ii) an adnectin directed against PD-L1, (iii) a single stranded or double stranded RNAi inhibitor of PD-L1, or (iv) a small molecule inhibitor of PD-L1.

B7-H3 checkpoint inhibitors, include, without limitation, antibodies neutralizing human B7-113 (e.g. MGA271 disclosed as BRCA84D and derivatives in U.S. Patent Application Publication No. 2012/0294796, incorporated herein by reference). In some embodiments, the antagonist is (i) an antisense molecule directed against B7-H3, (ii) an adnectin directed against B7-H3, (iii) a single stranded or double stranded RNAi inhibitor of B7-H3, or (iv) a small molecule inhibitor of B7-H3.

B7H4 checkpoint inhibitors include, without limitation, antibodies to human B7H4 (disclosed in WO 2013025779 A1, and in U.S. Patent Application Publication No. 2014/0294861, incorporated herein by reference) or soluble recombinant forms of B7H4 (such as disclosed in U.S. Patent Application Publication No. 2012/0177645, incorporated herein by reference, or Anti-human B7H4 clone H74: eBioscience #14-5948). In some embodiments, the antagonist is (i) an antisense molecule directed against B7-H4, (ii) an adnectin directed against B7-H4, (iii) a single stranded or double stranded RNAi inhibitor of B7-H4, or (iv) a small molecule inhibitor of B7-H4.

TIM3 checkpoint inhibitors include, without limitation, antibodies targeting human TIM3 (e.g. as disclosed in U.S. Pat. No. 8,841,418, incorporated herein by reference, or the anti-human TIM3, blocking antibody F38-2E2 disclosed by Jones et al., J Exp Med., 205(12):2763-79 (2008)). In some embodiments, the antagonist is (i) an antisense molecule directed against TIM3, (ii) an adnectin directed against TIM3, (iii) a single stranded or double stranded RNAi inhibitor of TIM3, or (iv) a small molecule inhibitor of TIM3.

TIGIT checkpoint inhibitors preferably inhibit interaction of TIGIT with polovirus receptor (CD155) and include, without limitation, antibodies targeting human TIGIT, such as those disclosed in U.S. Pat. No. 9,499,596 and U.S. Patent Application Publication Nos. 20160355589, 20160176963 and polovirus variants such as those disclosed in U.S. Pat. No. 9,327,014. In some embodiments, the antagonist is (i) an antisense molecule directed against TIGIT, (ii) an adnectin directed against TIGIT, (iii) a single stranded or double stranded RNAi inhibitor of TIGIT, or (iv) a small molecule inhibitor of TIGIT.

In any of the foregoing aspects and embodiments, the CTLA-4 antagonist is, for example, an agent that binds to and antagonizes CTLA-4. Such agents can be, for example, a peptide that binds CTLA-4. Such agents can be a humanized antibody that selectively binds CTLA-4. In some embodiments, the humanized antibody that selectively binds CTLA-4 is ipilimumab or tremelimumab. In some embodiments, the CTLA-4 antagonist is (i) an antisense molecule directed against CD80, CD86, and/or CTLA-4 nucleic acid, (ii) an adnectin directed against CD80, CD86, and/or CTLA-4 nucleic acid, (iii) a single stranded or double stranded RNAi inhibitor of CD80, CD86, and/or CTLA-4, or (iv) a small molecule inhibitor of CD80, CD86, or CTLA-4.

In any of the foregoing aspects and embodiments, the VISTA antagonist is, for example, an agent that binds to and antagonizes VISTA. Such agents can be, for example, a peptide. Such agents can be an inhibitory antibody directed to VISTA. In some embodiments, the agent that binds to and antagonizes VISTA is a humanized antibody. In some embodiments, the agent that binds to and antagonizes VISTA is (i) an antisense molecule directed against VISTA nucleic acid, (ii) an adnectin directed against VISTA nucleic acid, (iii) a single stranded or double stranded RNAi inhibitor of VISTA, or (iv) a small molecule inhibitor of VISTA.

Exemplary interferon gamma signaling agonists include, e.g., interferon gamma or interferon gamma variants. In some embodiments, an interferon gamma or interferon gamma variant comprises Actimmune (Genentech). In some embodiments, an interferon gamma or interferon gamma variant comprises recombinant interferon gamma described, for example, in Gray et al., Nature 295, 503-508 (1982); U.S. Pat. Nos. 4,762,791, 4,929,544, 4,727,138, 4,925,793, 4,855,238, 5,582,824, 5,096,705, 5,574,137, and 5,595,888, the contents of each of which are incorporated by reference herein in their entirety. In some embodiments, an interferon gamma or interferon gamma variant comprises recombinant interferon gamma variants described in 7,038,015 or 6,958,388, the contents of each of which are incorporated by reference herein in their entirety.

Interferon gamma has the following amino acid sequence:

```
                                    (SEQ ID NO: 110)
mkytsyilaf qlcivlgslg cycqdpyvke aenlkkyfna ghsdvadngt lflgilknwkeesdrkimqs qivsfyfklf knfkddqsiq ksvetikedm nvkffnsnkk krddfekltnysvtdlnvqr kaiheliqvm aelspaaktg krkrsqmlfr grrasq
```

In some embodiments, an interferon gamma signaling agonist comprises the interferon gamma protein or a fragment thereof. In some embodiments, a fragment of the interferon gamma protein comprises 10 or more consecutive amino acid residues of SEQ ID NO: 110, e.g., 15 or more, 20 or more, 25 or more, 30 or more, 35 or more, 50 or more, 100 or more, or 200 or more consecutive amino acid residues of SEQ ID NO: 110. In some embodiments, the interferon gamma signaling agonist is a protein that is about 80%, 85%, 90%, 95%, or 99% identical to SEQ ID NO: 110. In some embodiments, an interferon gamma signaling agonist comprises an mRNA, e.g., a synthetic mRNA expressing the interferon gamma protein or a fragment thereof. In some embodiments, an interferon gamma signaling agonist comprises a retroviral vector encoding the interferon gamma protein or a fragment thereof.

In some embodiments, the interferon gamma signaling agonist comprises baicalin, poly I:C, IL-18, IL-2, IL-12, IL-27, an IL-27 hyperkine, IRF-10, or PTPN2 inhibitors In some embodiments, the interferon gamma signaling agonist comprises mitogens. Exemplary mitogens include but are not limited to lectins, phytohemagglutinin, concanavalin A, pokeweed mitogen, lipopolysaccharide, endotoxin, lipid A, polysaccharide and bacterium.

In some embodiments, the interferon gamma signaling agonist comprises a nucleic acid. In some embodiments, the nucleic acid comprises bacterial DNA. In some embodiments, the nucleic acid comprises an oligonucleotide containing CpG motifs.

In some embodiments, the interferon gamma signaling agonist comprises a small molecule mimic of interferon gamma. Exemplary small molecule mimics of interferon gamma are described, for example, in U.S. Ser. No. 10/197,557, the entire contents of which is incorporated herein by reference in its entirety.

Exemplary DNA methyltransferase inhibitors include, e.g., azacitidine, decitabine, zebularine, NPEOC-DAC, CP-4200, RX-3117, cytosine analogues, thio-cytidine derivatives, e.g., T-dCyd and 5-aza-T-dCyd, decitabine-p-deoxyguanosine (SGI-110), SAM analogues, SAH analogues, SGI-1027, alcyne derivatives, cyclopenta derivatives, cyclohexathiophene derivatives, tryptophane derivates, e.g., RG108, procainamide derivatives, flavonoid derivatives, curcumin, psammaplin, hydralazine, disulfiram, 5-fluro-2'-deoxycitidine, 5-azacytidine, 5-aza-2'-deoxycytidine, 5,6-dihydro-5-azacytidine, 5-fluoro-2'-deoxycytidine, 1-(beta-D-ribofuranosyl)-1,2-dihydropyrimidin-2-one, 5-aza-2'-deoxycytidine-p-deoxyguanosine, fluorocyclopentenylcytosine, 2-(p-nitrophenyl) ethoxycarbonyl-5-aza-2'-deoxycytidine, 4'-thio-2'-deoxycytidine, 5-aza-4'-thio-2'-deoxycytidine, 1-beta-D-arabinofuranosyl-5-azacytosine, hydralazine, procaine, mithramycin A, nanaomycin A, N-(4-((2-amino-6-methylpyrimidin-4-yl)amino)phenyl)-4-(quinolin-4-ylamino)benzamide, N-phthalyl-L-tryptophan, N-phthalyl-L tryptophan derivatives, alkine derivatives, halomon, S-adenosyl-L-methionine analogues, S-adenosyl-L-homocysteine, S-adenosyl-L-homocysteine analogues, MG98, miR-29a, miR-29c, Sinefungin, procainamide, procainamide derivatives, procainamide-N-phthalyl-L-tryptophan conjugates, cyclopentathiophene derivatives, cyclohexathiophene derivatives, flavone derivatives, 3-nitroflavone derivatives, flavanones derivatives, 3-chloro-3-nitroflavanone derivatives, diclone, laccaic acid, acridine, 5,5'-Methylenedisalicylic acid, 4-(2-((5-Chloro-2-methoxybenzoyl)amino)ethyl)hydrocinnamic acid, 4-Chloro-N-(4-hydroxy-1-naphthalenyl)-3-nitro-benzenesulfonamide, (S)-3-(1H-Indol-3-yl)-2-(5-nitro-1,3-dioxo-1,3-dihydro-isoindol-2-yl)-propionic acid, (R)-2-(1,3-Dioxo-5-phenylethynyl-1,3-dihydro-isoindol-2-yl)-3-(1H-indol-3-yl)-propionic acid, (S)-2-(2,6-Dioxo-piperidin-1-yl)-3-(1H-indol-3-yl)-propionic acid, N-hydroxy-4-(2-(4-aminobenzamido)-ethylcarbamoyl)butanamide, 4-amino-N-(2-(ethyl(3-(hydroxyamino)-3-oxopropyl)amino)ethyl)benzamide, N<1>-(2-(4-aminobenzamido)ethyl)-N<1>-ethyl-N<6>-hydroxyadipamide, tetraethylthiuramdisulfide, (−)-epigallocatechin-3-gallate, genistein, psammaplin A, psammaplin derivatives, and anti-DNA methyltransferase antibodies.

Non-limiting examples of EZH2 inhibitors include S-adenosyl-methionine-competitive small molecule inhibitors. In particular non-limiting embodiments, the EZH2 inhibitor is derived from tetramethylpiperidinyl compounds. Further non-limiting examples include UNC1999, 3-Deazaneplanocin A (DZNcp), EI1, EPZ-5676, EPZ-6438, GSK343, EPZ005687, EPZ011989, GSK126, CAS #1346574-57-9, (S)-1-(sec-butyl)-N-((4,6-dimethyl-2-oxo-1,2-dihydropyridin-3-yl)methyl)-3-methyl-6-(6-(piperazin-1-yl)pyridin-3-yl)-1H-indole-4-carboxamide, DZNep, tazemetostat, anti-EZH2 antibodies, and siRNA directed against EZH2.

Example 1: Tumor Innate Immunity Primed by Specific Interferon-Stimulated Endogenous Retroviruses Mesenchymal tumor subclones secrete pro-tumorigenic cytokines and promote treatment resistance, but the underlying mechanism remains poorly understood. Here an epigenetically regulated subclass of endogenous retroviruses (ERVs) that engages innate immune signaling in mesenchymal cells is identified. Stimulated 3 Prime Antisense Retroviral Coding Sequences (SPARCS) are oriented inversely in 3'UTRs of certain interferon-inducible genes silenced by EZH2. De-repression of these loci results in dsRNA generation following IFNγ exposure due to bi-directional transcription from the STAT1-activated gene promoter and the 5' LTR of the antisense ERV. dsRNA sensing by MAVS fuels activation of TBK1, IRF3, and STAT1 signaling, sustaining a positive feedback loop. SPARCS induction in human tumors is tightly associated with B2M and MHC class 1 antigen expression, mesenchymal markers, and downregulation of chromatin modifying enzymes, including EZH2. Analysis of cell lines poised to induce high levels of SPARCS expression reveals strong association with an AXL positive mesenchymal cell state. While SPARCS$^{high}$ tumors are marked by immune infiltration, they also exhibit multiple features of immune suppression including checkpoint gene expression and myeloid cell infiltration. Together, these data unveil a novel subclass of ERVs whose de-repression triggers pathologic innate immune signaling in cancer, with important implications for cancer immunotherapy.

Figure 5A:
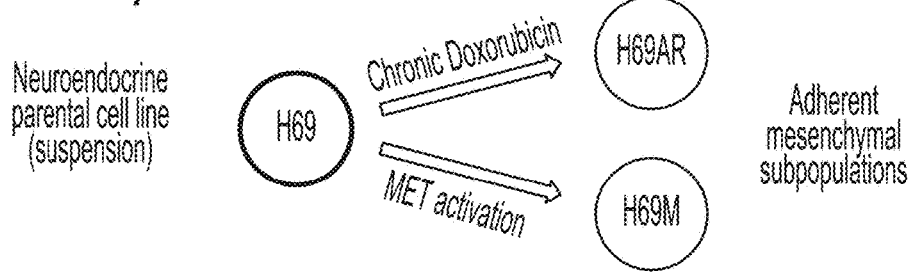
FIGS. 5A-5H show activation of innate immune signaling in mesenchymal SCLC subclones.

Subclonal tumor heterogeneity promotes cancer progression via different growth and metastatic properties, drug sensitivity, and paracrine signaling[1-4]. Resistant small cell lung cancer (SCLC), for example, undergoes a mesenchymal state switch induced by RAS/MET signaling or chemotherapy (e.g. H69M or H69AR cells) (FIG. 5A)[5,6]. A mesenchymal AXL/NF-κB high state also promotes therapeutic resistance[7-10], though remains incompletely defined.

Figure 1E:
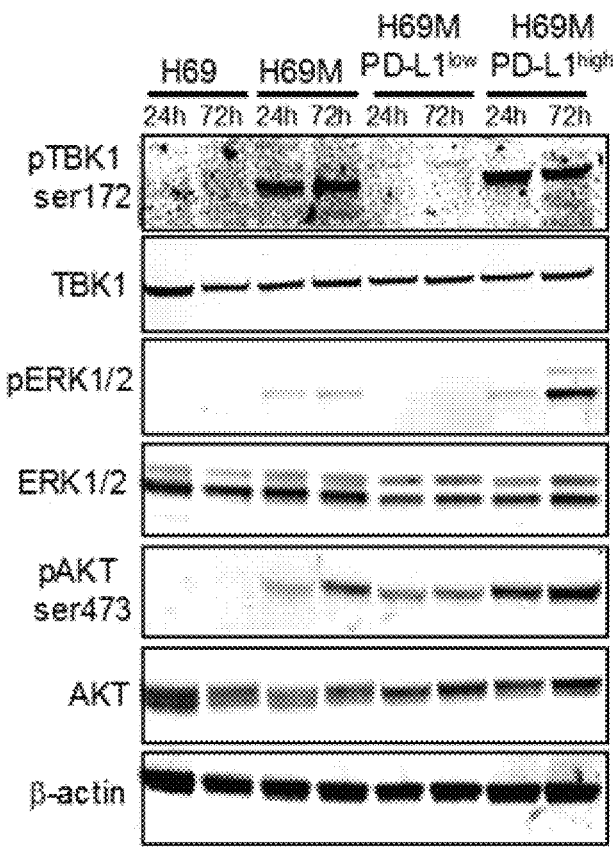
Figure 1F:
Figure 5B:
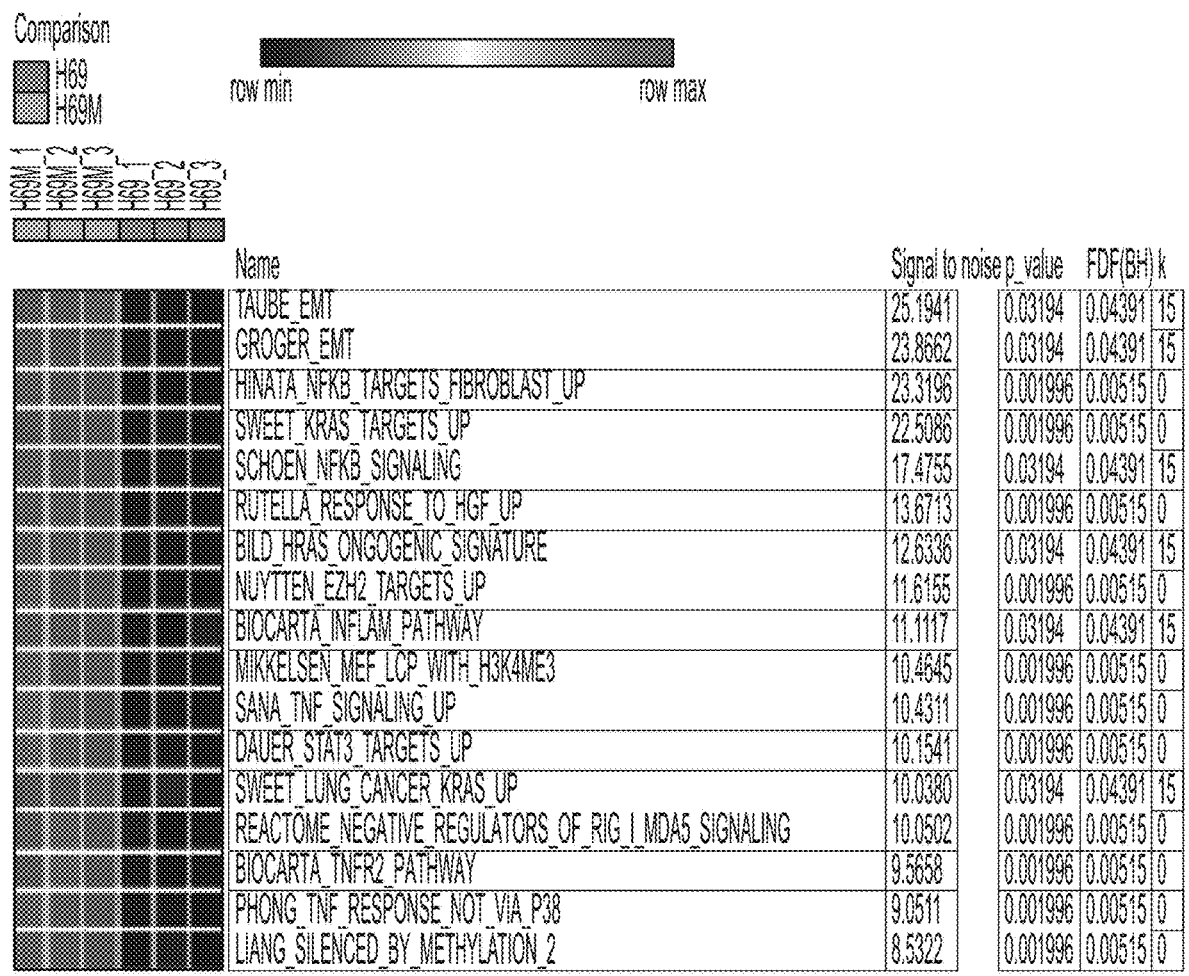
Figure 5B:
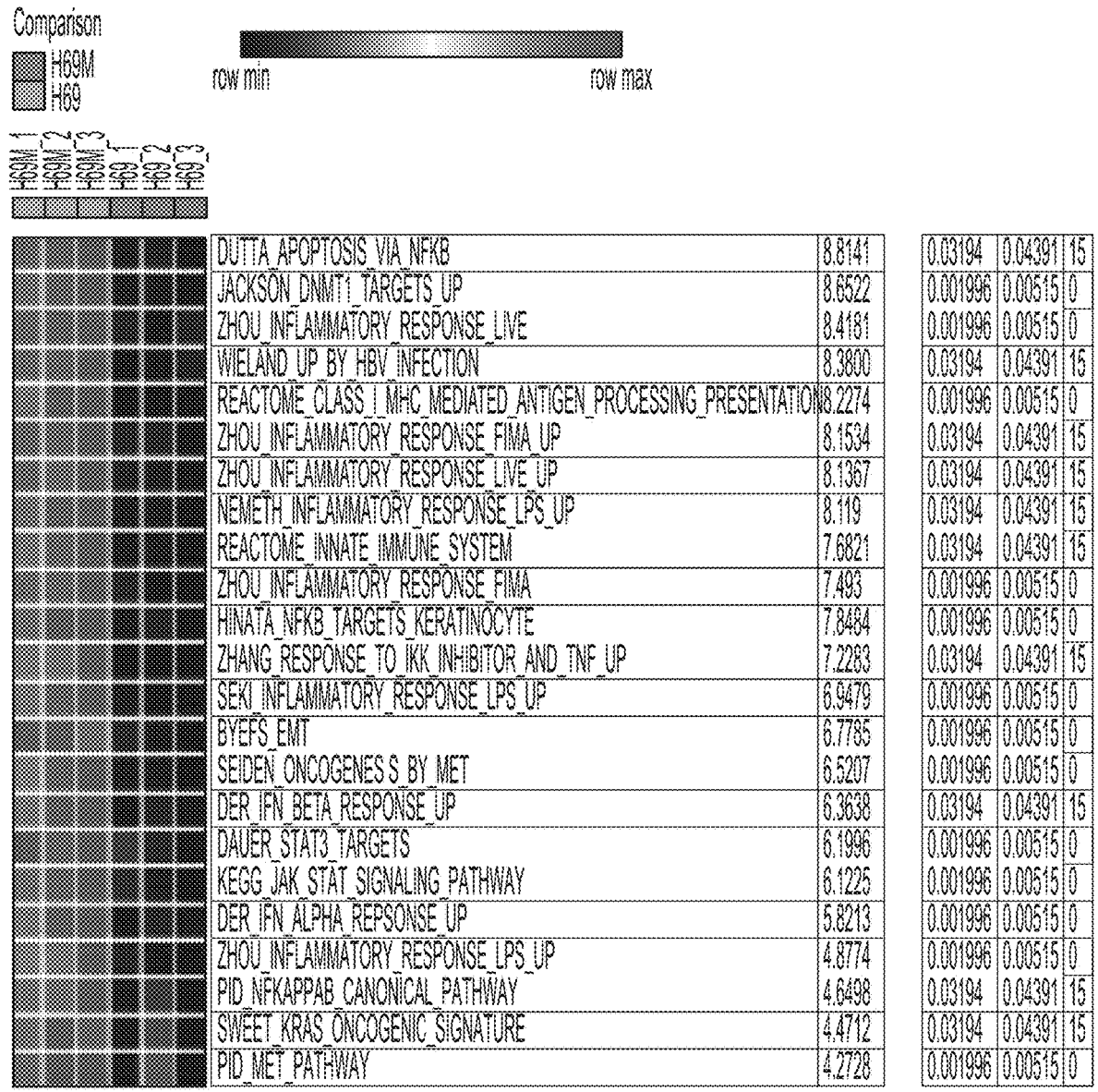
Figure 5C:
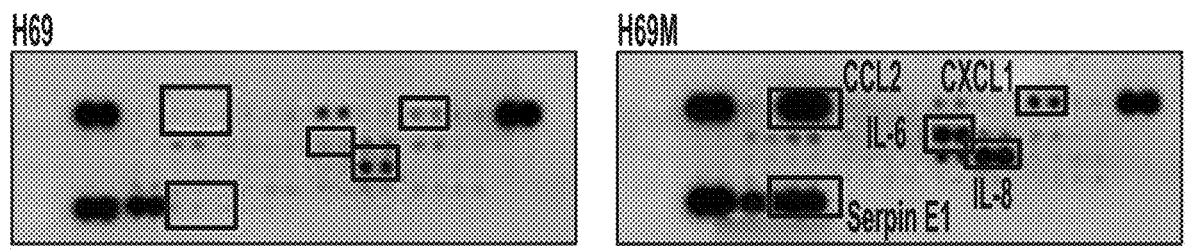
Figure 5D:
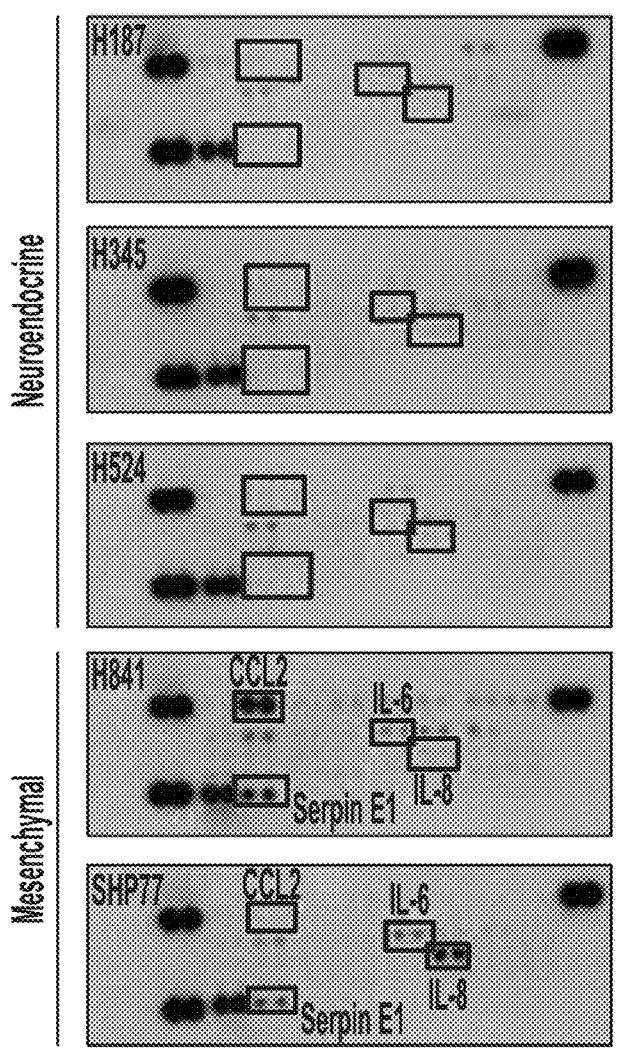
Figure 5E:
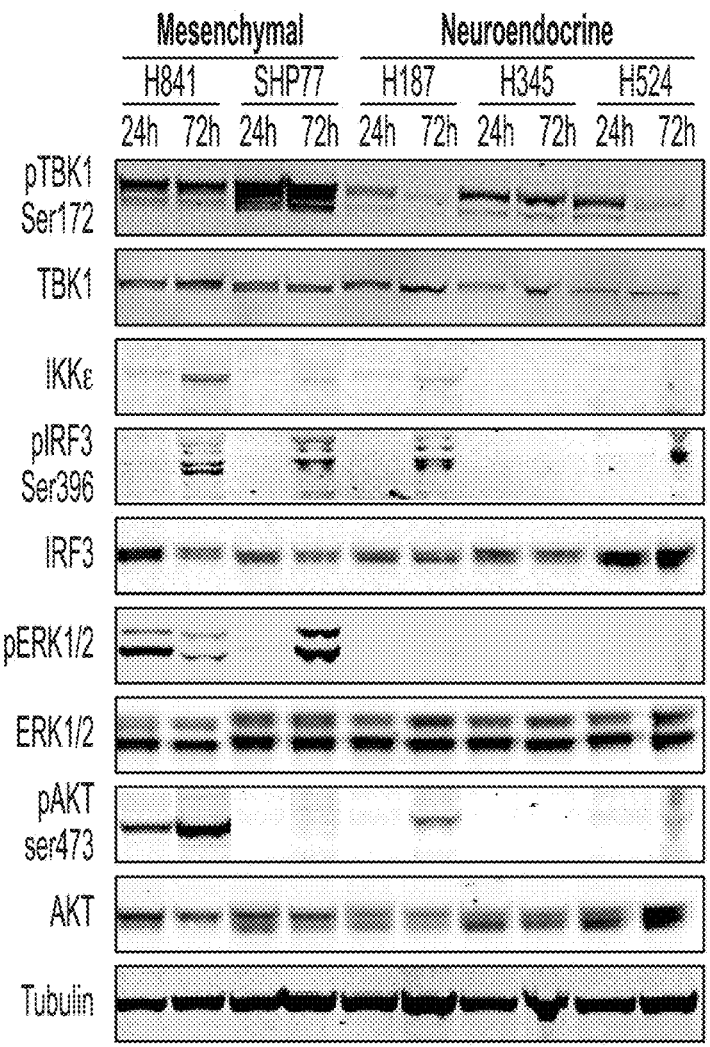
Figure 5F:
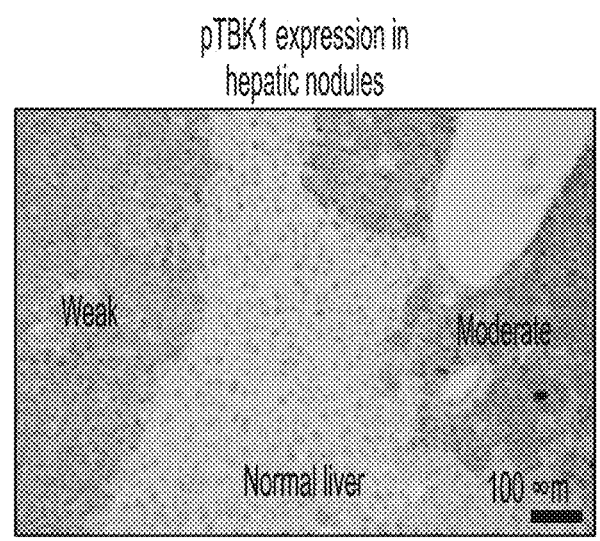
Figure 5G:
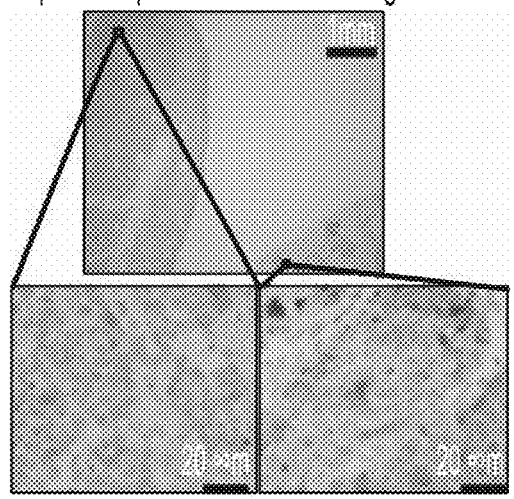
Figure 5H:
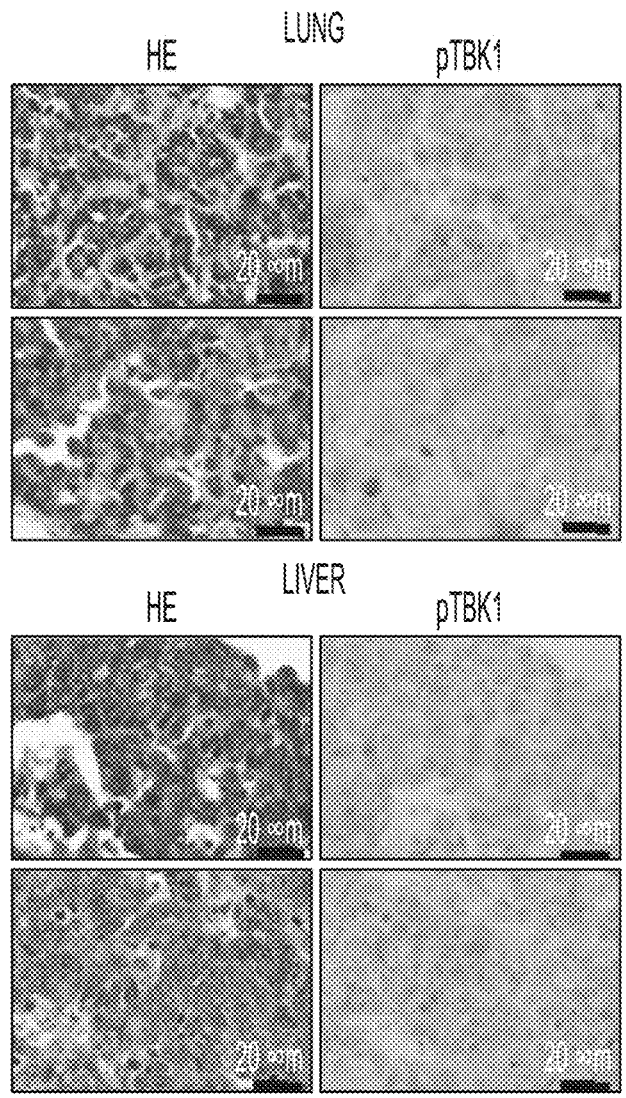
Figure 6A:
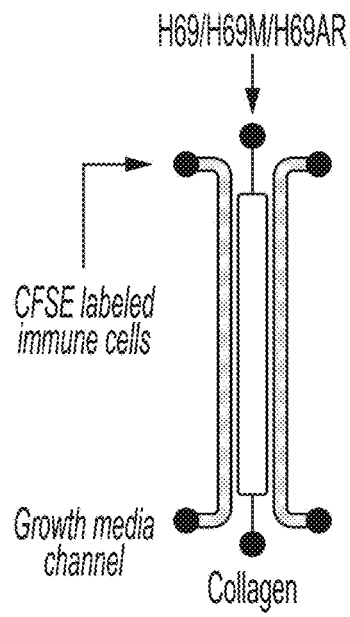
FIGS. 6A-6E show that mesenchymal subclones recruit Jurkat T cells and THP1 monocytes.
Figure 6B:
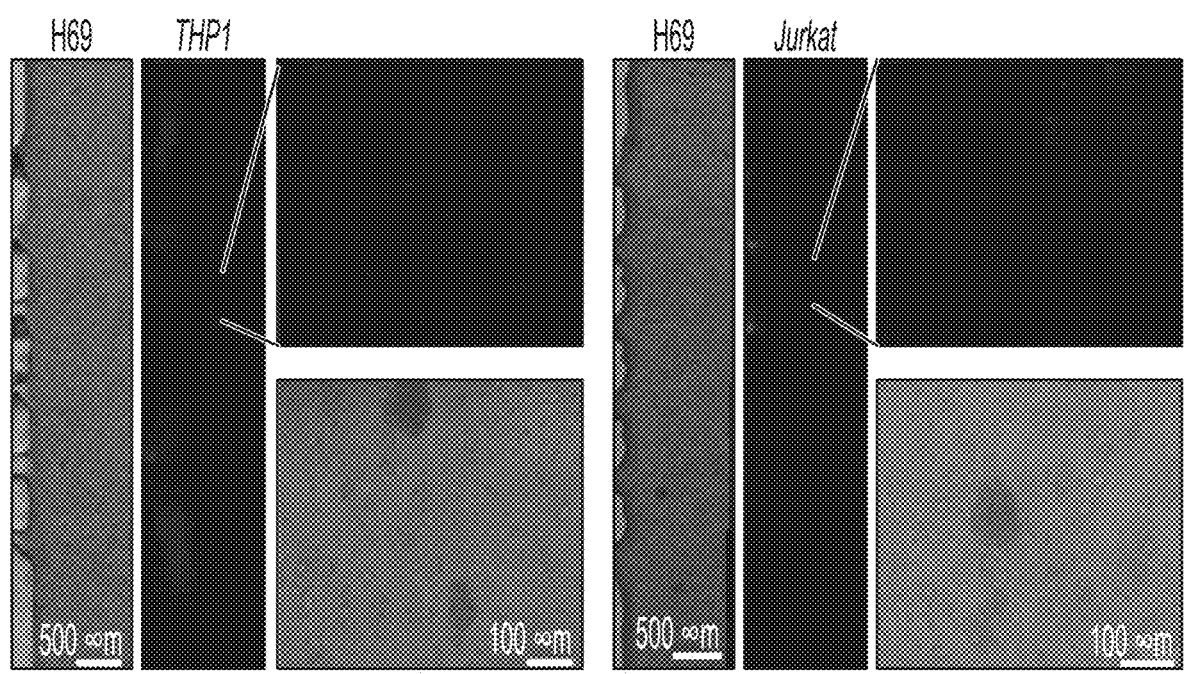
Figure 6C:
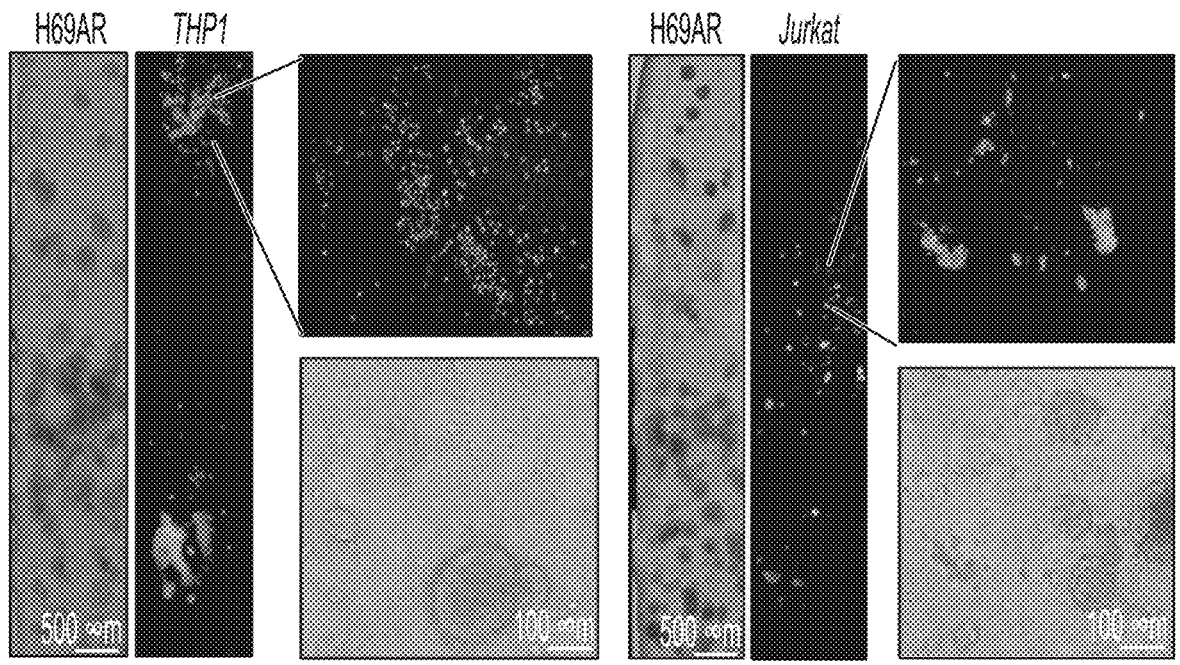
Figure 6D:
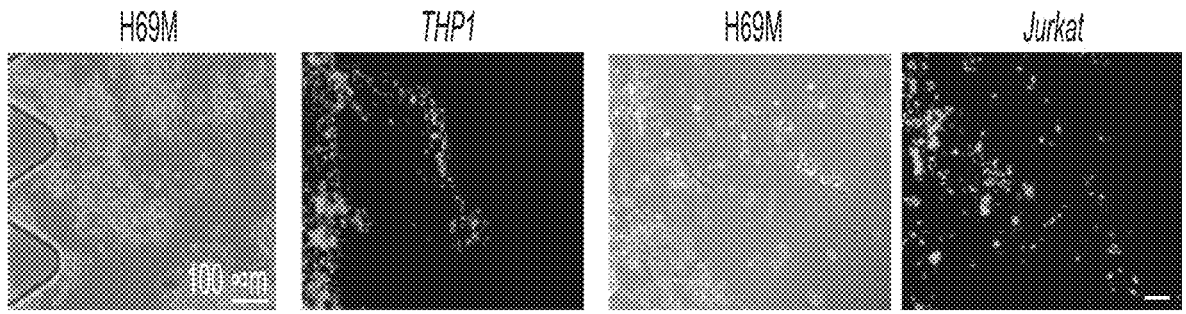
Figure 6E:
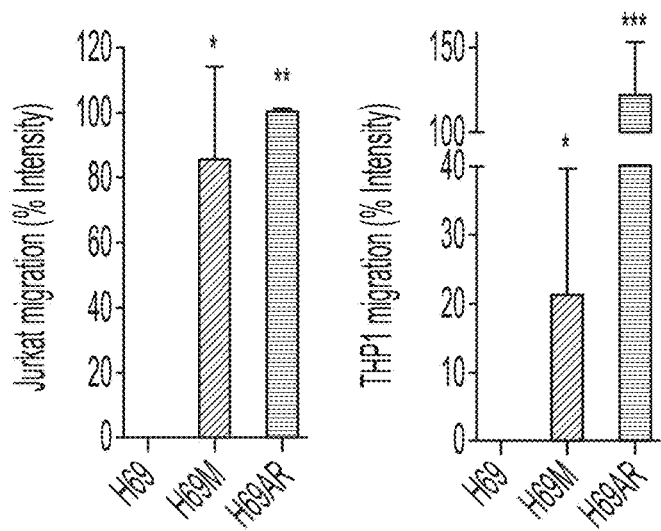
Figure 7A:
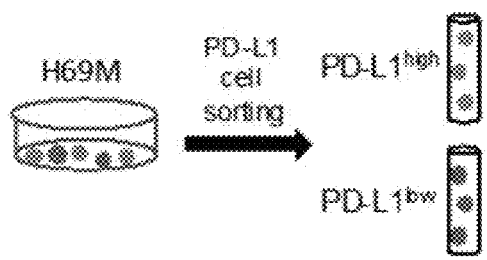
FIGS. 7A-7I show the causal role of ERV sensing in the innate immune phenotype of H69M cells.
Figure 7B:
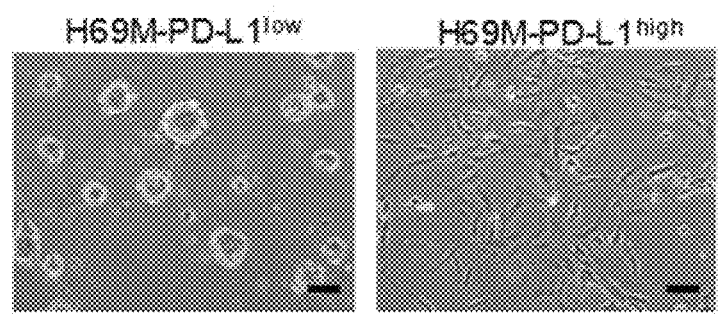

Enhanced innate immune and RAS signaling are noted in H69M cells, including elevated phosphorylated-TBK1 (pTBK1), pIRF3, IKKε and NF-κB gene sets (FIGS. 1A and 5B) and multiple secreted cytokines/chemokines (FIGS. 1B and 5C). pTBK1 levels were preferentially increased in additional mesenchymal SCLC cell lines (FIGS. 5D and 5E), and subclonally in human and murine Rb$^{L/L}$/p53$^{L/L}$ derived SCLC tumors (FIGS. 1C and 5F-H). H69 mesenchymal cell lines also uniquely attracted T cells and monocytes (FIGS. 6A-E), prompting the exploration of immune checkpoint activation. Interestingly, H69M contained a PD-L1$^{high}$, CD44$^{high}$ fibroblastic subclone (FIGS. 1D, 7A, and 7B) that was the source of elevated pTBK1 and cytokine/chemokine production (FIGS. 1E and 1F).

Figure 1G:
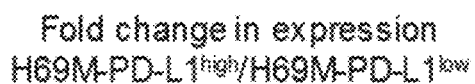
Figure 1H:
Figure 1I:
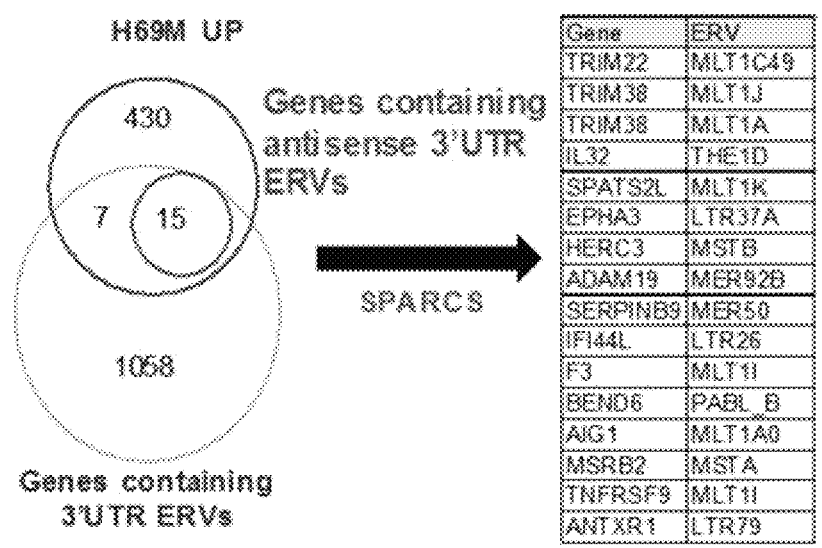
Figure 7C:
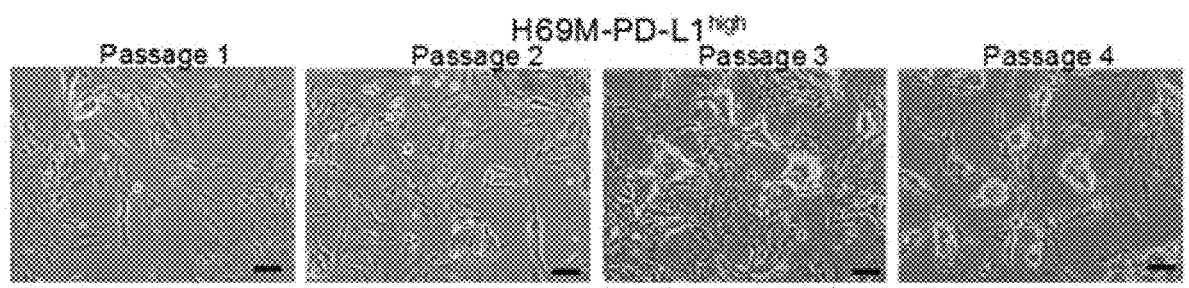
Figure 7D:
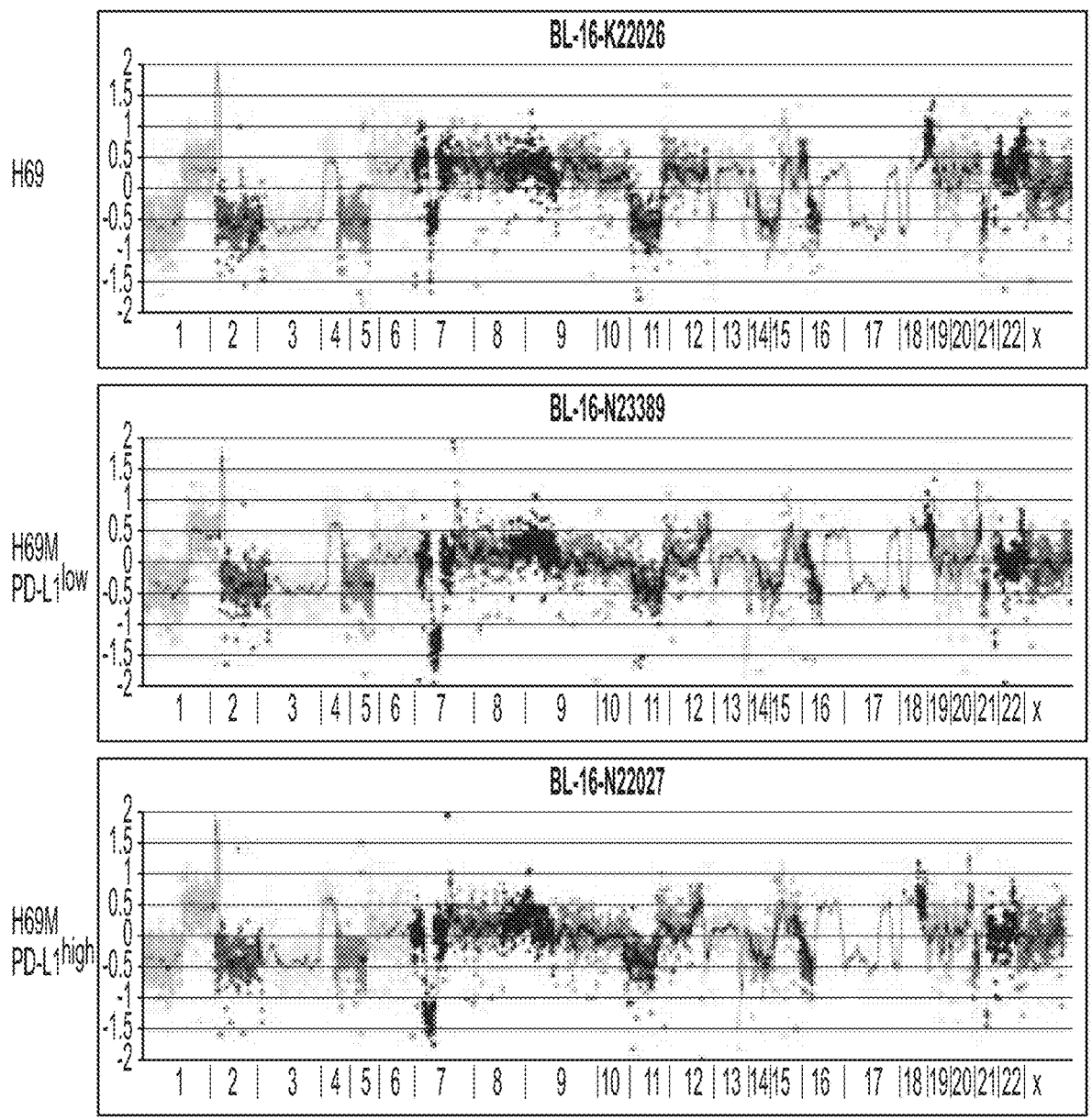

H69M PD-L1$^{high}$ cells reverted morphologically over time and were genomically similar to parental H69 cells (FIGS. 7C and 7D). These findings suggested an epigenetic mechanism of innate immune activation. Since endogenous retroviruses (ERVs) undergo epigenetic silencing, they were assessed for potential de-repression of a recently described ERV panel[11,12]. H69M-PD-L1$^{high}$ cells exhibited marked upregulation of MLT1C49 (FIG. 1G), an ERV poised to generate dsRNA due to antisense orientation in the 3'UTR of TRIM22, an IFN-stimulated gene (FIG. 1H)[13]. Because of this unique feature, all 3'UTR repeat elements from Ref Seq were intersected with H69M upregulated genes[5] identifying TRIM22 and 14 other genes with 3' UTR antisense ERVs, including TRIM38 which contained two (MLT1J, MLT1A) (FIG. 1I). Given their potential to generate dsRNA and spark innate immune signaling these ERVs are termed Stimulated 3 Prime Antisense Retroviral Coding Sequences (SPARCS).

Figure 1J:
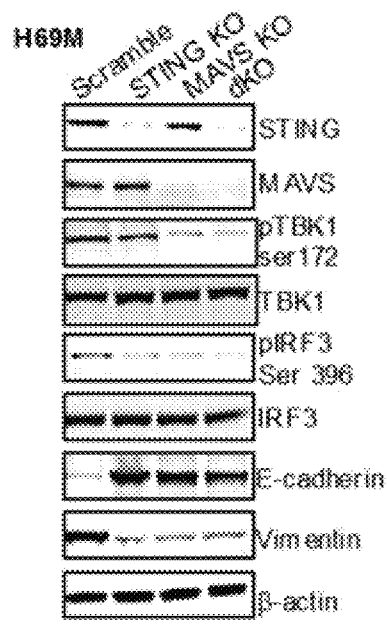
Figure 1K:
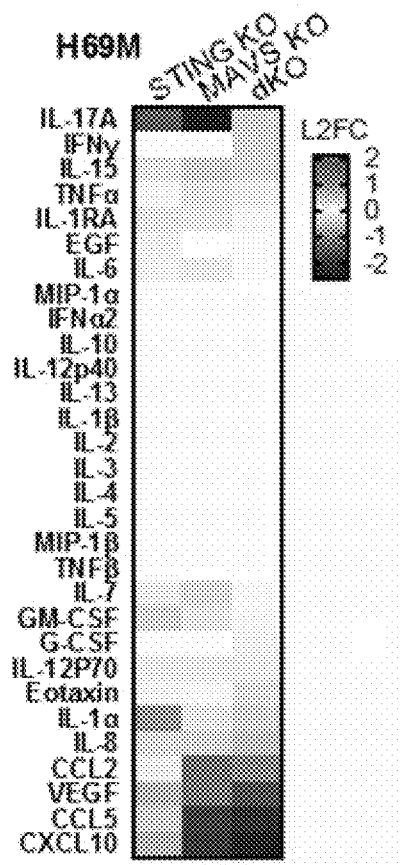
Figure 1L:
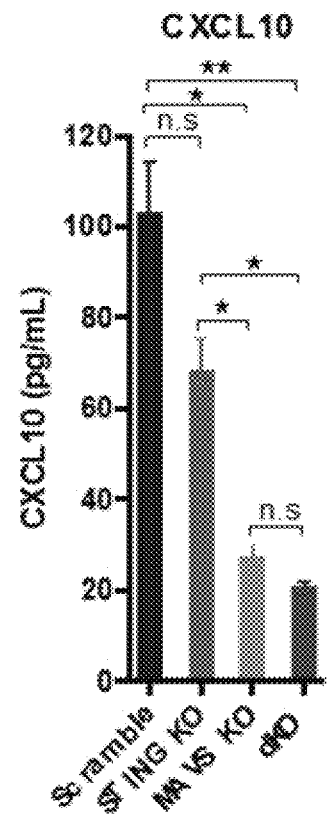
Figure 7E:
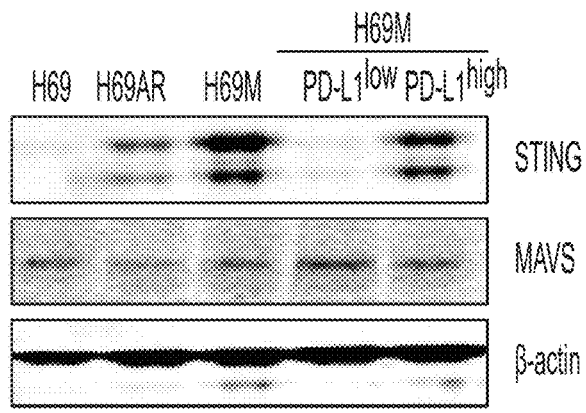
Figure 7F:
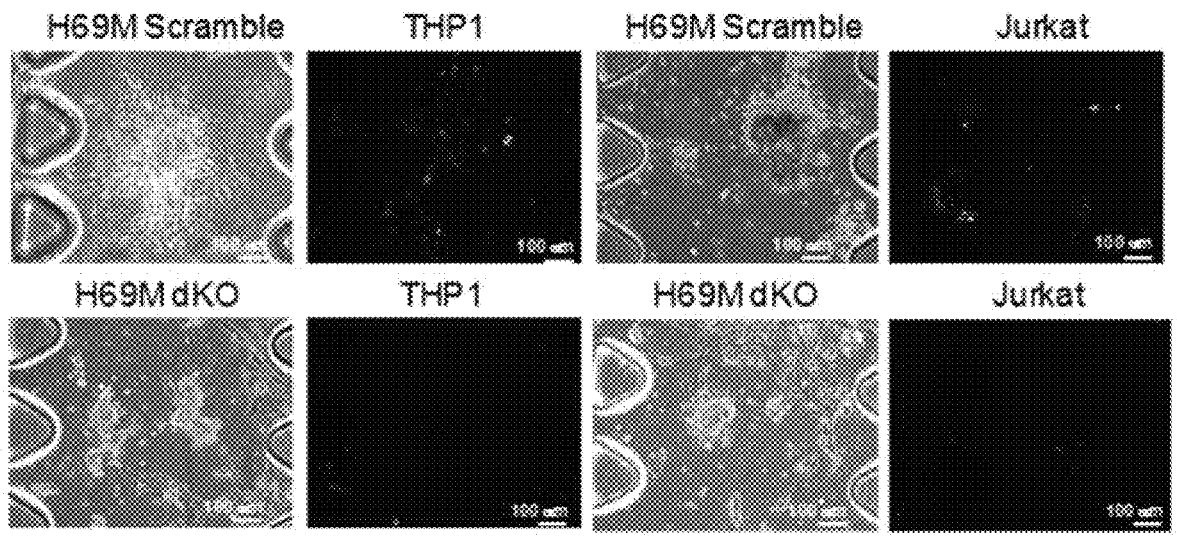
Figure 7G:
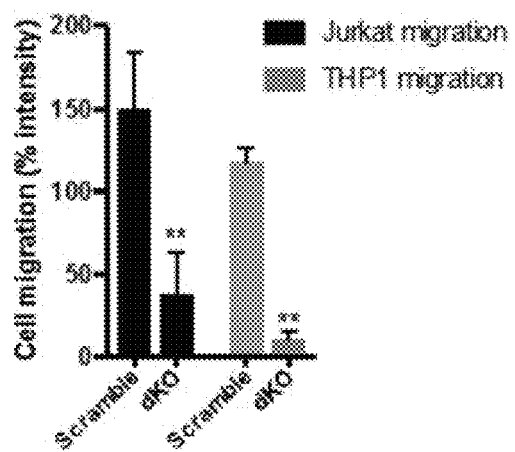
Figure 7H:
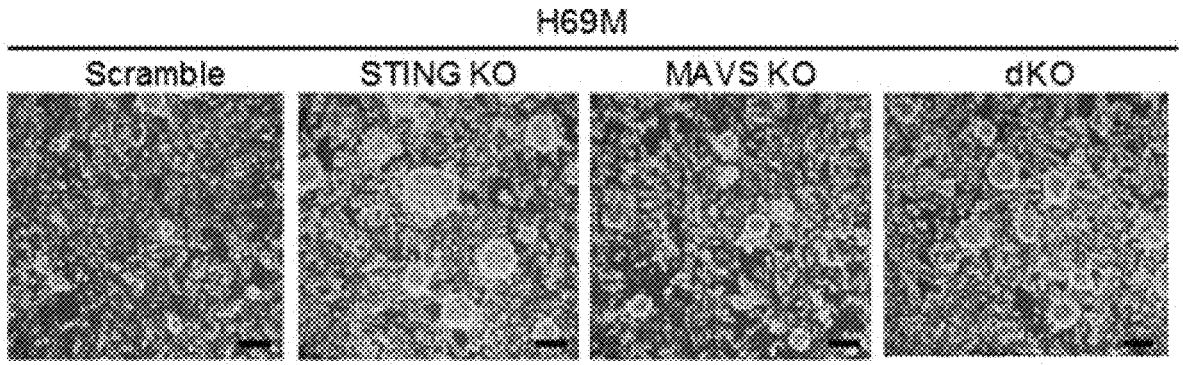
Figure 7I:
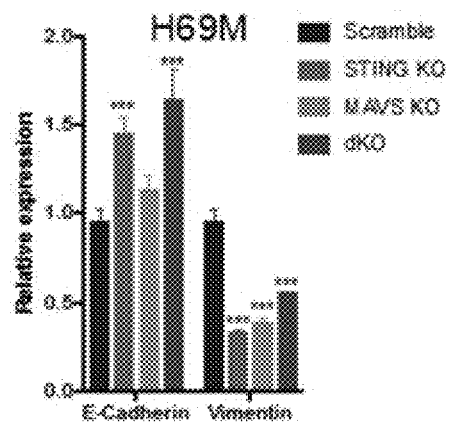

Since ERV dsRNAs are sensed by MAVS or reverse-transcribed and detected via the cGAS-cGAMP STING pathway[14], and since STING especially was upregulated in concert with this phenotype (FIG. 7E), CRISPR was used to delete MAVS and/or STING in H69M cells. MAVS or combined MAVS/STING deletion in H69M cells strongly impaired TBK1 and IRF3 phosphorylation (FIG. 1J), decreased multiple cytokines/chemokines, including CXCL10, CCL5, and CCL2 (FIGS. 1K and 1L) and significantly suppressed T cell and monocyte attraction (FIGS. 7F and 7G). Deletion of MAVS and/or STING also reverted the mesenchymal phenotype (FIG. 7H), increasing E-cadherin and decreasing Vimentin gene and protein expression (FIGS. 1J and 7I). Thus ERV sensing of SPARCS directly contributes to this cellular state.

Figure 2A:
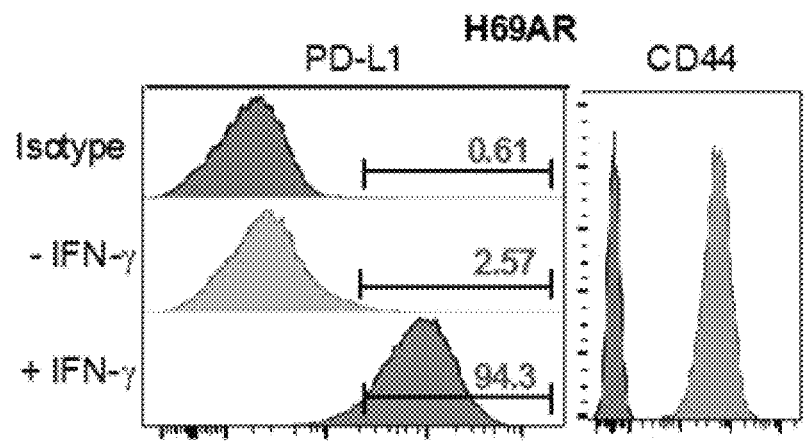
FIGS. 2A-2N shows that SPARCS expression is inducible and triggers positive feedback amplification.
Figure 2B:
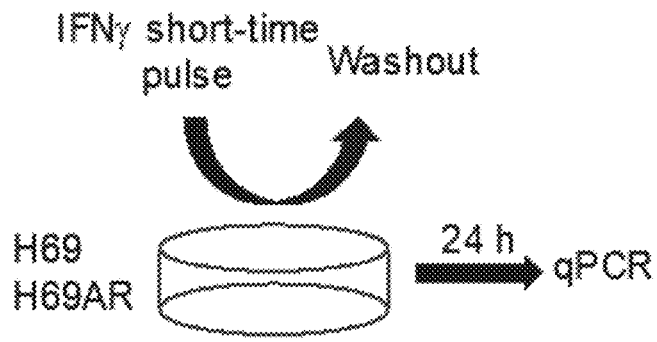
FIG. 2B: Schematic of IFNγ pulse treatment (200 ng/mL) of H69 or H69AR cells. Shown are control, IFNγ 10 min, IFNγ 30 min, IFNγ 1 hr, IFNγ 3 hr, from left to right, for each of H69 and H69AR.
Figure 2C:
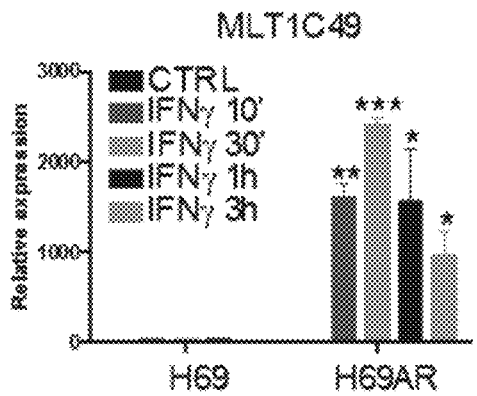
FIG. 2C: qRT-PCR of MLT1C49 in H69 and H69AR cells±200 ng/mL IFNγ pulse–24 h chase. Mean±SD of triplicate samples shown.
Figure 2D:
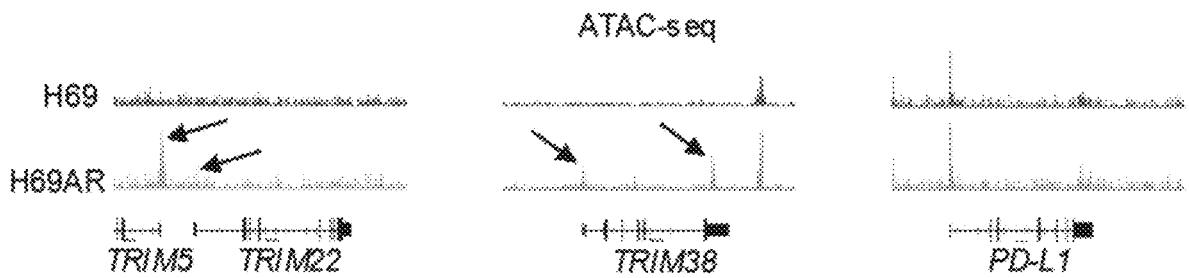
FIG. 2D: ATAC-seq insertion tracks of H69 and H69AR cells around TRIM22, TRIM38 and PD-L1. Differentially accessible regions indicated with arrows.
Figure 2E:
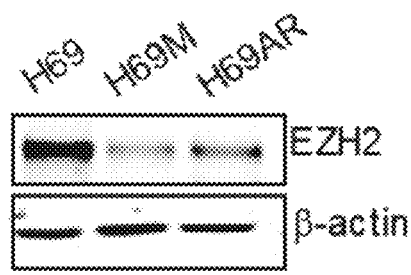
FIG. 2E: Immunoblot of EZH2 and β-actin in H69, H69M and H69AR cells.
Figure 2F:
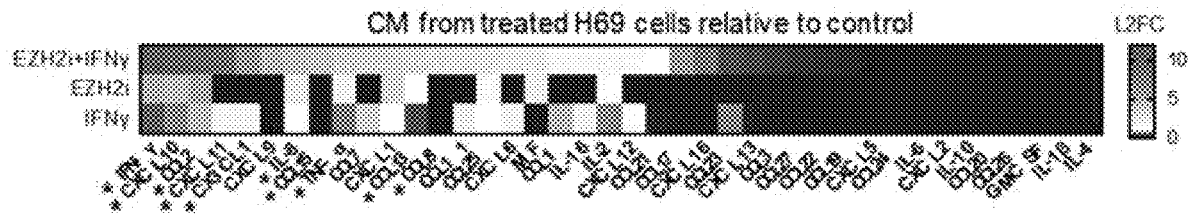
FIG. 2F: Log-2 fold change cytokine/chemokine differences between EZH2i treated H69 cells after IFNγ pulse, EZH2i treated cells, and IFNγ pulsed H69 cells relative to untreated control cells. *same as H69M-PD-L1 high cytokine profile in FIG. 1f.
Figure 2G:
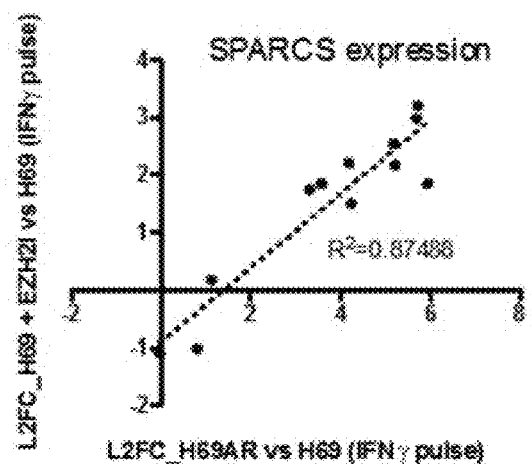
FIG. 2G: Log-2 fold change comparison of IFNγ induced expression of SPARCS genes in EZH2i treated H69 cells versus H69AR cells.
Figure 8A:
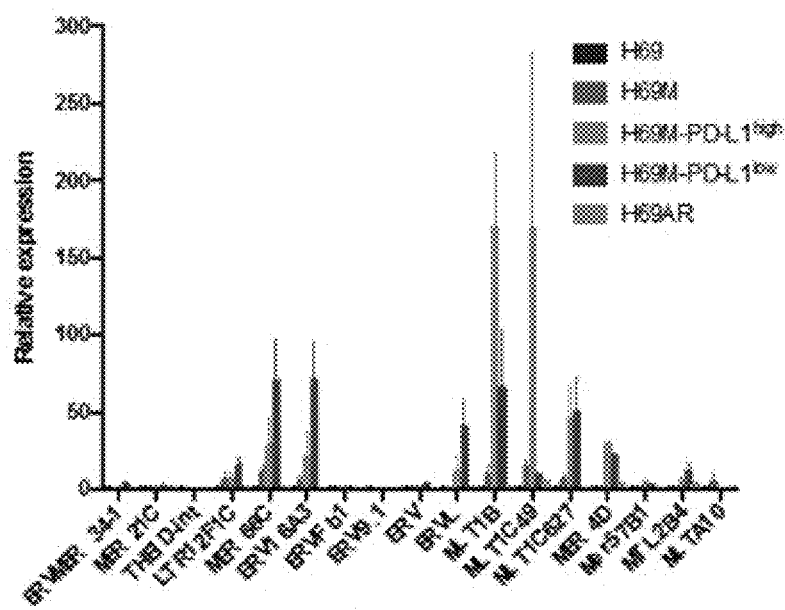
FIGS. 8A-8D show that H69AR chemoresistant cells showed an increased chromatin accessibility state specifically at SPARCS genes.
Figure 8B:
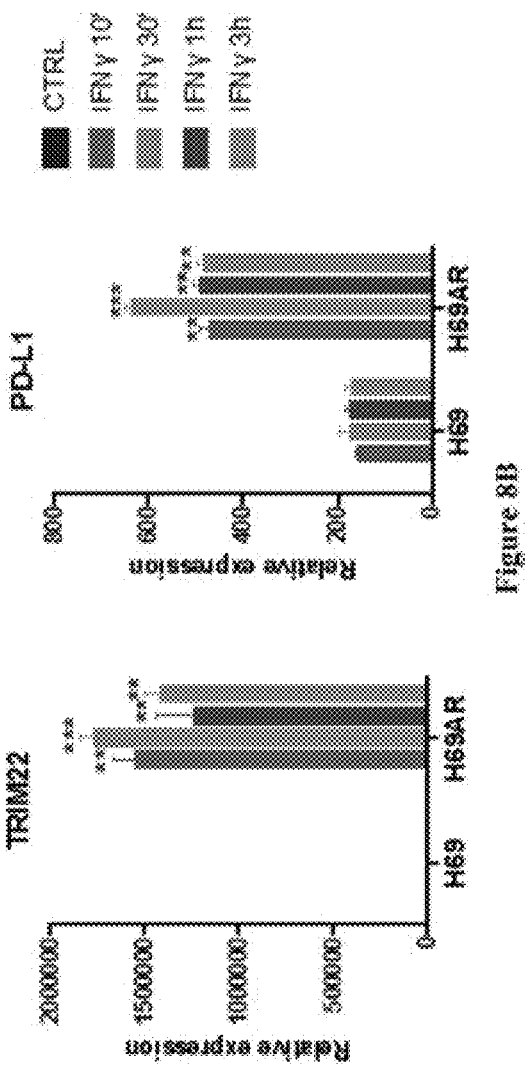
Figure 8C:
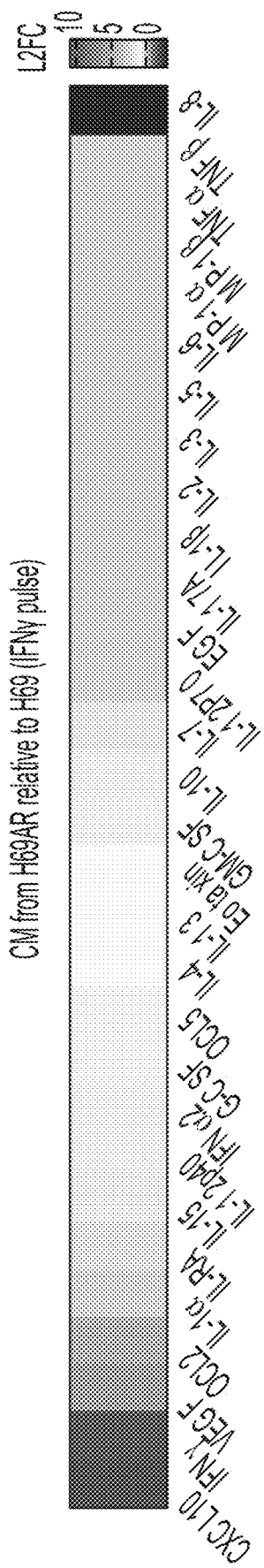
Figure 8D:
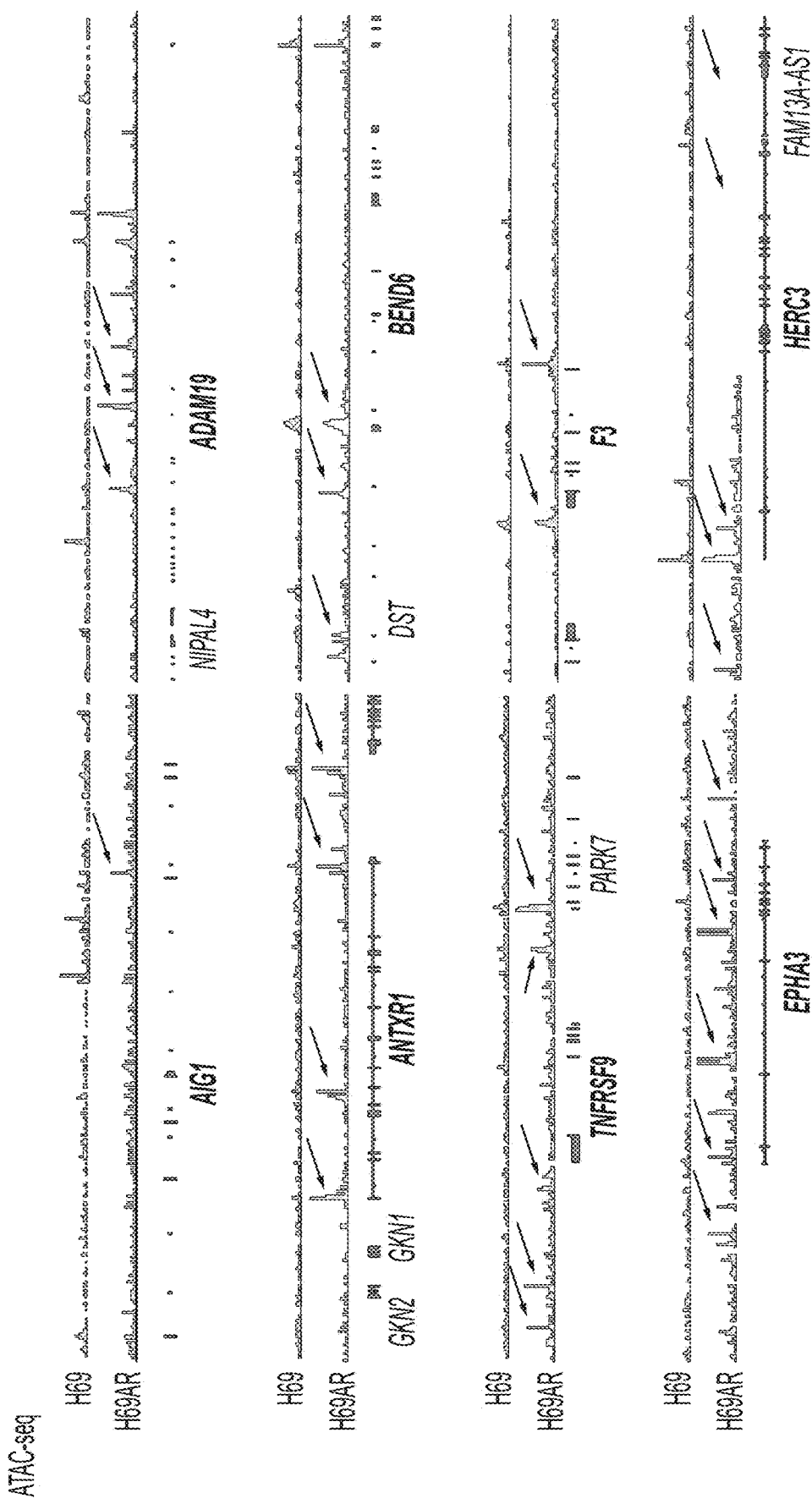
Figure 8D:
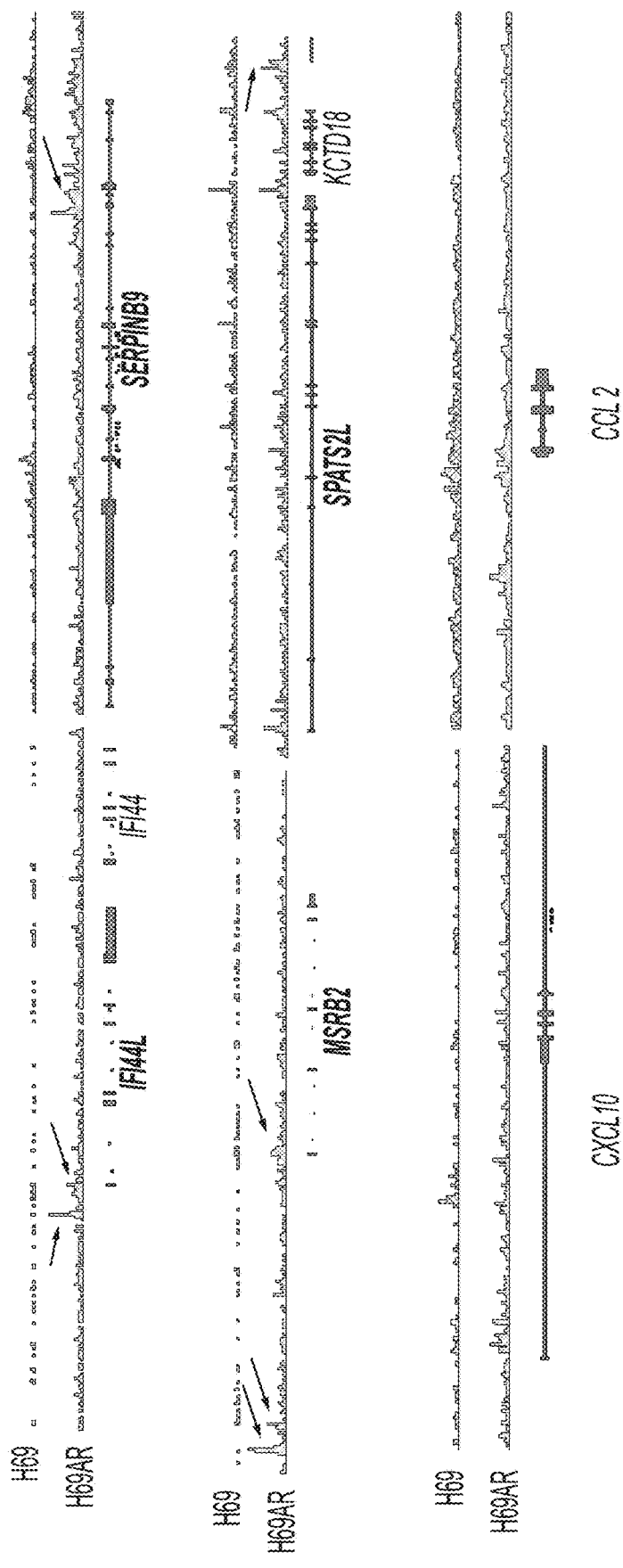
Figure 9A:
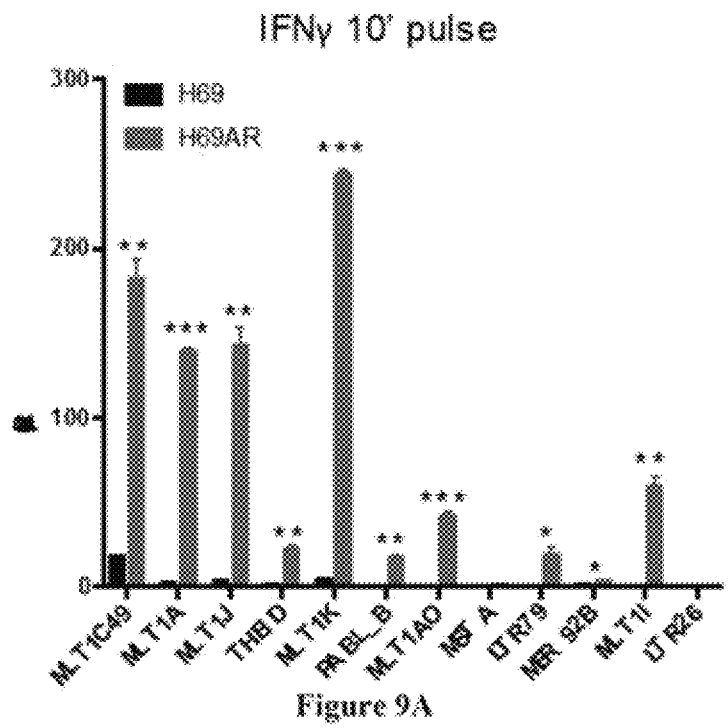
FIGS. 9A-9G show that SPARCS are silenced by EZH2 and its bidirectional transcription induces positive feedback amplification of innate immune signaling.
Figure 9B:
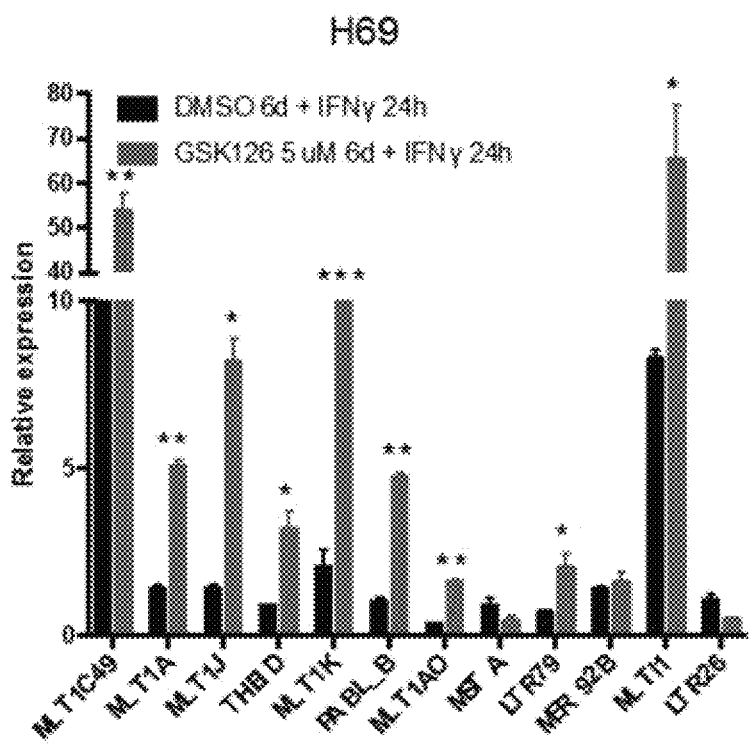

In contrast to H69M-PD-L1$^{high}$ cells, which secreted IFNγ at baseline (FIG. 1F), chemoresistant H69AR cells required exogenous IFNγ for robust PD-L1 induction (FIG. 2A) and lacked basal MLT1C49 expression (FIG. 8A). SPARCS inducibility were therefore explored by transient IFNγ pulse treatment of H69AR compared with H69 cells. Even a 10 minute IFNγ pulse resulted in marked induction of TRIM22 and MLT1C49 in H69AR cells, correlating with PD-L1 mRNA and secretion of multiple cytokines, including CXCL10 and CCL2 (FIGS. 2B, 2C, 8B and 8C). Indeed, H69AR cells showed gain of chromatin accessibility around TRIM22, TRIM38, and multiple other SPARCS loci, but not PD-L1, CXCL10 or CCL2 (FIGS. 2D and 8D). Because H69M and H69AR cells downregulated EZH2[15] (FIG. 2E), it was next tested whether EZH2 is involved in silencing SPARCS. EZH2 inhibitor treatment of H69 cells over 6 days enhanced IFNγ induced cytokine secretion (FIG. 2F), similar to IFNγ pulsed H69AR cells (FIG. 8C), and de-repressed the same SPARCS as in H69AR cells ($R^2$=0.87488) (FIGS. 2G, 9A and 9B). Thus, SPARCS loci are normally silenced and protected from IFN exposure by EZH2, but de-repressed in mesenchymal SCLC subclones.

Figure 2H:
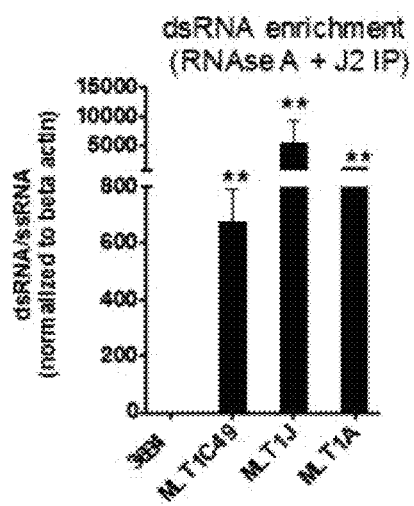
FIG. 2H: qRT-PCR of 36B4 control, MLT1C49, MLT1J and MLT1A in H69AR cells+10 min IFNγ pulse–24 h chase. RNA was treated with RNase A and immunoprecipitated with anti-dsRNA J2 antibody, values normalized against beta-actin. Mean±SD of triplicate samples shown.
Figure 2I:
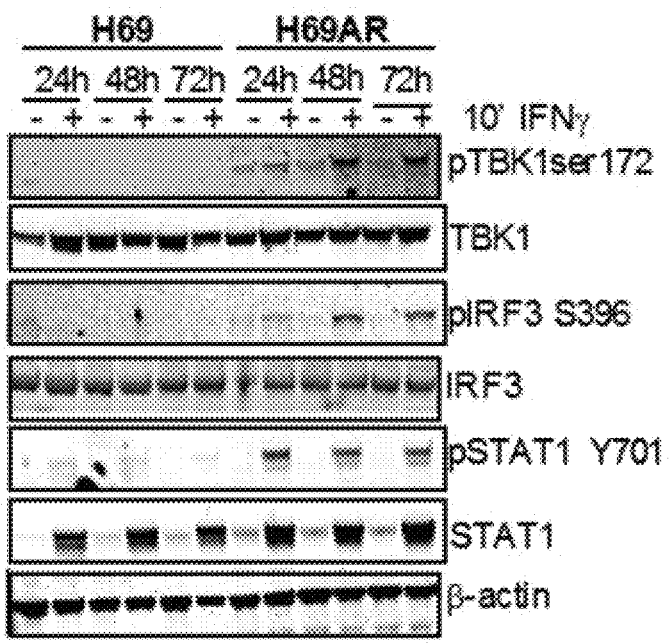
FIG. 2I: Immunoblot of pTBK1, TBK1, pIRF3, IRF3, pSTAT1, STAT1 and β-actin levels in H69 and H69AR cells±200 ng/mL IFNγ 10 min pulse –24 h chase.
Figure 2J:
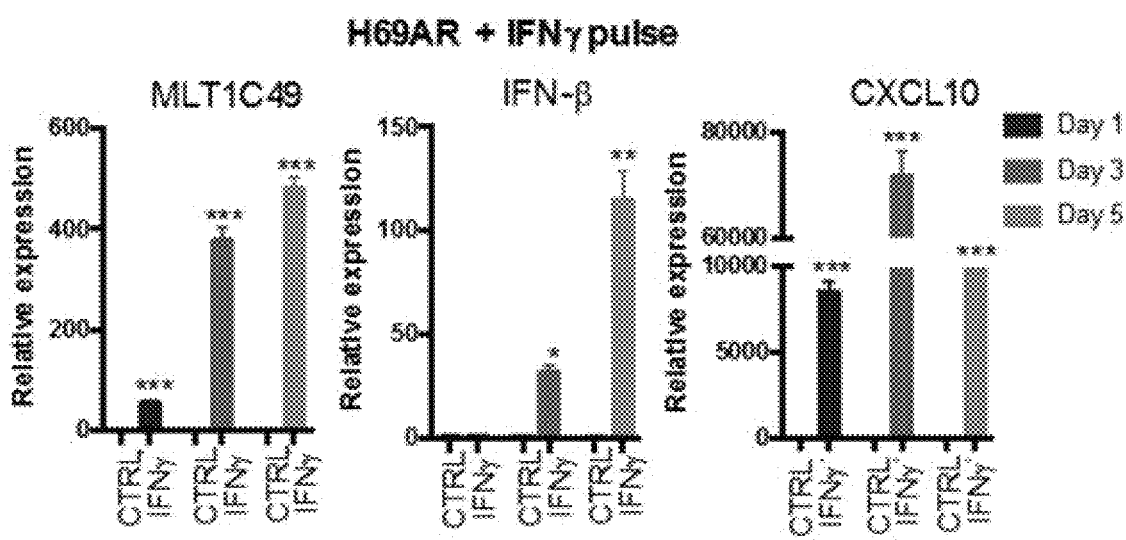
FIG. 2J: qRT-PCR of MLT1C49, IFN-β and CXCL10 in H69AR cells±10 min IFN-γ pulse–24 h chase. Mean±SD of triplicate samples shown. For each graph, from left to right are control and IFN-γ pulse at each of 1, 3, and 5 days.
Figure 9C:
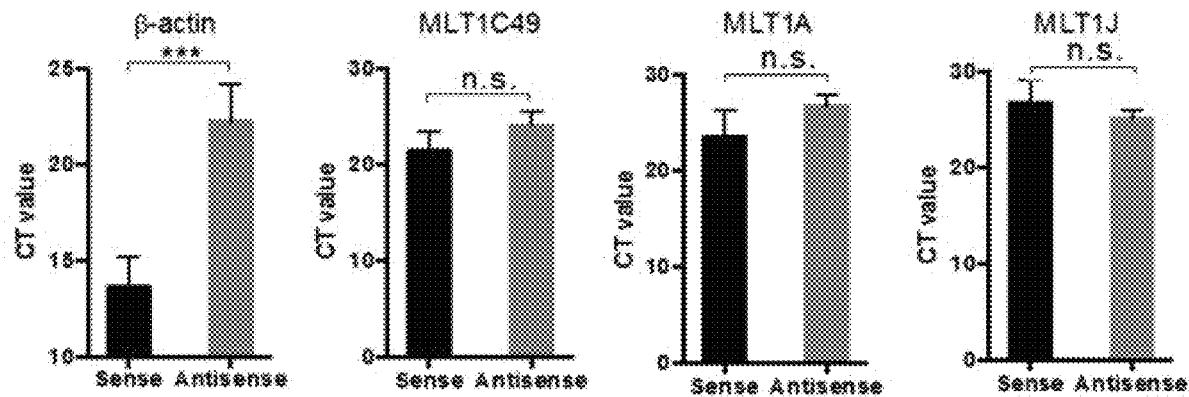
Figure 9D:
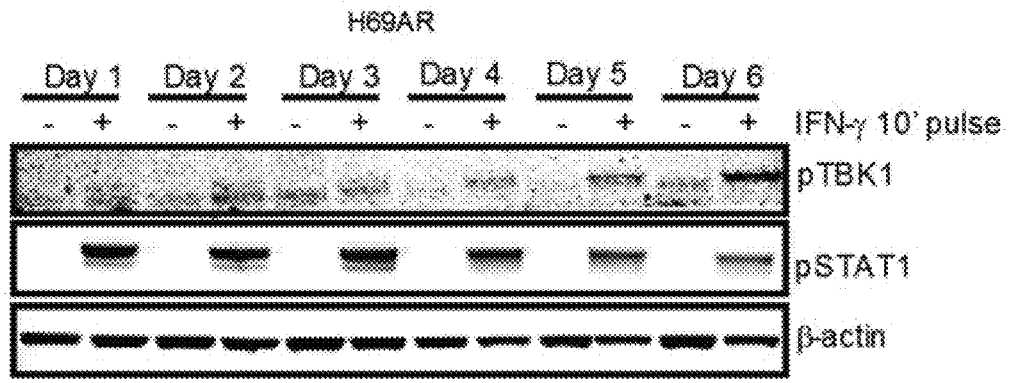
Figure 9E:
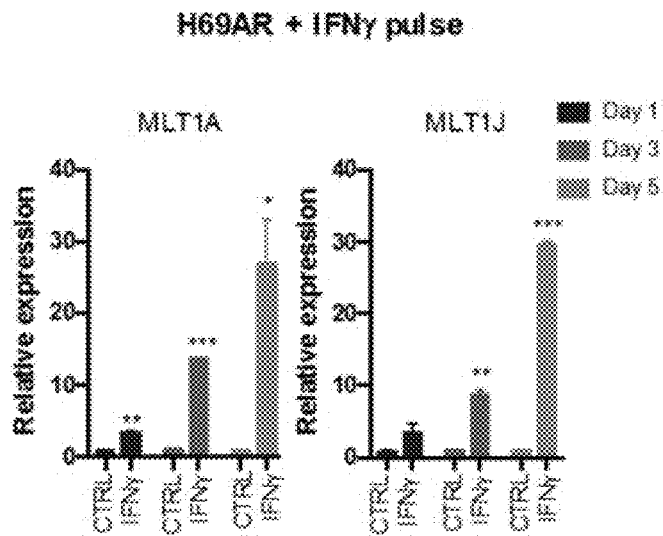
Figure 9F:
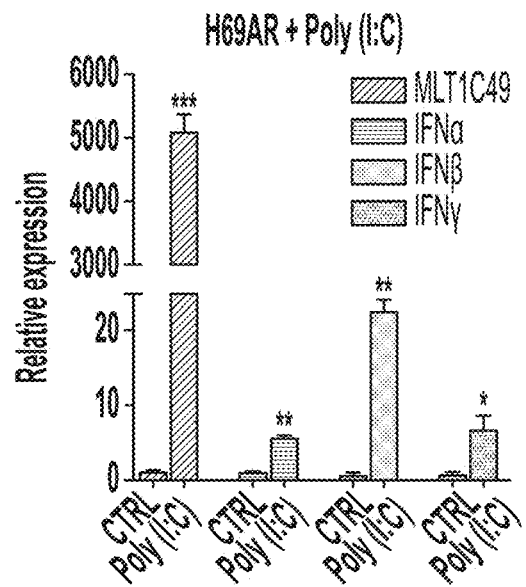
Figure 9G:
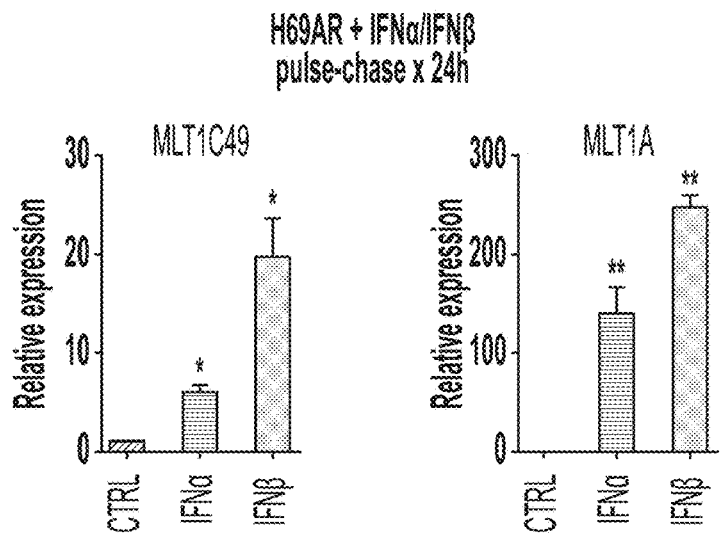

It was sought to determine if SPARCS promote positive feedback signal amplification, which would explain their propensity to be silenced. High levels of dsRNA preferentially produced from MLT1C49, MLT1J and MLT1A were detected in 10 minute IFNγ pulsed H69AR cells, even after 24 hours (FIG. 2H). TAG-aided sense/antisense transcript detection (TASA-TD) PCR[16] confirmed that dsRNA resulted from bidirectional transcription of MLT1C49, MLT1J, and MLT1A (FIG. 9C). IFNγ pulse treatment uniquely hyperactivated and sustained pTBK1 and pIRF3 in addition to pSTAT1 in H69AR but not H69 cells (FIG. 2I), which further amplified SPARCS expression, pTBK1, and its effector cytokines over time (FIGS. 2J, 9D and 9E). Induction of type I/II IFNs was also confirmed by transfection of the dsRNA mimic Poly(I:C) in H69AR cells (FIG. 9F) and SPARCS upregulation by direct IFNα/β exposure or by Poly(I:C) itself (FIGS. 9F and 9G), consistent with positive feedback induced by dsRNA and type I IFN. Furthermore, exposure of untreated H69AR cells to IFNγ primed conditioned medium also activated TBK1 and STAT1 and induced CXCL10, IFN/3 and ERV expression (FIGS. 10A-D). As expected, treatment with the JAK1/2 inhibitor Ruxolitinib disrupted this circuit, whereas TBK1/

Figure 10A:
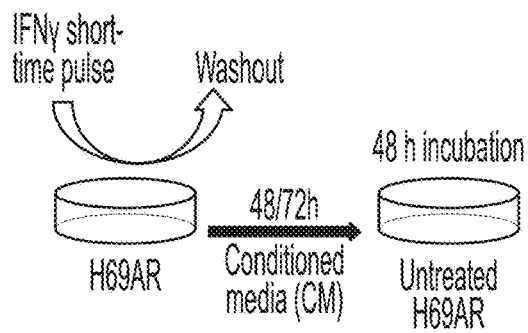
FIGS. 10A-10I show positive feedback amplification of innate immune signaling induced by IFNγ
Figure 10B:
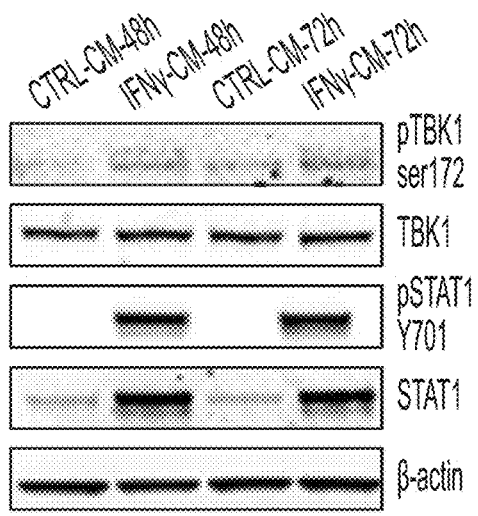
Figure 10C:
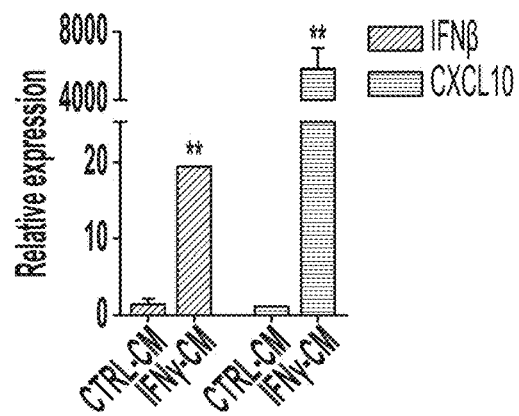
Figure 10D:
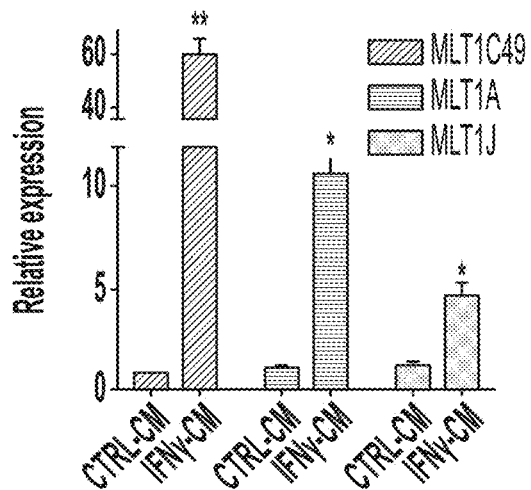
Figure 10E:
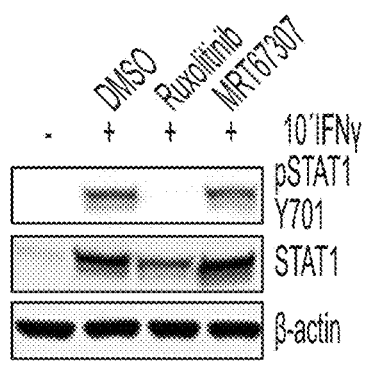
Figure 10F:
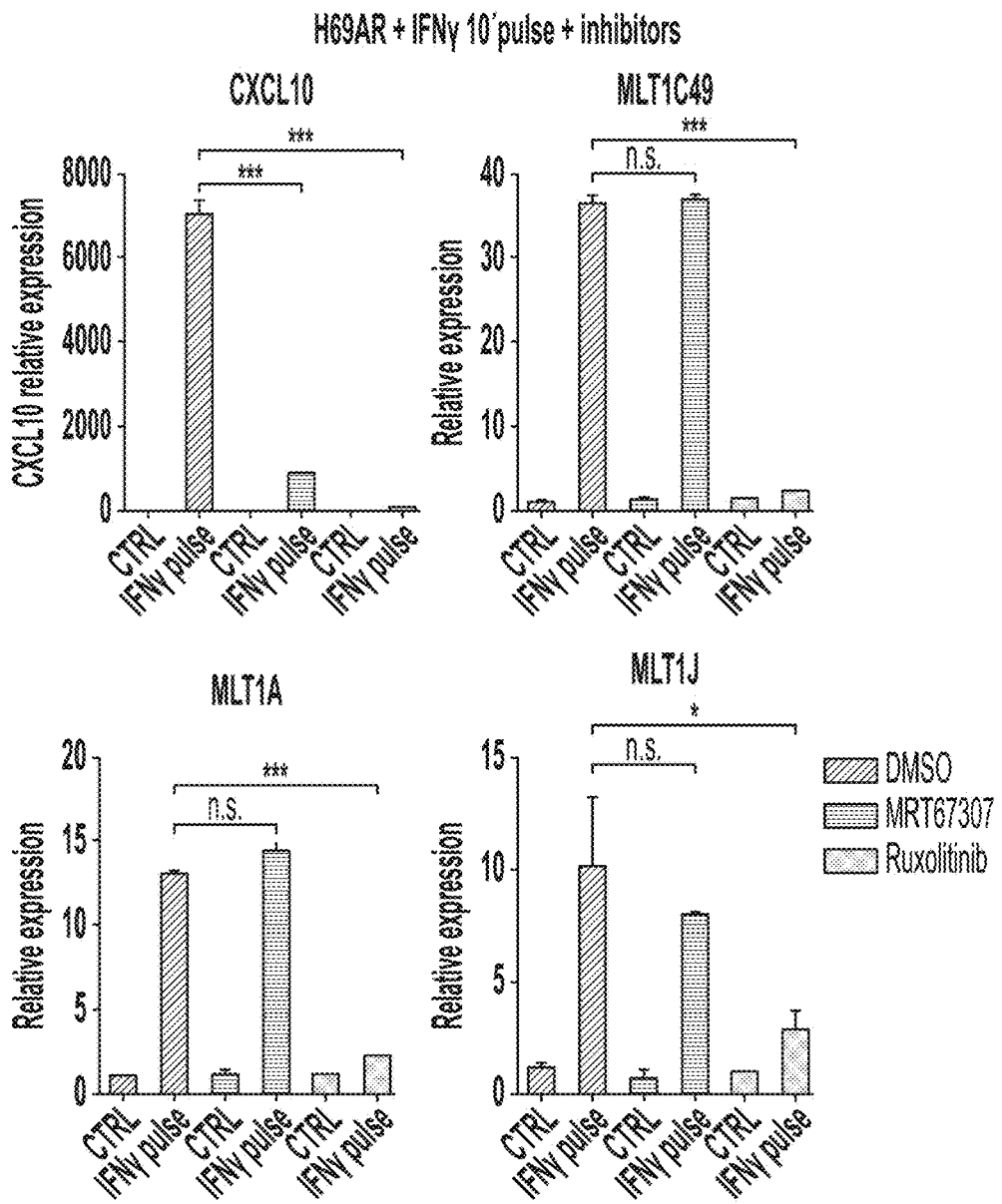
Figure 10G:
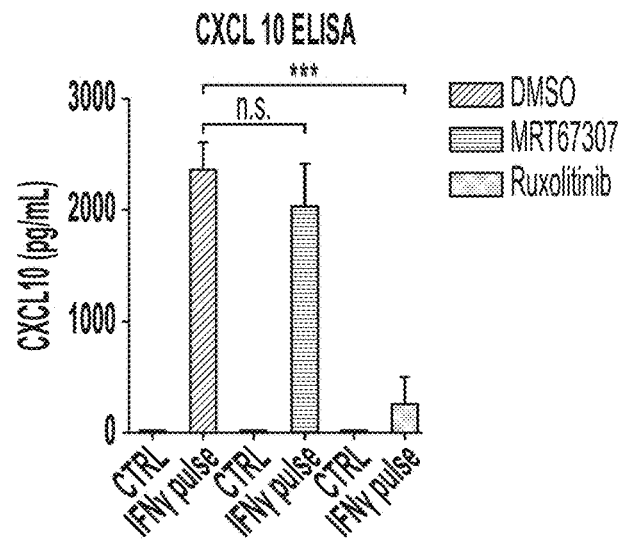

IKKκ inhibition with MRT67307, partially inhibited downstream CXCL10 expression (FIGS. 10E-G).

Figure 2K:
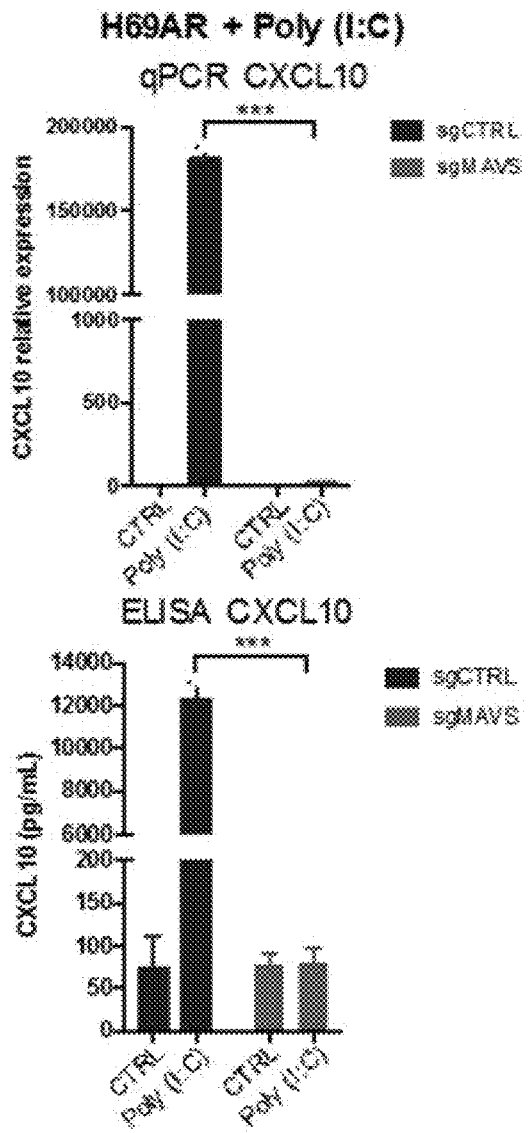
FIG. 2K: qRT-PCR and ELISA of CXCL10 in sgCTRL and sgMAVS-H69AR cells 72 h following Poly(I:C) transfection. Mean±SD of triplicate samples shown. For each graph, from left to right are control and Poly(I:C) transfection in each of sgCTRL and sgMAVS-H69AR cells.
Figure 2L:
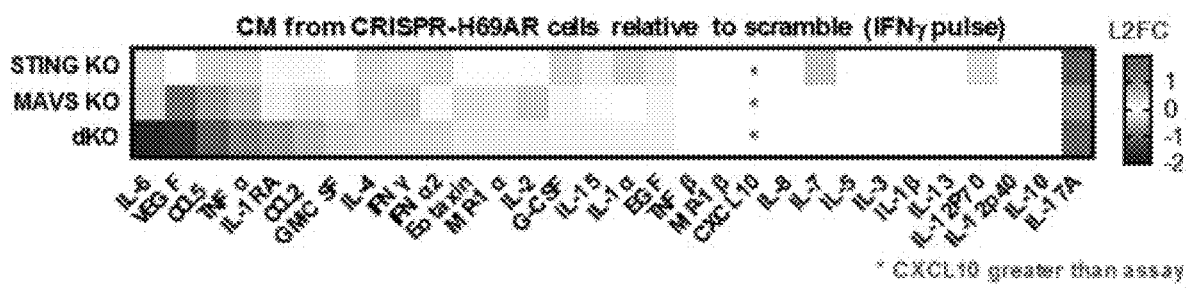
FIG. 2L: Log-2 fold change cytokine/chemokine differences in CM between CRISPR-H69AR cells after 10 min IFNγ 10 ng/mL pulse relative to sgCTRL cells (Scramble).
Figure 2M:
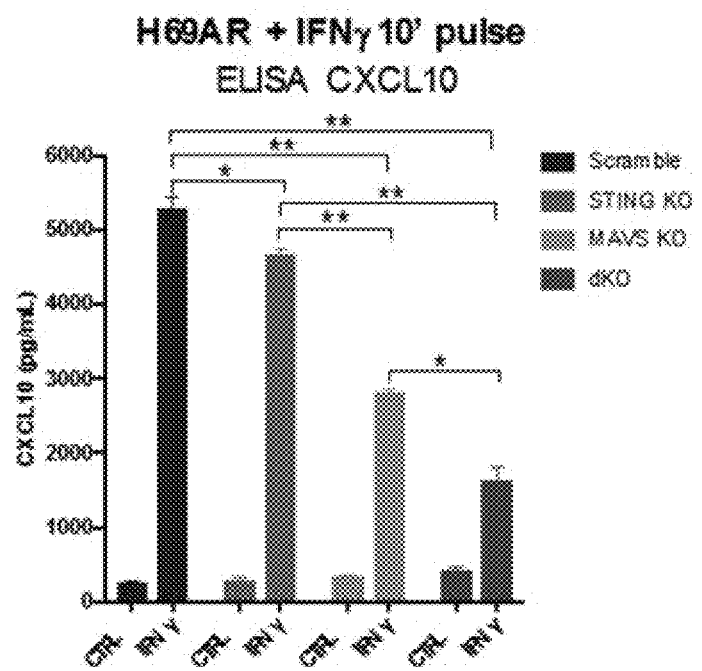
FIG. 2M: CXCL10 ELISA in Scramble, STING KO, MAVS KO and dKO H69AR CM following 10 min IFNγ 10 ng/mL pulse and chase for 3 days. Mean±SD of triplicate samples shown. From left to right are control and IFNγ 10 ng/mL pulse in each of Scramble, STING KO, MAVS KO and dKO.
Figure 2N:
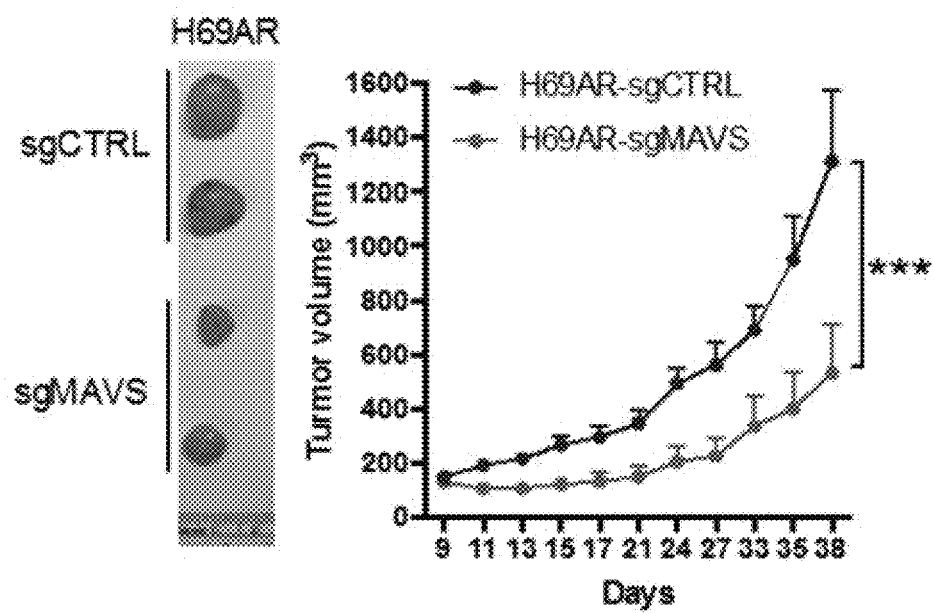
Figure 10H:
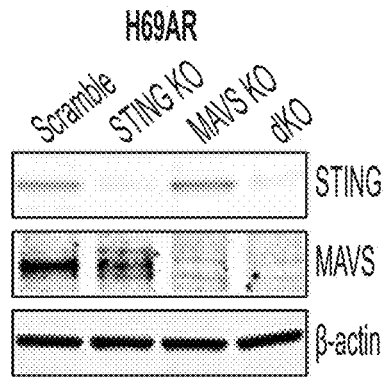
Figure 10I:
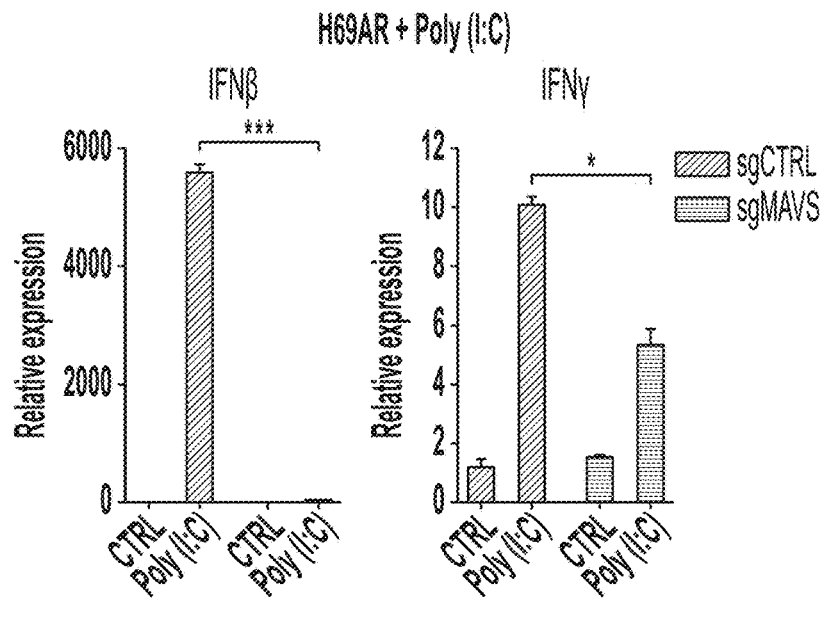

The contribution of SPARCS ERV sensing to feedforward signaling in H69AR cells was also directly assessed. As expected, MAVS deletion impaired Poly(I:C)-induced CXCL10 and type I/II IFN expression and CXCL10 secretion (FIGS. 2K, 10H, and 10I). MAVS and especially MADS/STING knockout (KO) H69AR cells downregulated multiple cytokines/chemokines following low dose IFNγ pulse treatment including CXCL10 as well as VEGF (FIGS. 2L and 2M). Tumorigenicity of sgMAVS-H69AR cells in nude mice was thus also significantly impaired relative to control (FIG. 2N).

Figure 11A:
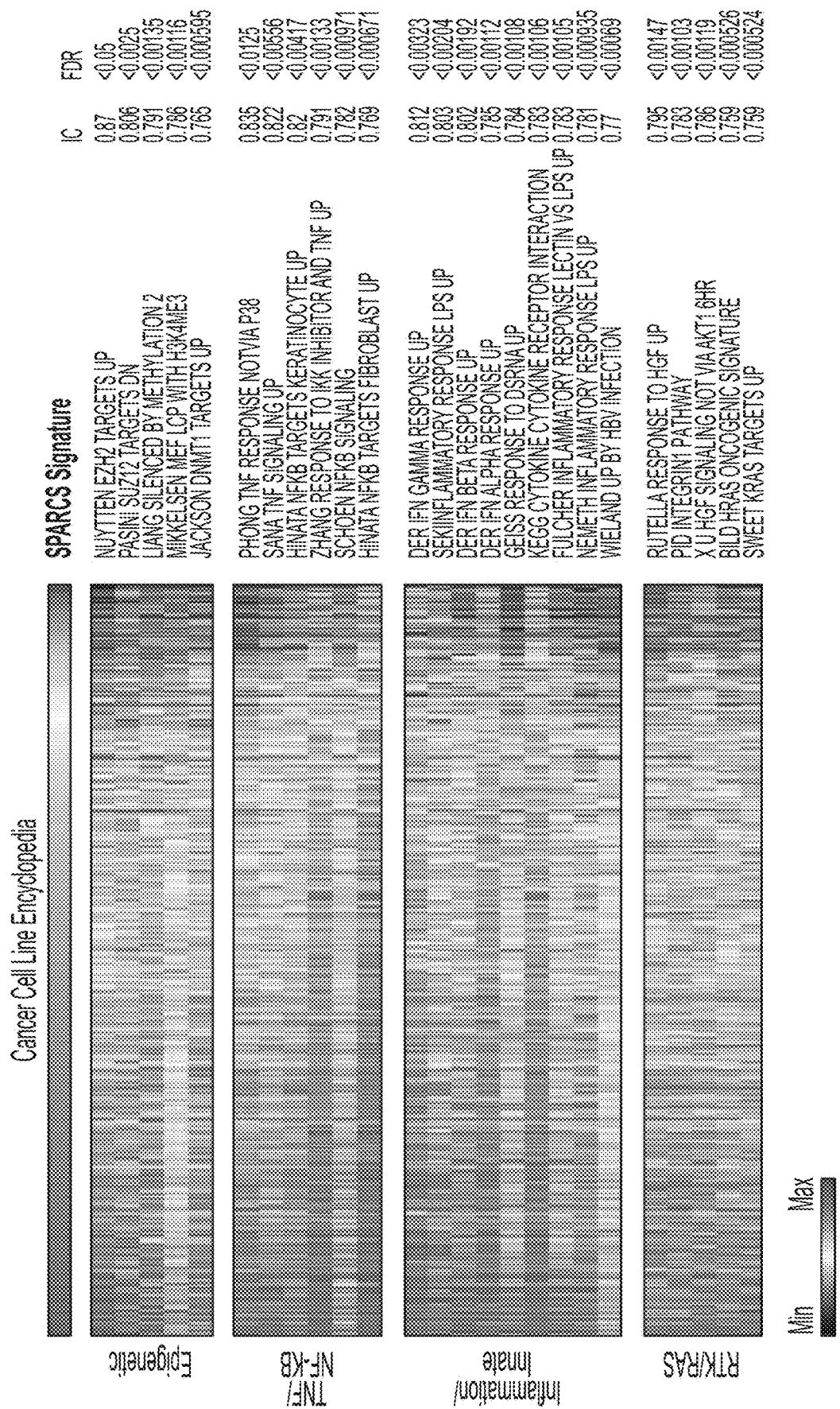
FIGS. 11A-11B show that SPARCS positively correlates with epigenetic de-repression, TNF/NF-κB, inflammation/innate immunity, and RTK/KRAS signaling (FIG. 11A) ssGSEA of SPARCS signature across CCLE (n=585 cell lines) and significantly associated gene sets grouped based on biological annotations. IC=information coefficient. FDR=false discovery rate.
Figure 11B:
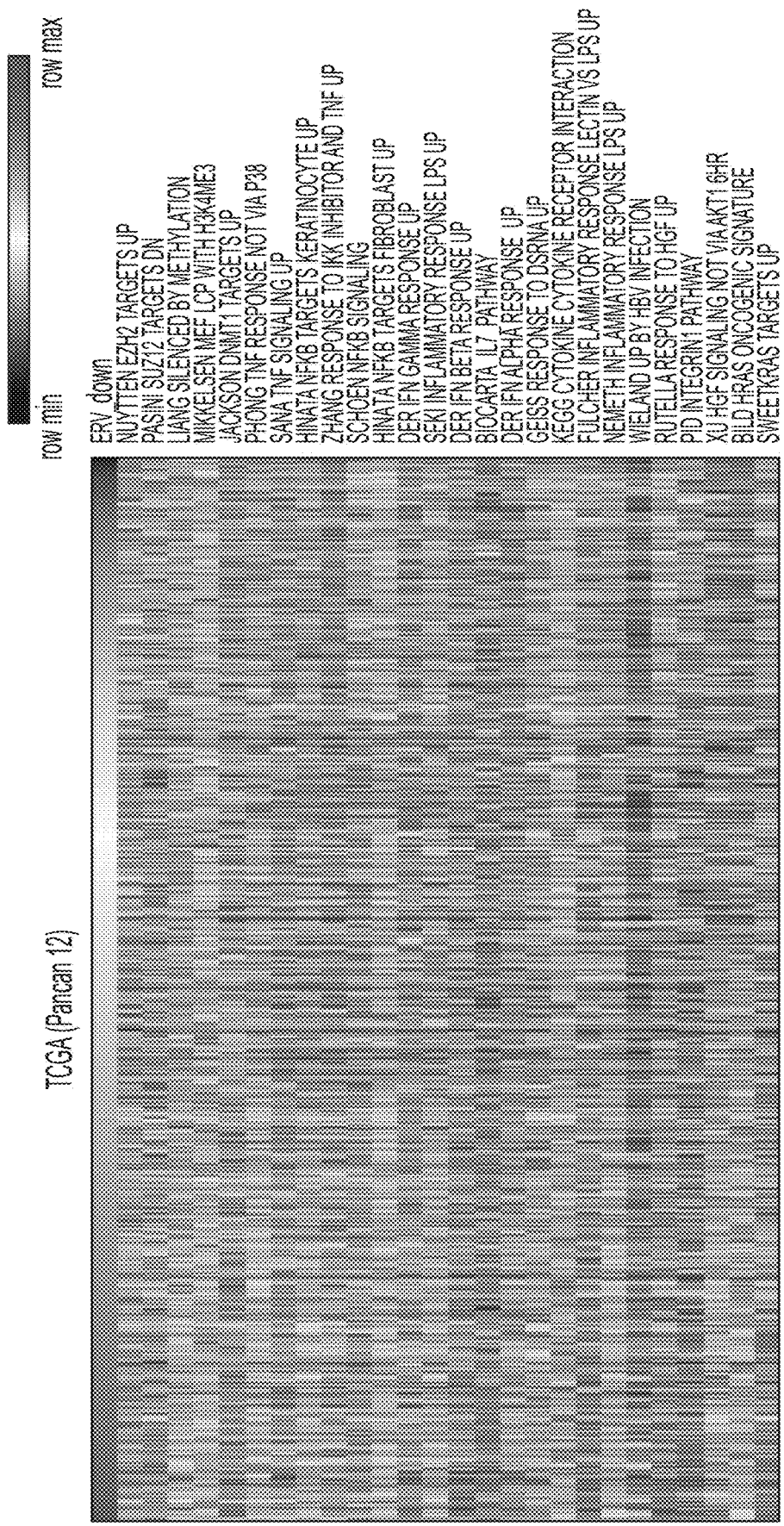
Figure 12B:
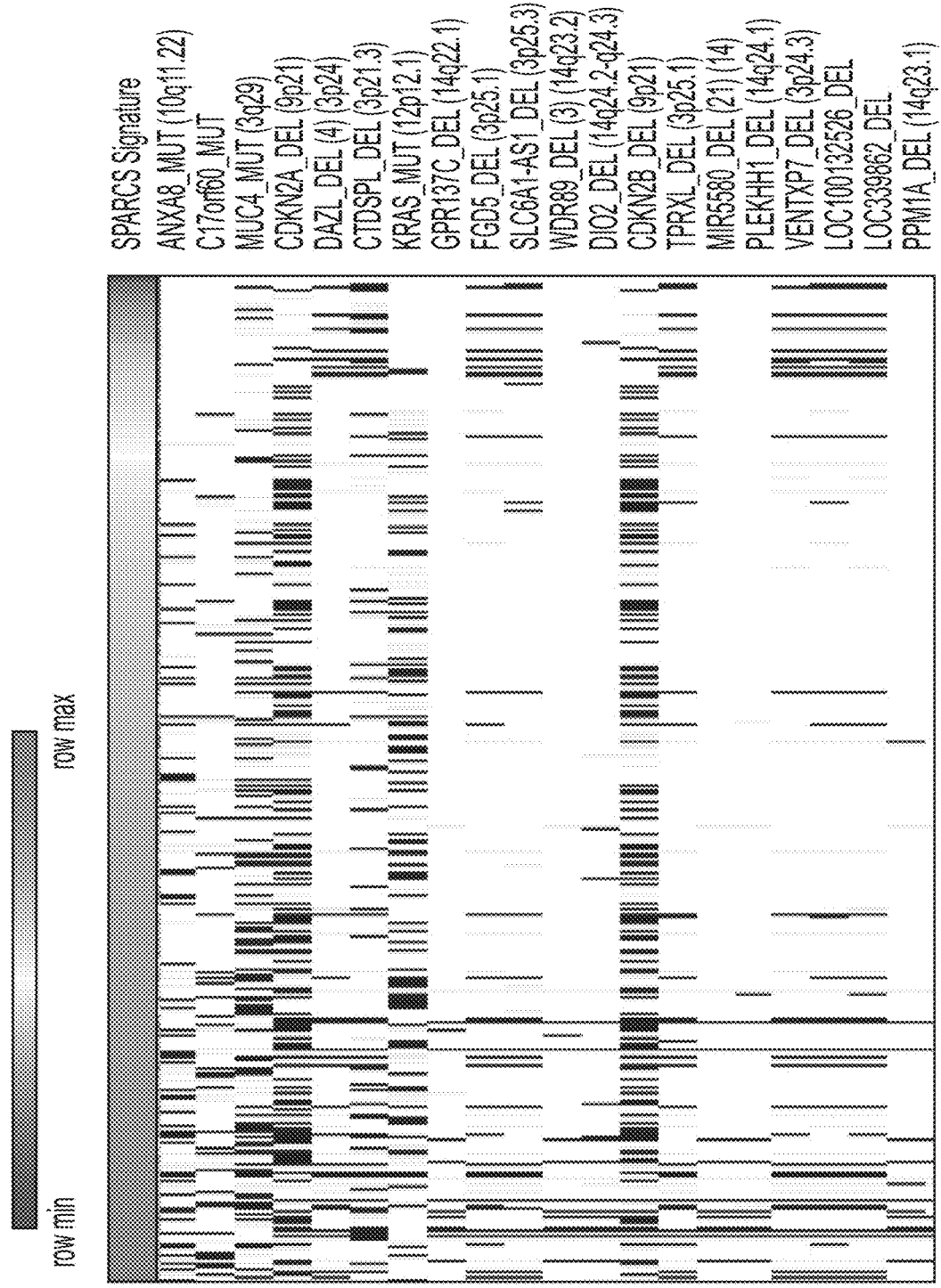

To determine the broader relevance of SPARCS and to begin to explore the relationship to immune contexture, next the expression of the 15 gene SPARCS signature across the Cancer Genome Atlas (TCGA) (Pancan12, n=3602 tumors) [17] was ranked using single sample gene set enrichment analysis (ssGSEA) 18 (FIG. 3A). Top gene sets co-enriched with SPARCS (p<0.01, FDR<0.01) included epigenetic, TNF/NF-κB, inflammation/innate immunity, and RTK/KRAS signaling (FIG. 3A), also observed in the Cancer Cell Line Encyclopedia (CCLE) (FIG. 11A and). In contrast, none of these signatures correlated with 3' UTR antisense ERVs from H69M downregulated genes (FIG. 11B). The SPARCS$^{high}$ state also co-associated with mutations on chromosome 3p, including PBRM1 and SETD2, as well as oncogenic KRAS in CCLE (FIGS. 12A and B).

Figure 3B:
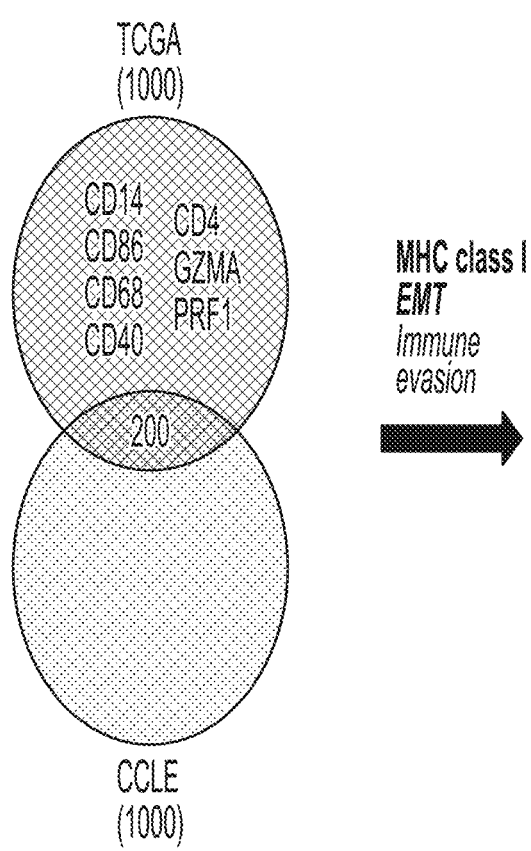
Figure 12C:
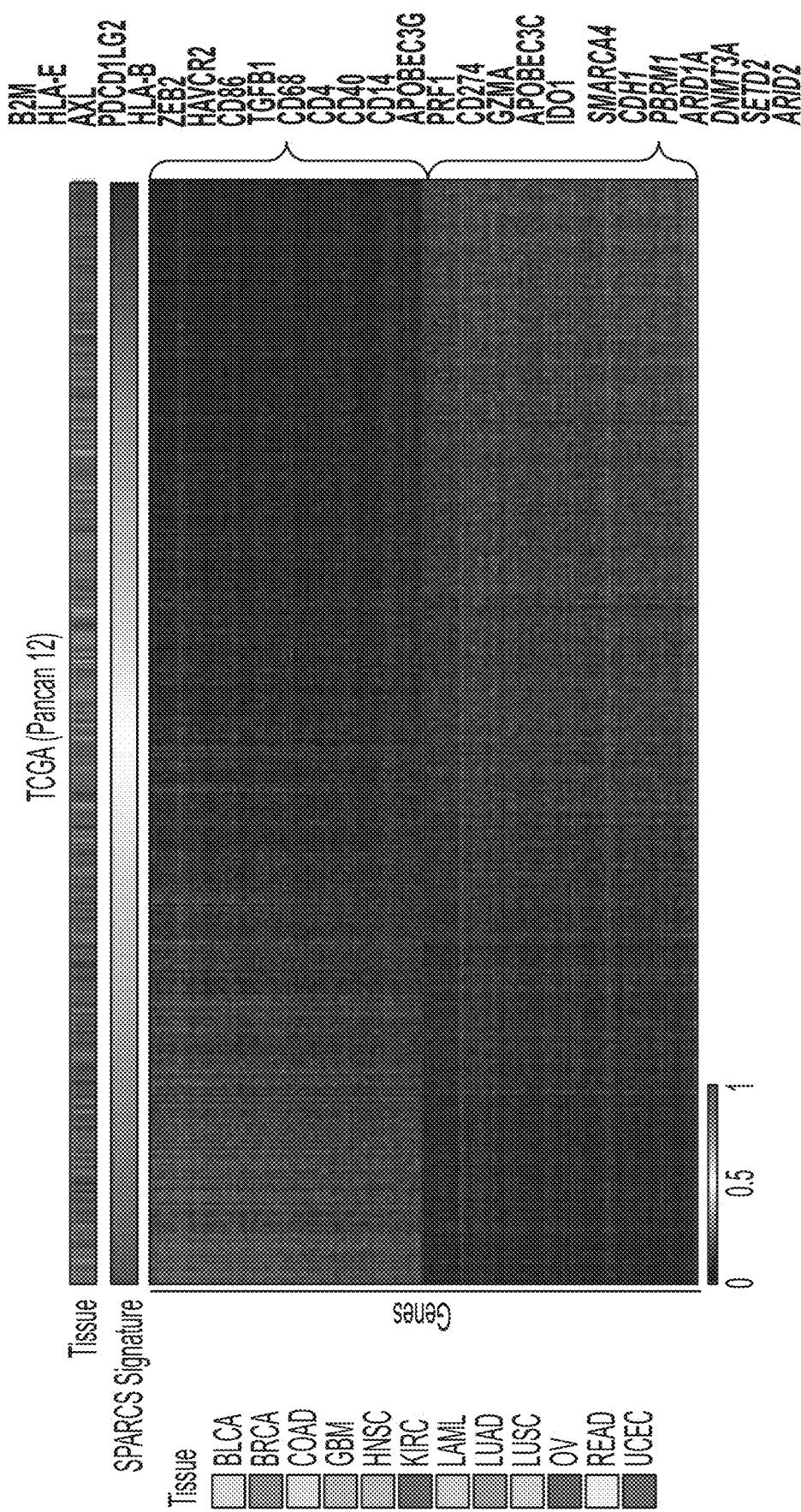
Figure 12D:
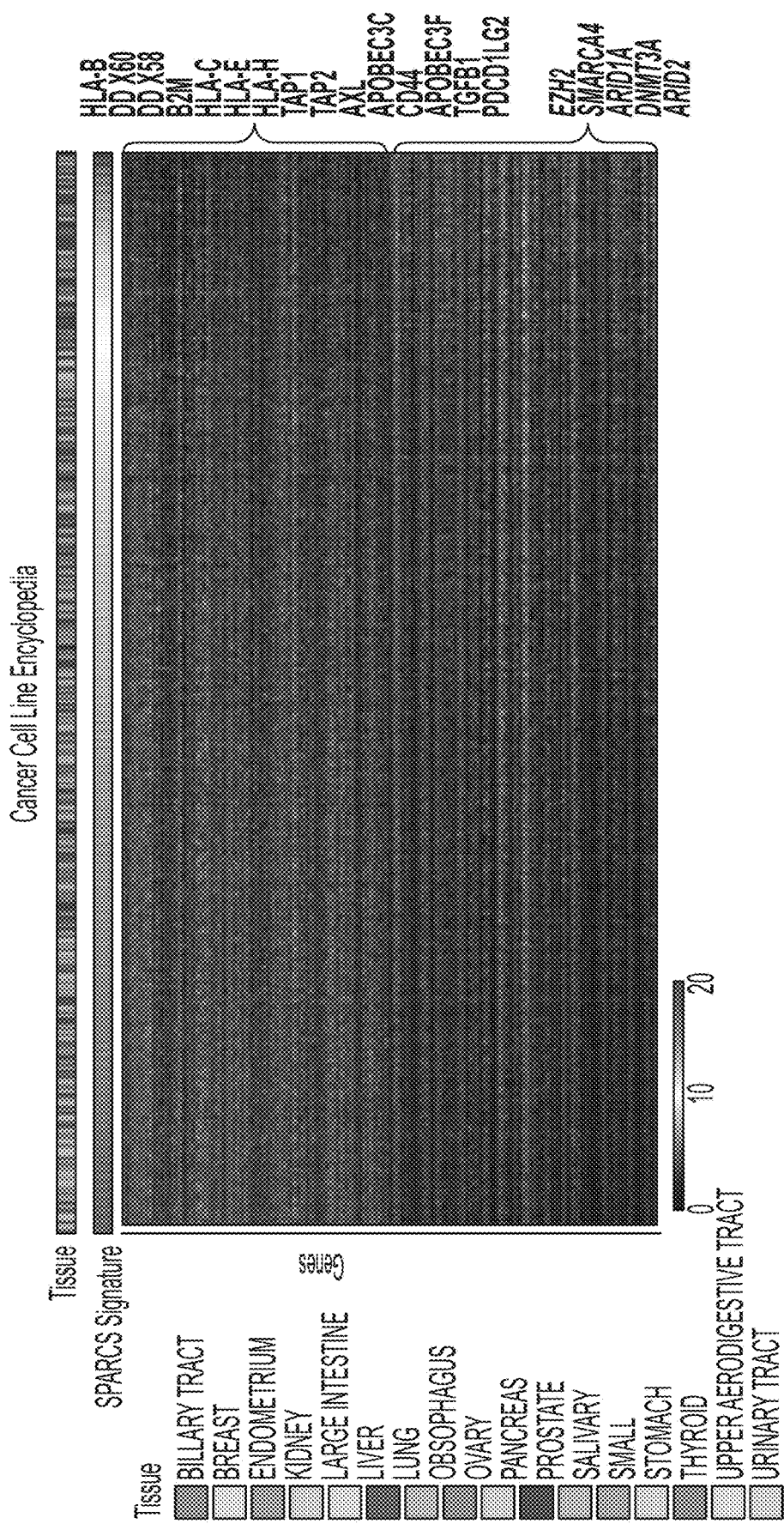

At the gene level, SPARCS expression correlated with markers of T cell (CD4, PRF1 and GZMA) and myeloid (CD40, CD86, CD14, CD68) infiltration uniquely in TCGA. In both CCLE and TCGA datasets SPARCS associated with expression of MHC, APOBEC, immunosuppressive factors such as CD274 (PD-L1), PDCD1LG2 (PD-L2), C10orf54 (VISTA), TIM3, and IDO1, and EMT genes (FIGS. 12C and 12D). Expression of EZH2, DNMT3A, SETD2 and multiple SWI/SNF genes was inversely correlated with SPARCS in both datasets (FIGS. 12C and 12D). The top 1000 genes from TCGA and CCLE were next intersected, to isolate robust cancer cell autonomous genes co-regulated with SPARCS (FIG. 3B). This identified B2M as the top ranked gene, followed by multiple MHC class 1 (HLA-A, B, C, E, F) and class 1 related buytyrophilin (BTN) genes[19], cytosolic RNA sensors (IFIH1/MDA5, DDX60) and the antigen processing machinery (PSMB9, TAP1, TAP2), all markers of a virally infected state (FIG. 3B). TGFB1 and AXL were also top hits in this analysis (FIG. 3B).

Figure 3C:
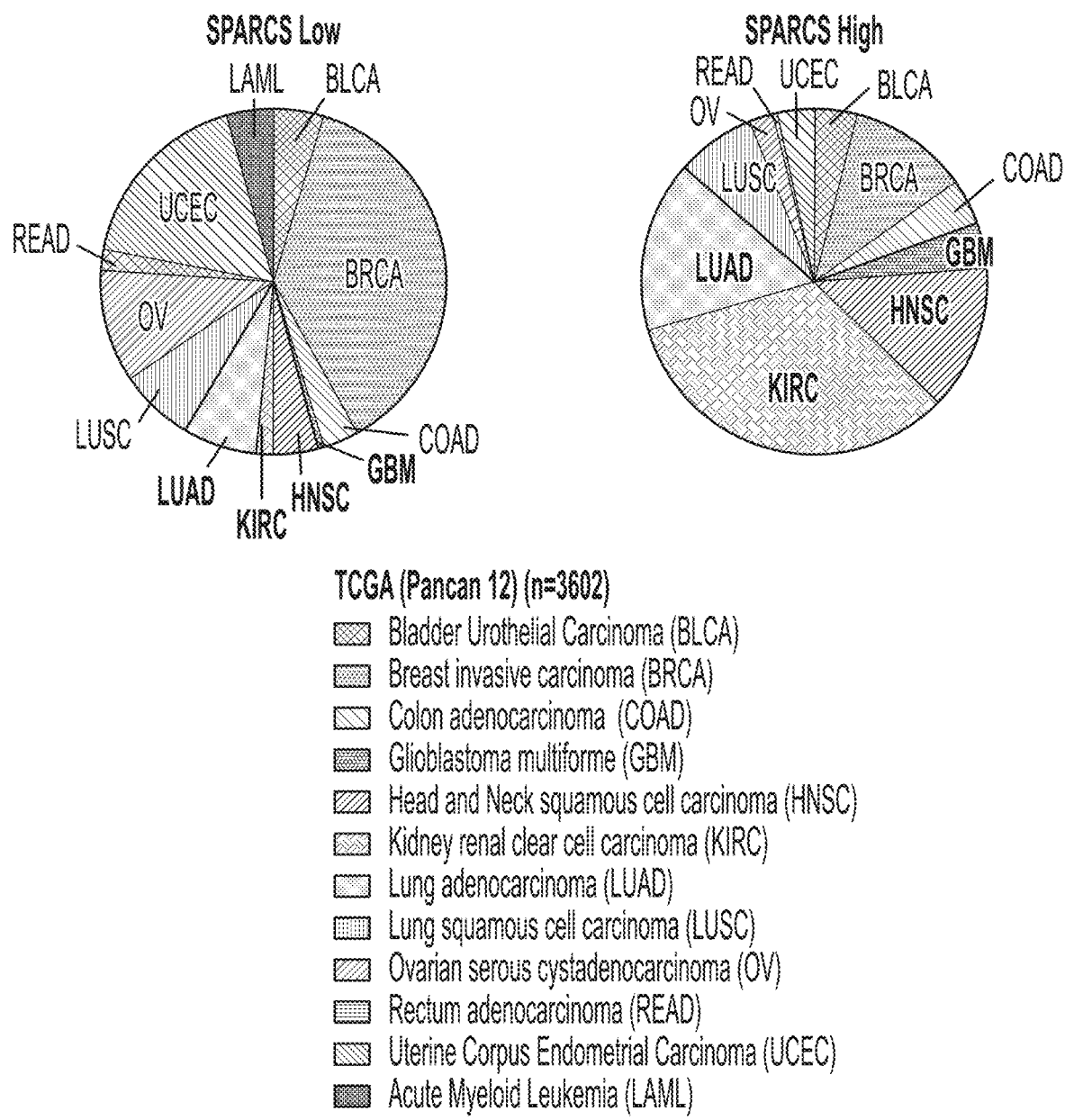
Figure 3D:
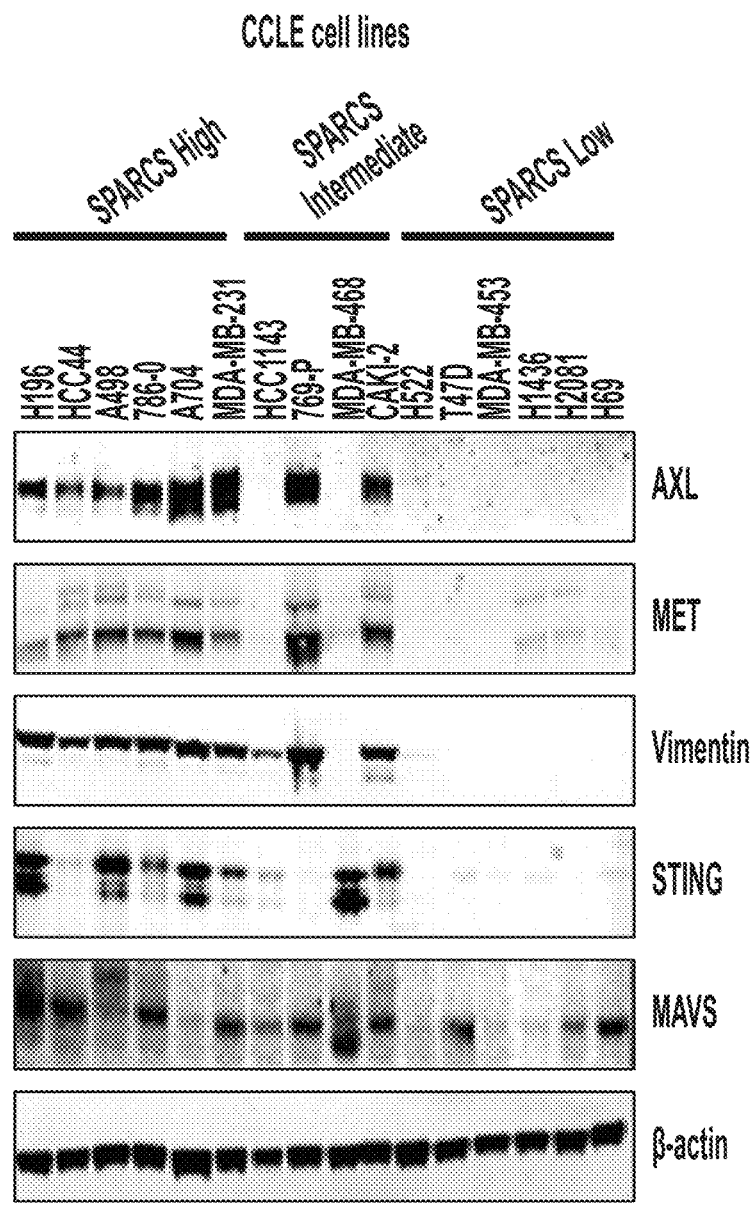
Figure 3E:
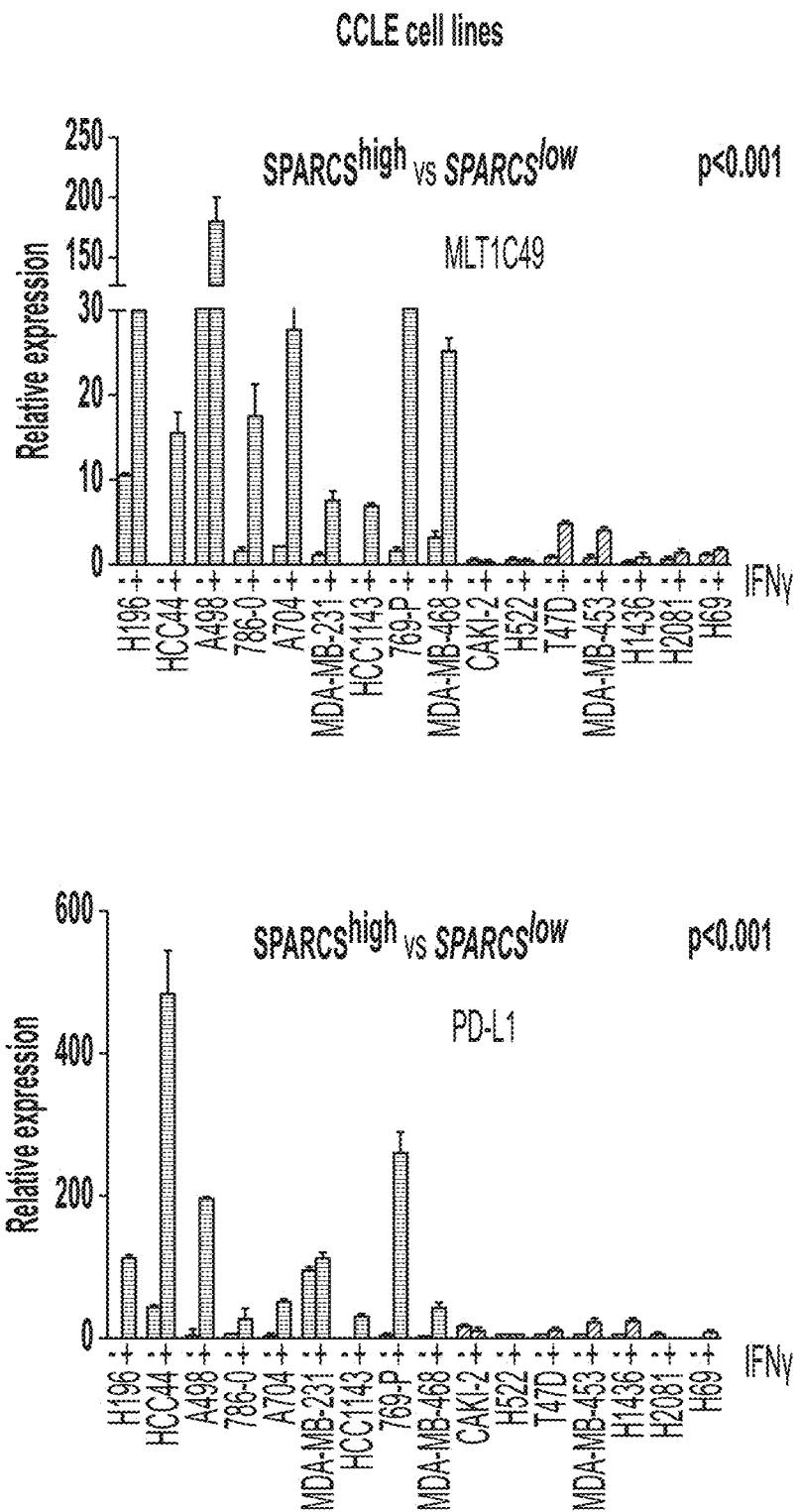
Figure 3E:
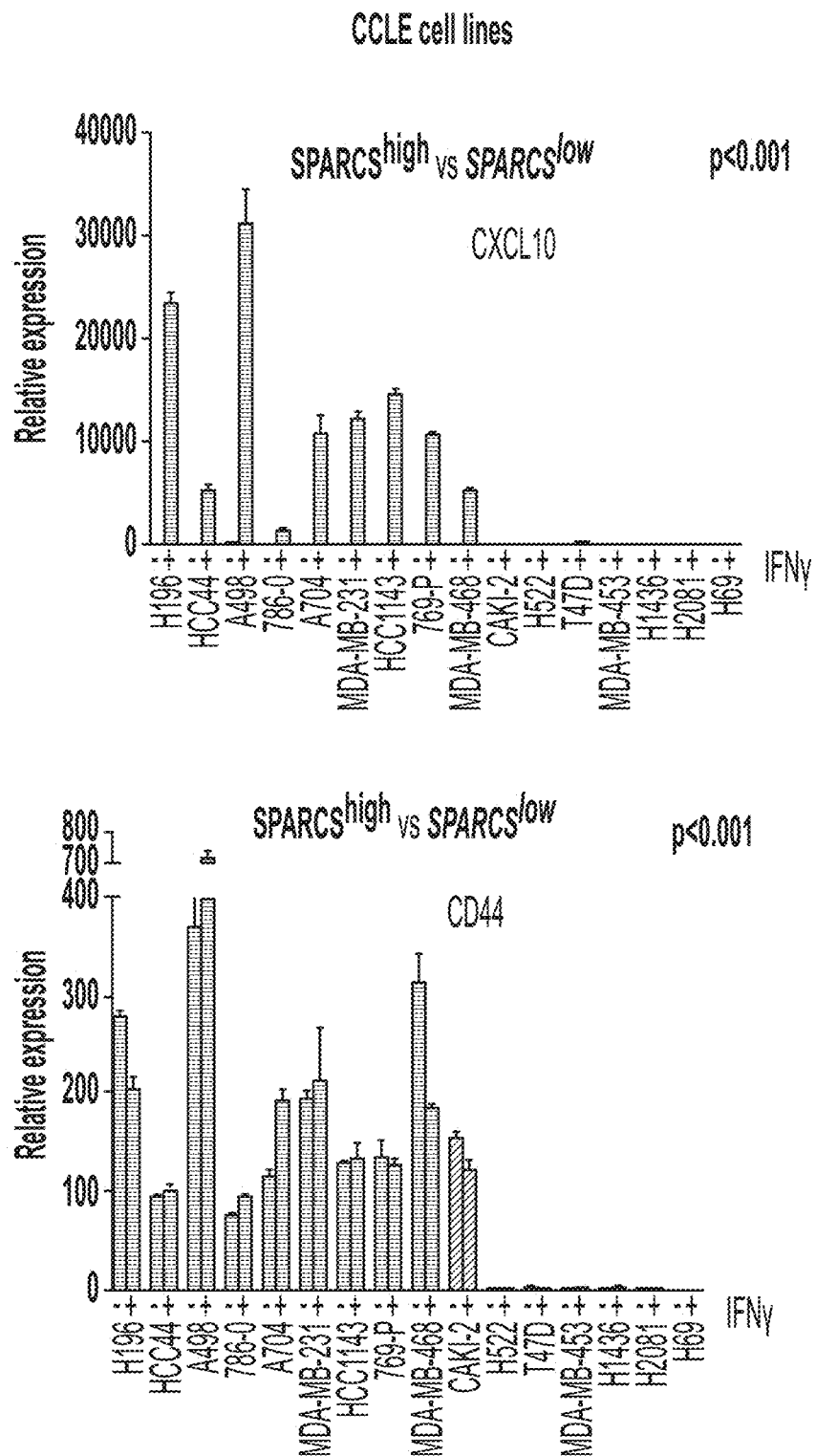
Figure 13A:
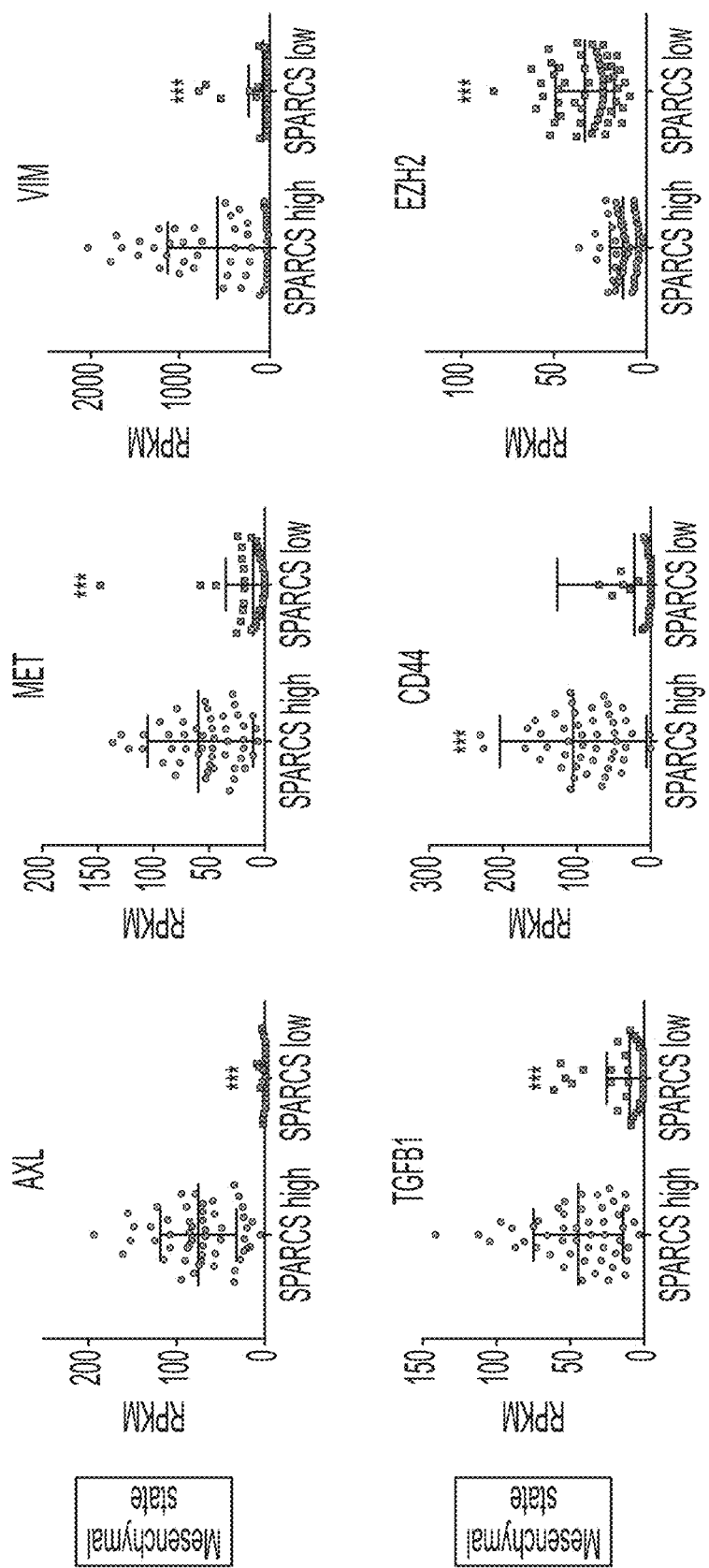
FIGS. 13A-13B show expression of mesenchymal markers and loss of EZH2 and multiple SWI/SNF components in SPARCS$^{high}$ cell lines.
Figure 13A:
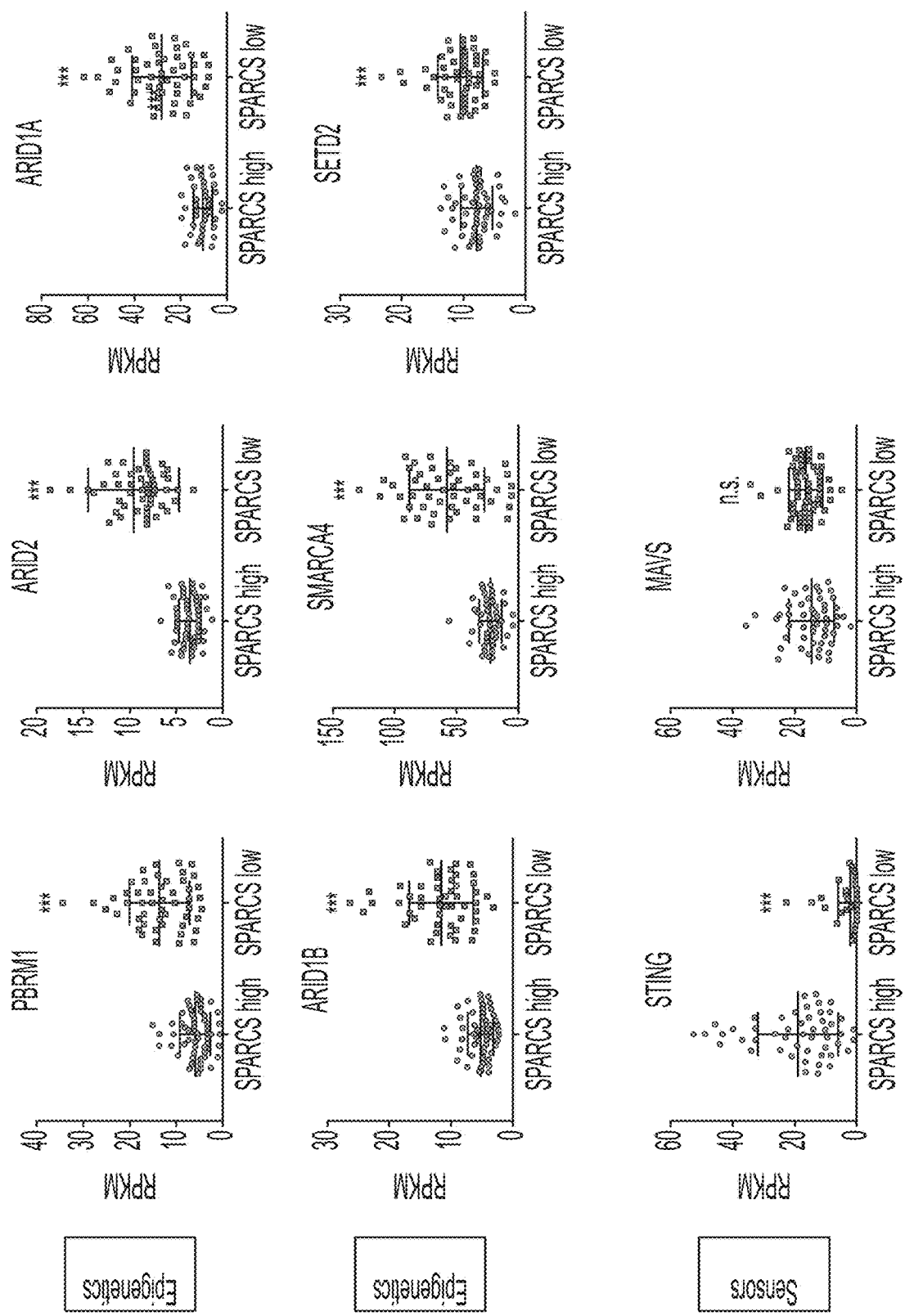
Figure 13B:
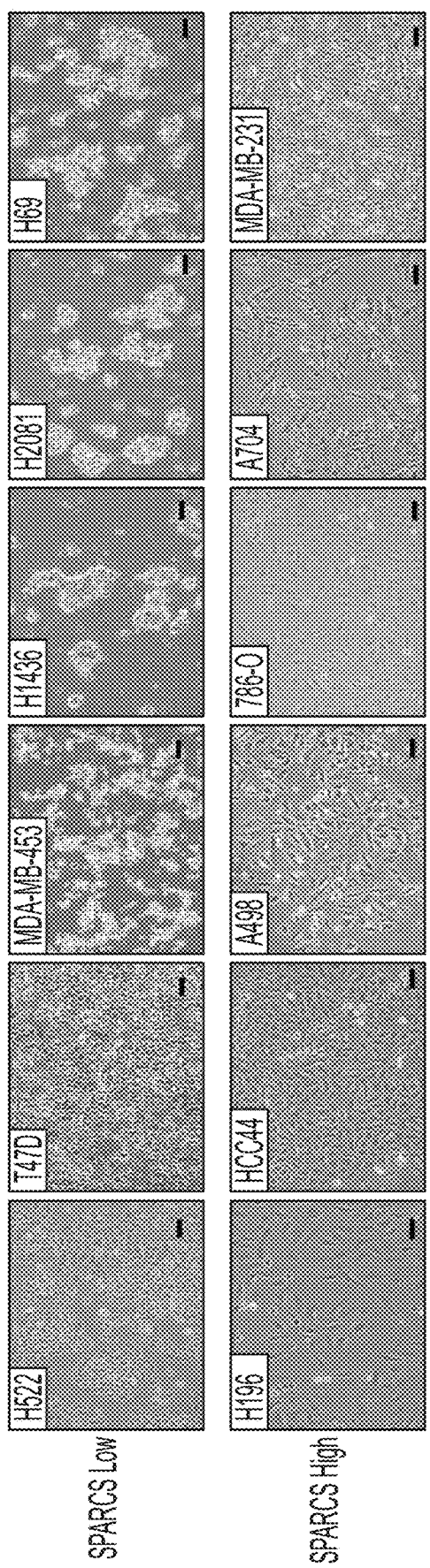
Figure 14A:
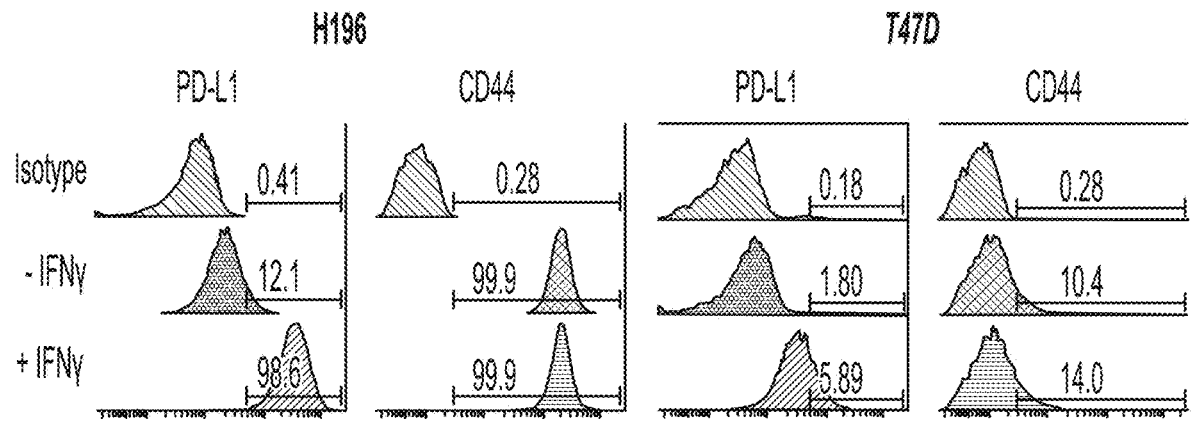
FIGS. 14A-14E show that inducible surface PD-L1 correlates with high baseline CD44 expression in SPARCS$^{high}$ cell lines and Poly (I:C) treatment of NSCLC PDOTS with de-repressed SPARCS markedly enhances CXCL10 production and sensitizes them to PD-1 blockade.

High SPARCS expression in TCGA was enriched in distinct cancer histologies beyond SCLC, including clear cell renal (KIRC), lung adenocarcinoma (LUAD), head/neck squamous (HNSC), and glioblastoma (GBM) (FIG. 3C). SPARCS$^{high}$ CCLE lines also included triple negative breast cancer (TNBC), and exhibited high relative expression of AXL, MET, VIM, TGFB1 and CD44, and low EZH2, SETD2 and SWI/SNF component expression (FIG. 13A). To validate these findings, multiple cell lines were cultured, confirming that SPARCS$^{high}$ cells exhibited mesenchymal morphology and elevated AXL, MET and Vimentin relative to SPARCS$^{low}$ cells (FIGS. 3D and 13B). Similar to the H69 model, SPARCS$^{high}$ cells also exhibited increased STING levels, whereas MAVS was more evenly expressed (FIGS. 3D and 13A). It was further confirmed that IFNγ pulse treatment of SPARCS$^{high}$ cells significantly induced MLT1C49, CXCL10 and PD-L1 expression relative to SPARCS$^{low}$ cells, and inducible surface PD-L1 correlated with their high baseline CD44 expression (FIGS. 3E and 14A).

Figure 4A:
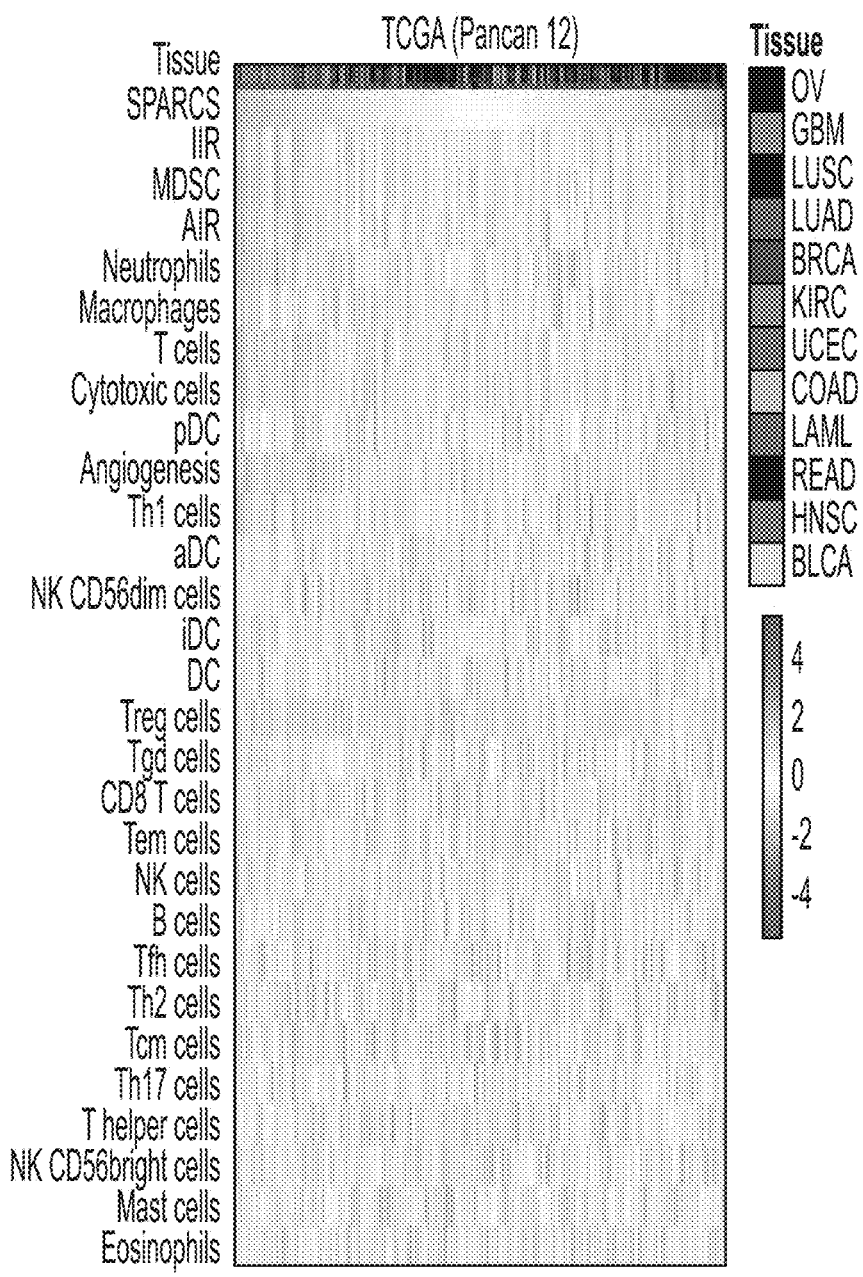
Figure 4B:
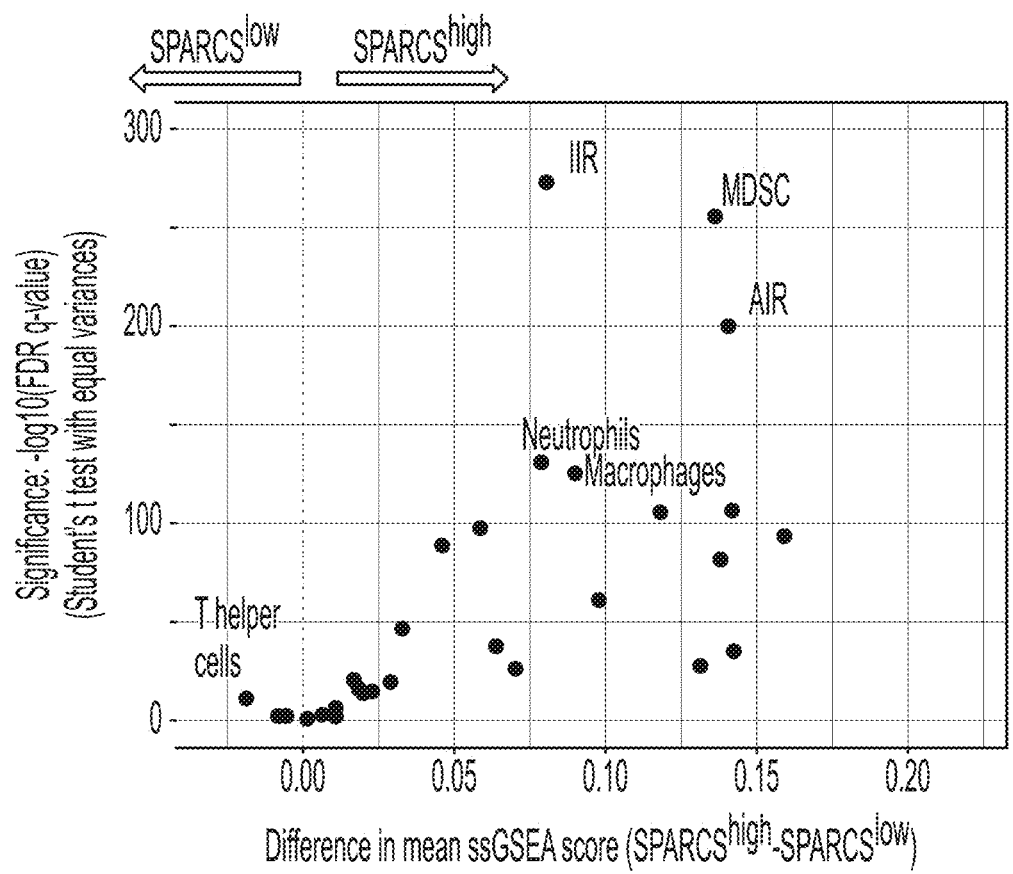
Figure 4F:
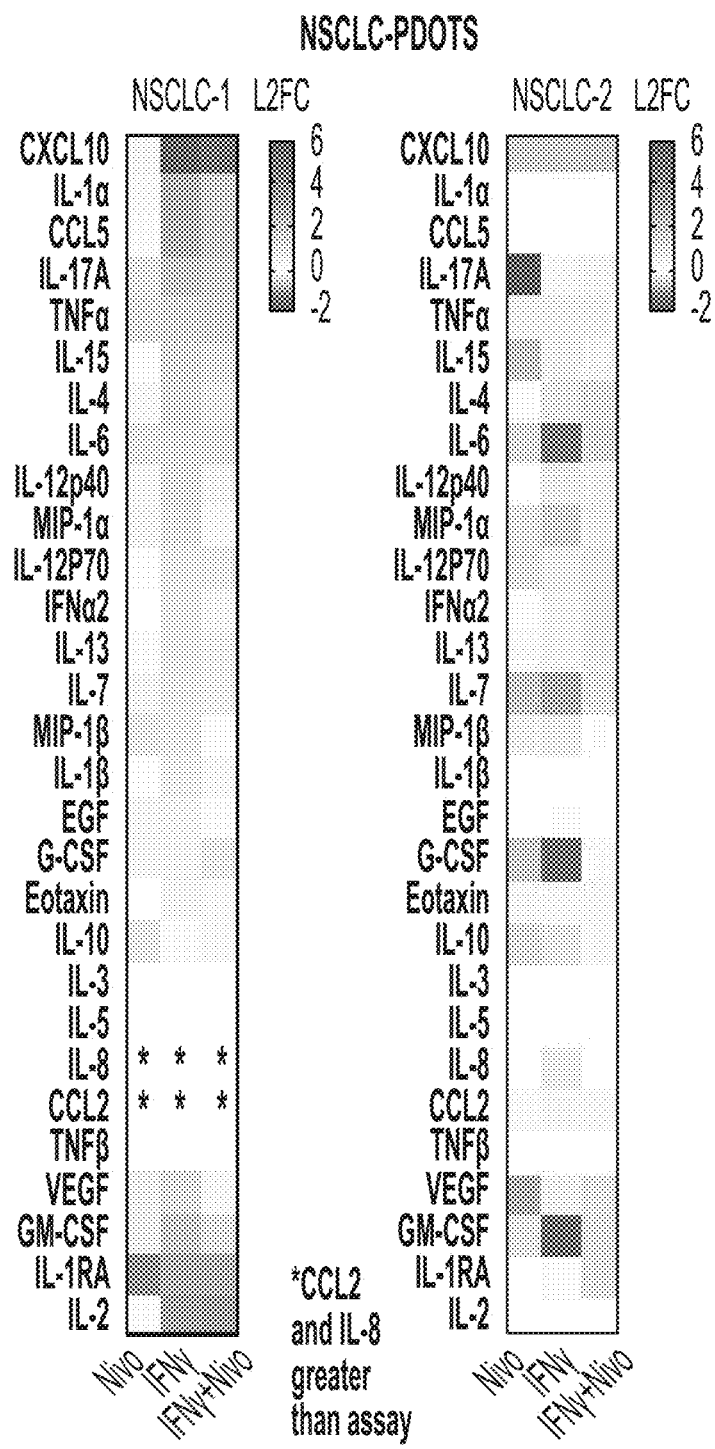
Figure 4G:
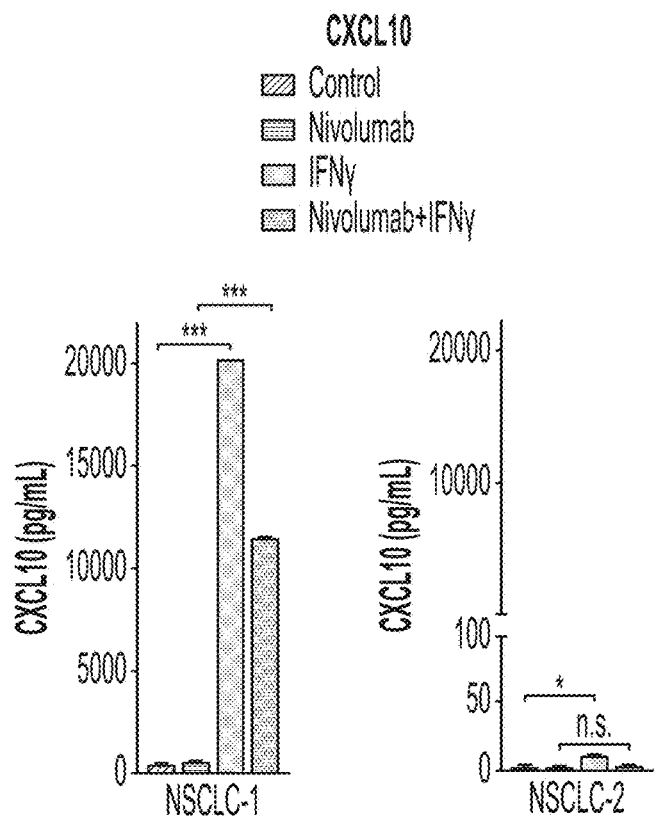
Figure 4H:
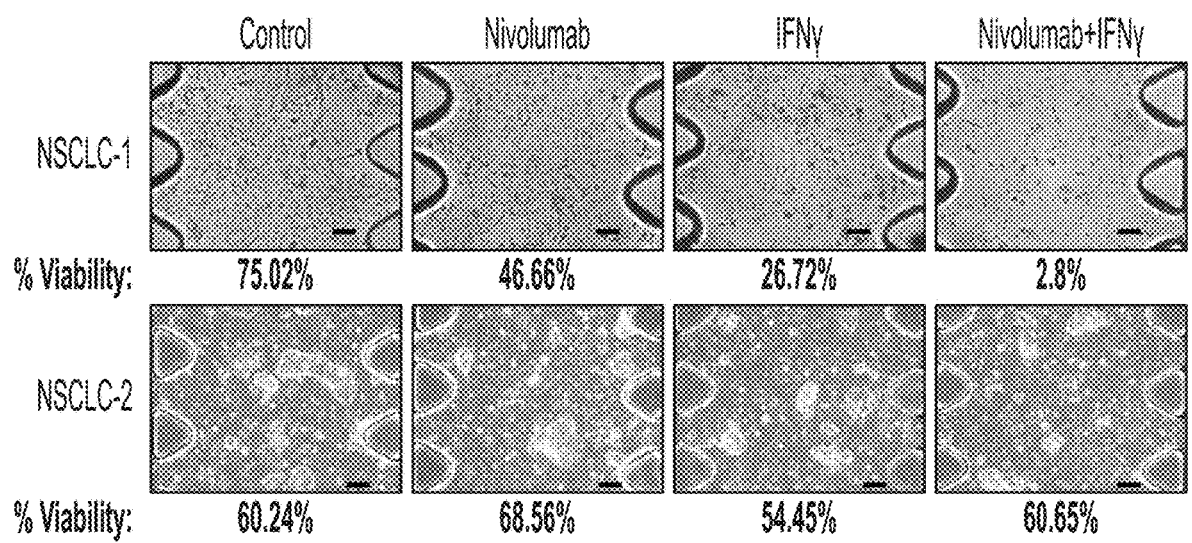
Figure 14B:
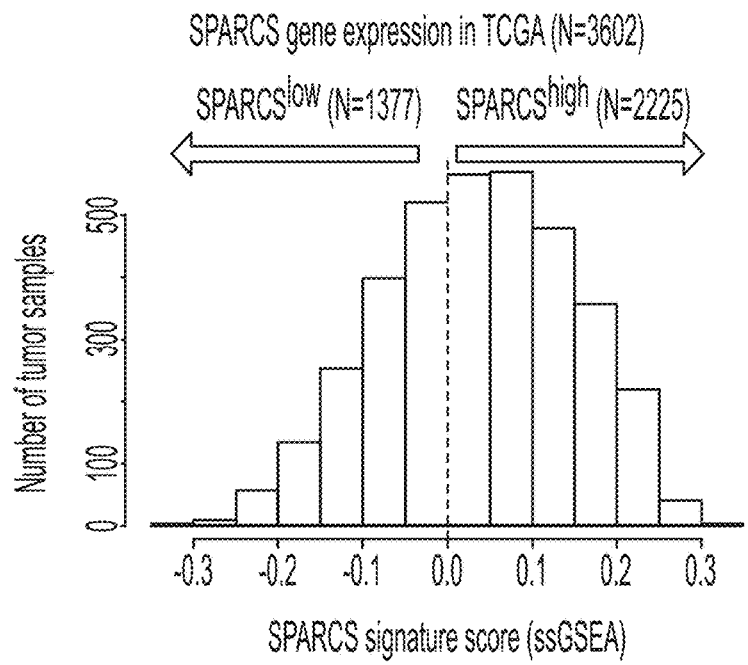
Figure 14C:
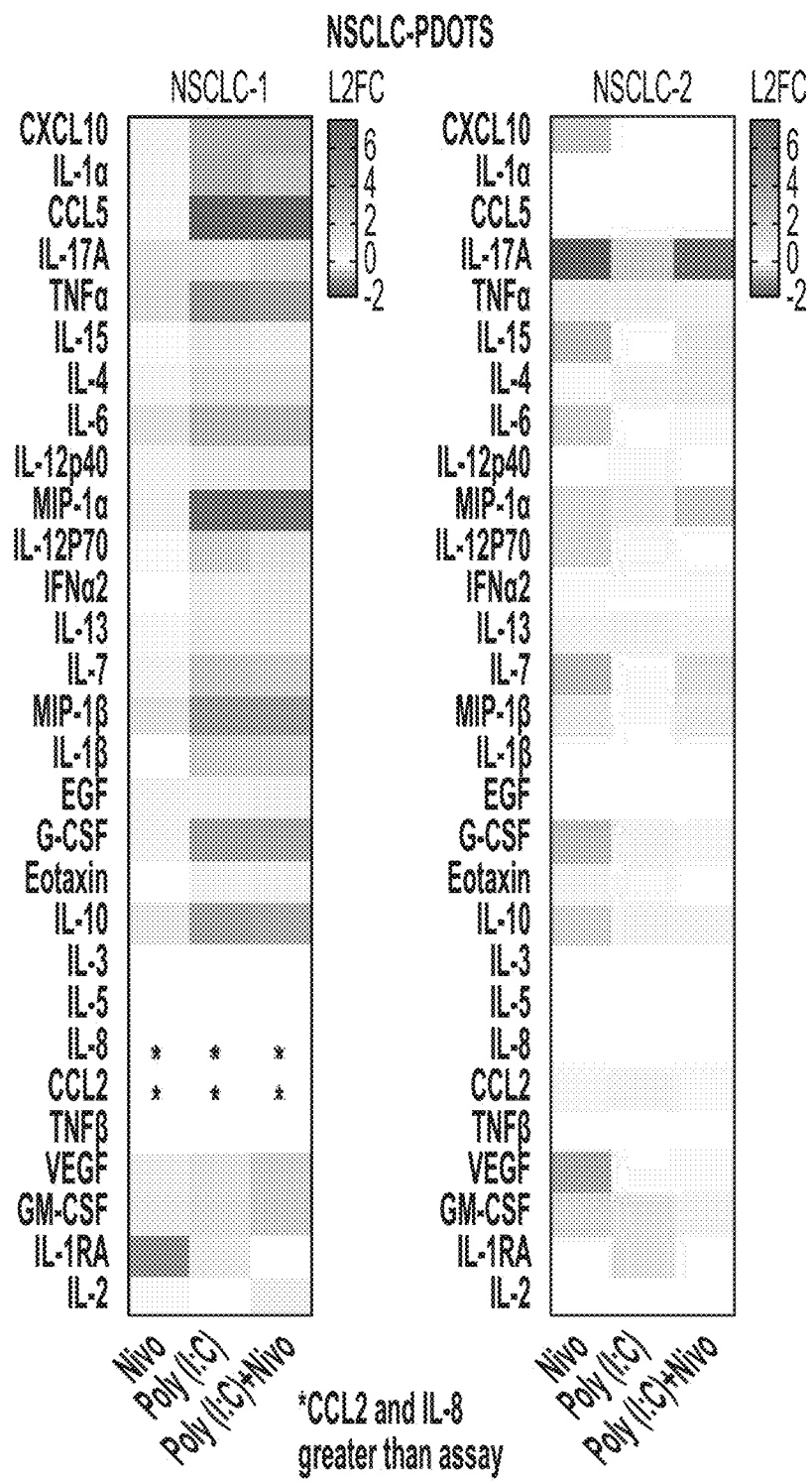
Figure 14D:
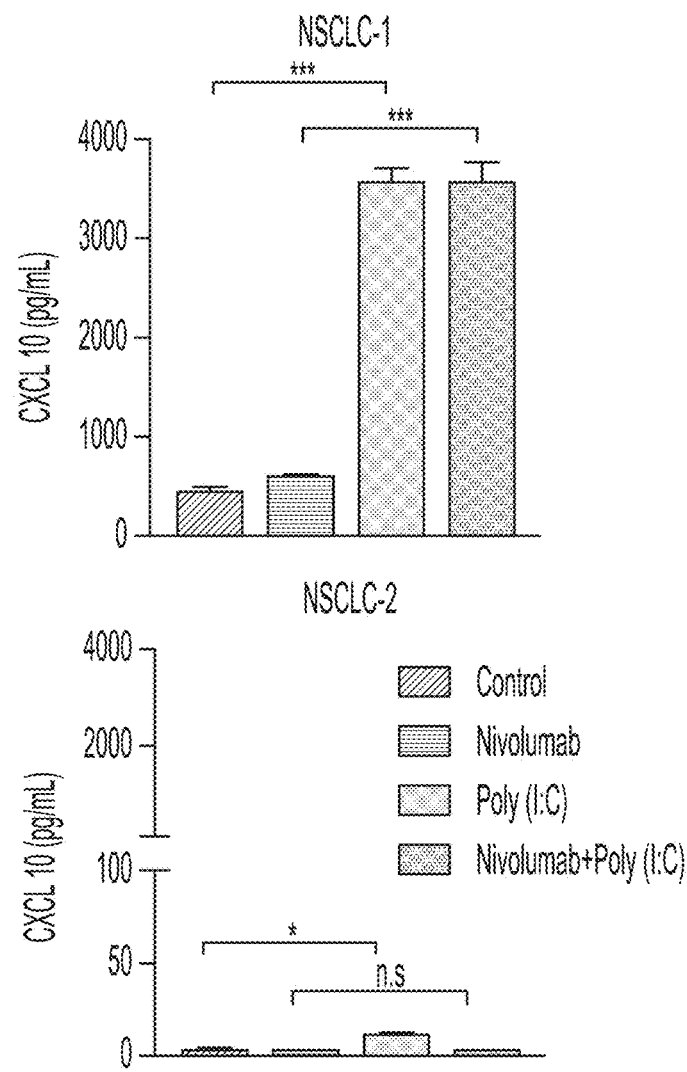
Figure 14E:
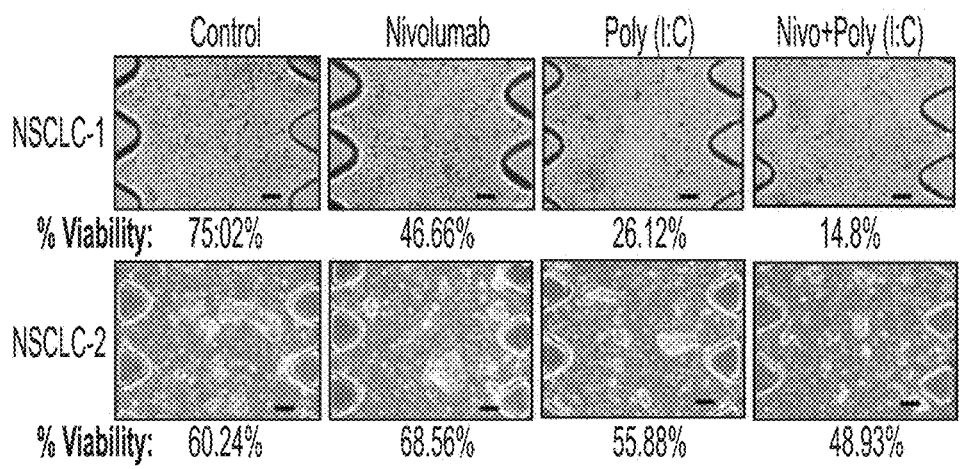

Immune cell GSEA[20] was next used to assess whether certain immune infiltrates might be associated with elevated SPARCS expression in TCGA (FIG. 4A). Despite markers of cytotoxic T cells and an adaptive immune response (AIR), the top associated signatures were innate immune response (IIR) and myeloid derived suppressor cells (MDSC), followed by neutrophils and macrophages (FIG. 4A). Grouping of TCGA tumors into discrete SPARCS high and low categories (FIG. 14B), confirmed robust and significant association of SPARCS$^{high}$ tumors with IIR (q value=9.68E-275), MDSC (q value=7.73E-257), AIR (q value=1.41E-201), neutrophils (q value=2.41E-131) and macrophages (q value=4.60E-126) (FIGS. 4B and 4C). Consistent with T cell and myeloid cell chemotaxis, CXCL10 and CCL2 gene expression in primary tumors was tightly associated with the SPARCS$^{high}$ state (FIG. 4D). Thus, myeloid cell infiltration may further contribute to an immunosuppressed microenvironment in SPARCS$^{high}$ tumors.

Finally, ex vivo culture of patient-derived organotypic tumor spheroids (PDOTS) was utilized, which retain autologous tumor infiltrating lymphocytes[21], to determine the potential translational relevance of these findings. Using multiplexed immunofluorescence, T cell infiltration of two different KRAS mutant non-small lung cancer specimens was confirmed (FIG. 4E), one of which had SPARCS$^{high}$ features including SETD2 inactivation and an APOBEC mutation pattern (NSCLC-1), in contrast to the other which exhibited STK11/RTP53 co-mutation (NSCLC-2) and T cell localization between tumor nests. IFNγ or Poly (I:C) treatment of NSCLC-1 PDOTS markedly enhanced production of multiple cytokines/chemokines, especially CXCL10, and sensitized them to ex vivo PD-1 blockade with nivolumab, in contrast to NSCLC-2 (FIGS. 4F-H and 14C-E). Thus hyperactivated IFN signaling associated with the SPARCS$^{high}$ state can be directly ascertained from patient samples and may promote sensitivity to PD-1 blockade.

Here SPARCS was identified as a novel subclass of ERVs silenced by EZH2 and poised to undergo positive feedback signal amplification due to their antisense localization in 3' UTRs of IFN stimulated genes. Whereas prior reports utilized DNMT inhibition to uncover ERVs more generally[11,12], the data reveal that mesenchymal tumor subclones with high AXL expression and low EZH2 levels trigger SPARCS expression when exposed to IFNγ. This SPARCS$^{high}$ state was also associated with downregulation of multiple SWI/SNF components and RCC, potentially contributing to the immunogenicity recently reported following PBRM1 inactivation[22,23]. While SPARCS expression promotes MHC class 1 upregulation and T cell infiltration, activation of immune checkpoints and myeloid infiltration may promote tumor immune suppression, similar to a chronic virally infected state. Therapeutically, this may have important implications for drug combinations with PD-1 blockade. For example, in contrast to potential antagonism by JAK1/2 inhibitors, therapies that activate JAK signaling such as PTPN2 inhibition[24], inhibit certain chromatin regulators[22,23,25], or target TBK[21,24], could alter SPARCS physiology to favor response.

Methods

Patients Samples

SCLC and NSCLC human tumor samples were collected and analyzed according to Dana-Farber/Harvard Cancer Center IRB-approved protocols. These studies were conducted according to the Declaration of Helsinki and approved by Dana-Farber and Brigham and Women's Hospital IRBs.

Cell Lines

The human SCLC cell lines H69, H69M, H69AR, H841, SHP77, H187, H345 and 11524 were obtained from the laboratory of Dr. Joan Albanell and were authenticated following Short Tandem Repeat (STR) genotyping. Clear cell renal carcinoma (ccRCC) cell lines A704, A498, 786-O, 769-P and Caki-2 were obtained from the laboratory of Dr. William G. Kaelin Jr. and were authenticated following STR genotyping. HCC44 cell line was obtained from Broad Institute and was authenticated following STR genotyping. Jr. Jurkat T cells, THP-1 monocytes, H196, MDA-MB-231, HCC1143, MDA-MB-468, H522, T47D, MDA-MB-453, H1436 and H2081 were obtained from the American Type Culture Collection (ATCC) (Rockville, MD) and used for all experiments before reaching 10 passages.

H69, H69M, H69AR, H841, SHP77, H187, H345, H524, H196, HCC44, MDA-MB-231, MDA-MB-453, MDA-MB-468, T47D, HCC1143, H522, H1436, H2081, THP-1, Jurkat and 769-P were cultured in RPMI-1640 (Thermo Fisher Scientific, #11875-119) containing 10% FBS (Gemini Bio-products, #100-106) and 1× pen-strep (Gemini Bio-products, #400-109). 786-O and A498 were maintained in Dulbecco's Modified Eagles Medium (DMEM) (Thermo Fisher Scientific, #11965-118) containing 10% FBS and 1× pen-strep. Caki-2 cells were maintained in McCoy's 5A medium (Life Technologies #16600108) supplemented with 10% FBS and 1× Penicillin-Streptomycin. A704 cell lines was maintained in Eagle's Minimum Essential Medium (EMEM) (Sigma, #M4780) supplemented with 2 mM Glutamine (Life Technologies, #25030081), 1% Non-Essential Amino Acids (NEAA) (Life Technologies, #11140-050), 1 mM Sodium pyruvate (Life Technologies, #11360-070), 15% FBS and 1× Penicillin-Streptomycin.

Compounds and Treatments

Recombinant human IFN-γ (#285-IF) IFN-α (#11100-1) and IFN-β (#8499-IF) proteins were purchased from R&D Systems (Minneapolis, MN) and reconstituted in sterile, deionized water. MRT67307 and Ruxolitinib were synthesized and purchased from Shanghai Haoyuan Chemexpress Co. Both drugs were reconstituted at 10 mM in DMSO and stored at −20° C. GSK126 (#S7061) was purchased from Selleck chemicals (Houston, TX) and reconstituted at 5 mM in DMSO and stored at −20° C.

For IFN pulse experiments, cells were pulsed 10 minutes with IFN-γ 200 ng/mL or 10 ng/mL), IFN-α 10 000 U/mL), or IFN-β 10 000 U/mL), extensively washed, and chased in fresh media for an additional 24, 48 or 72 hours. To test drug effects on gene expression or protein secretion, IFN-γ pulsed H69AR cells were treated with DMSO, 1 µM MRT67307 or 100 nM Ruxolitinib for 24, 48 and 72 hours.

For EZH2 inhibition experiments, H69 cells were treated with 5 µM GSK126 for 6 days. Drug was replenished every 3 days with both suspension and adherent cells carried each time. After the GSK126 treatment period, equal numbers of DMSO-treated and GSK126-treated cells were exposed to either H₂O or 200 ng/mL IFN-γ for 24 hours before harvesting of RNA or conditioned media (CM).

SCLC GEM Model

All mouse experiments were conducted in accord with a Dana-Farber Cancer Institute Institutional Animal Care and Use Committee (IACUC) approved protocol. Primary tumor and metastasis tissue sections used in this study were from the genetically engineered mouse (GEM) model of SCLC consisting of the $Rb^{L/L}/p53^{L/L}$ allelic genotype[26]. A total number of 24 slices of 1 mm thickness were collected providing a sufficient number to cover the lung volume. Tumor volume per animal was quantified using 3D Slicer by manual quantification of at least 8 consecutive axial image sequences. MRI was performed to follow tumor volume and weights were monitored bi-weekly. Mice were euthanized and lungs and livers were perfused with 10% formalin, stored in fixative overnight, and embedded in paraffin. For further staining with hematoxylin and eosin (H % E) and antibodies, sections of 5 µm were cut.

Xenograft Studies

H69AR xenograft model was established by subcutaneous (s.c.) injection of $2.5 \times 10^5$ sgCTRL or sgMAVS-H69AR cells in matrigel (Corning, Corning, NY) into the flank of nude mice (Charles River Laboratories, Wilmington, MA). Tumor volume was determined from caliper measurements of tumor length (L) and width (W) according to the formula $L \times W^2/2$. Both tumor size and body weight were measured three times per week.

Immunoblotting, Antibodies and ELISA

Protein was isolated from cell lines and measured by BCA (Pierce Biotechnology). Protein extracts were subjected to polyacrylamide gel electrophoresis using the 4%-12% NuPAGE gel system (Invitrogen, Carlsbad, CA), transferred to PVDF (Millipore) membranes, and immunoblotted using antibodies that specifically recognize TBK1 (#3013), S172 pTBK1 (#5483), pERK1/2 (#4370), ERK1/2 (#9107), S473 pAKT (#4060), AKT (#9272), S396 pIRF3 (#4947), IRF3 (#4302), Y701 pSTAT1 (#9171), STAT1 (#9172), AXL (#8661), EZH2 (#5246), STING (#13647), MAVS (#3993), E-Cadherin (#3195), Vimentin (#5741), β-Actin (#4970), Tubulin (#2144) (Cell Signaling Technologies, Danvers, MA) and IKKε (#14907) (Sigma-Aldrich, St. Louis, MO).

Secondary antibodies were from LICOR Biosciences (Lincoln, NE): IRDye 800CW Goat anti-Mouse IgG (H+L) (#926-32210), IRDye 800CW Goat anti-Rabbit IgG (H+L) (#926-32211). LICOR blocking buffer (#927-40000) was used to dilute primary and secondary antibodies, with the exception of phosho-specific antibodies, which were diluted in HIKARI Signal Enhancer Solutions 1 and Solution 2 (Nacalai USA, Inc. #NU00101). Imaging of blots and quantitation of bands was performed using the LICOR Odyssey system.

Proteome Profiler™ Human Cytokine Array Kit (#ARY005B) and CXCL10 ELISA (#DIP100) (R&D Systems, Minneapolis, MN), were performed according to manufacturer's instructions. For cytokine array, conditioned media (CM) from SCLC cells at basal conditions was collected after 48 and 72 hours. For CXCL10 ELISA, CM from IFN-γ pulsed cells was collected after 72 hours.

Microfluidic Devices Design and Fabrication

Microfluidic device design and fabrication was performed as described[27], with modifications of device dimensions to accommodate larger volumes of media. DAX-1 3D cell culture chip (AIM Biotech, Singapore) was also used for select studies.

Microfluidic Culture

H69, H69M and H69AR cell suspensions (2.5×10 4 cells) were pelleted and resuspended in type I rat tail collagen (Corning, Corning, NY) at a concentration of 2.5 mg/mL following addition of 10×PBS with phenol red with pH adjusted using NaOH. pH 7.0-7.5 confirmed using PANPEHA Whatman paper (Sigma-Aldrich, St. Louis, MO). The cell-collagen mixture was then injected into the center gel region of the 3D microfluidic culture device. Microfluidic culture devices were designed with a central region containing the cell-collagen mixture, surrounded by 2 media channels located on either side formed by bonding a coverslip to a patterned polydimethylsiloxane (PDMS) substrate. Collagen hydrogels containing cells were incubated 30 minutes at 37° C. and then hydrated with media with or without 2.5×10$^4$ cells CFSE labeled Jurkat T cells and THP1 monocytes in the side media channels. Jurkat T cells or THP1 monocytes were labeled with the CFSE Cell Division Tracker Kit (BioLegend, San Diego, CA) following manufacturer's instructions. Following 48 hours of incubation, images were captured on a Nikon Eclipse 80i fluorescence microscope equipped with Z-stack (Prior) and CoolSNAP CCD camera (Roper Scientific). Image capture and analysis was performed using NIS-Elements AR software package. Whole device images were achieved by stitching in multiple captures. Cell quantitation was performed by measuring total cell area of CFSE dye.

Ex Vivo Culture of Patient-Derived Organotypic Tumor Spheroids (PDOTS)

PDOTS from human NSCLC resection specimens were generating according to the recent publication[21]. Briefly, fresh tumor specimens were minced and resuspended in media with collagenase type IV (Life Technologies, Carlsbad, CA). After digestion, samples were strained over 100 μm filter and 40 μm filters to generate S1 (>100 μm), S2 (40-100 μm), and S3 (<40 μm) spheroid fractions. S2 spheroid fraction was pelleted and resuspended in type I rat tail collagen (Corning, Corning, NY) at a concentration of 2.5 mg/mL. The spheroid-collagen mixture was then injected into the center gel region of the 3D microfluidic culture device. Collagen hydrogels containing PDOTS were hydrated with media and treated with anti-PD-1 (Nivolumab, 100 μg/mL), IFNγ (200 ng/mL), Poly (I:C) (0.5 μg/mL) or combination (Nivolumab+IFNγ Nivolumab+Poly (I:C)). The number of Live/Dead cells in each treatment condition was determined by Trypan Blue Exclusion method and plotted as percentage of viability.

Flow Cytometry Analysis and Cell Sorting

Cells were stained with anti-PD-L1 (Biolegend, Cat #329717), anti-CD44 (Biolegend, Cat #103011) or isotype IgG control antibodies (Biolegend, Cat #400326 and Cat #400611), in PBS containing 2% FBS for analysis and cell sorting. Briefly, cells were washed and further incubated with the indicated antibodies at 2 μg/mL. After 3 washes with PBS, cells were resuspended in PBS containing 2% FBS and analyzed on BD FACSCanto II or sorted to >95% purity using a BD FACSAria II. Levels were compared with isotype control antibodies. PD-L1 and CD44 mean fluorescence intensity (MFI) was normalized to isotype control. The data analyses were performed with FlowJo software (TreeStar).

Cytokine Profiling

Multiplex assays were performed utilizing the bead-based immunoassay approach Bio-Plex Pro™ Human Cytokine 40-plex Assay (Cat #171AK99MR2) on a Bio-plex 200 system (Cat #171000201) (Bio-Rad Laboratories, Hercules, CA) and the Human Cytokine/Chemokine Maganetic Bead Panel (Cat #HCYTMAG-60K-PX30) on a Luminex MAG-PIX system (Merck Millipore, Billerica, MA). Conditioned media concentration levels [pg/ml] of each protein were derived from 5-parameter curve fitting models. Fold changes relative to the corresponding control were calculated and plotted as log 2FC. Lower and upper limits of quantitation (LLOQ/ULOQ) were imputed from standard curves for cytokines above or below detection.

Quantitative RT-PCR

Total cellular RNA was extracted using the miRNeasy Mini Kit (Qiagen, Hilden, Germany) according to manufacturer's instructions. After extraction, 1 μg total RNA was used to generate cDNA with the SuperScript III First-Strand Synthesis SuperMix for qRT-PCR kit (Thermo Fisher Scientific, Waltham, MA). Quantitative reverse transcription PCR (qRT-PCR) of the indicated genes was performed using SYBR green PCR Master Mix (Applied Biosystems, Foster City, CA) and the Applied Biosystems 7300 Fast real-time PCR system and software. The relative expression was normalized with the expression of the housekeeping gene 36B4. The sequences of primers used have been listed in Table 3.

TABLE 3

Gene primer sequences

| Gene name | Forward (5'-3') | Reverse (5'-3') |
|---|---|---|
| 36B4 | CAGATTGGCTACCCAACTGTT (SEQ ID NO: 2) | GGAAGGTGTAATCCGTCTCCAC (SEQ ID NO: 14) |
| PD-L1 | TATGGTGGTGCCGACTACAA (SEQ ID NO: 3) | TGCTTGTCCAGATGACTTCG (SEQ ID NO: 15) |
| TRIM22 | CCCTGCAGAGGCTGATAAAG (SEQ ID NO: 4) | GCCAGGTTATCCAGCACATT (SEQ ID NO: 16) |
| IFNG | TCGGTAACTGACTTGAATGTCCA (SEQ ID NO: 5) | TCGCTTCCCTGTTTTAGCTGC (SEQ ID NO: 17) |
| IFNB | ATGACCAACAAGTGTCTCCTCC (SEQ ID NO: 6) | GGAATCCAAGCAAGTTGTAGCTC (SEQ ID NO: 18) |
| IFNA2 | GCTTGGGATGAGACCCTCCTA (SEQ ID NO: 7) | CCCACCCCTGTATCACAC (SEQ ID NO: 19) |
| CXCL10 | GTGGCATTCAAGGAGTACCTC (SEQ ID NO: 8) | TGATGGCCTTCGATTCTGGATT (SEQ ID NO: 20) |
| IKKE | ATTACAACACTGCCAAGGGCGTGT (SEQ ID NO: 9) | GGAGCACCTCCATGACCCAGTGCA (SEQ ID NO: 21) |

TABLE 3-continued

Gene primer sequences

| Gene name | Forward (5'-3') | Reverse (5'-3') |
| --- | --- | --- |
| E-Cadherin | CGAGAGCTACACGTTCACGG (SEQ ID NO: 10) | GGGTGTCGAGGGAAAAATAGG (SEQ ID NO: 22) |
| Vimentin | GACGCCATCAACACCGAGTT (SEQ ID NO: 11) | CTTTGTCGTTGGTTAGCTGGT (SEQ ID NO: 23) |
| CD44 | CTGCCGCTTTGCAGGTGTA (SEQ ID NO: 12) | CATTGTGGGCAAGGTGCTATT (SEQ ID NO: 24) |
| CCL2 | CCCCAGTCACCTGCTGTTAT (SEQ ID NO: 13) | TGGAATCCTGAACCCACTTC (SEQ ID NO: 25) |

TABLE 4

ERV Primer Sequences

| ERV name | Forward (5'-3') | Reverse (5'-3') |
| --- | --- | --- |
| ERVMER34-1 | GAATTCAGTGCCACTAAGCAGAC (SEQ ID NO: 26) | TCGGTATATCCAAGCATGATCC (SEQ ID NO: 58) |
| MER21C | GGAGCTTCCTGATTGGCAGA (SEQ ID NO: 27) | ATGTAGGGTGGCAAGCACTG (SEQ ID NO: 59) |
| LTR12F | GCAGGGAGGATTGAAAGAAA (SEQ ID NO: 28) | TGGTGCTGACTTCAAGAACG (SEQ ID NO: 60) |
| MER66C | AGGAAGCAGCAAATGGCTAA (SEQ ID NO: 29) | CAAATTAAGGAGCGGGTCAA (SEQ ID NO: 61) |
| ERV316A3 | AGCAGATAGCCCAGACCTCA (SEQ ID NO: 30) | CAAAGCTCTGCCCACTAAGG (SEQ ID NO: 62) |
| ERVFb1 | ATATCCCTCACCACGATCCTAATA (SEQ ID NO: 31) | CCCTCTGTAGTGCAAAGACTGATA (SEQ ID NO: 63) |
| ERV9.1 | TCTTGGAGTCCTCACTCAAACTC (SEQ ID NO: 32) | ACTGCTGCAACTACCCTTAAACA (SEQ ID NO: 64) |
| ERV-F | CAGGAAACTAACTTTCAGCCAGA (SEQ ID NO: 33) | TAAAGAGGGCATGGAGTAATTGA (SEQ ID NO: 65) |
| ERVL | ATATCCTGCCTGGATGGGGT (SEQ ID NO: 34) | GAGCTTCTTAGTCCTCCTGTGT (SEQ ID NO: 66) |
| MLT1B | TGCCTGTCTCCAAACACAGT (SEQ ID NO: 35) | TACGGGCTGAGCTTGAGTTG (SEQ ID NO: 67) |
| MLT1C49 | TATTGCCGTACTGTGGGCTG (SEQ ID NO: 36) | TGGAACAGAGCCCTTCCTTG (SEQ ID NO: 68) |
| MLT1C627 | TGTGTCCTCCCCCTTCTCTT (SEQ ID NO: 37) | GCCTGTGGATGTGCCCTTAT (SEQ ID NO: 69) |
| MER4D | CCCTAAAGAGGCAGGACACC (SEQ ID NO:38) | TCAAGCAATCGTCAACCAGA (SEQ ID NO: 70) |
| MER57B1 | CCTCCTGAGCCAGAGTAGGT (SEQ ID NO: 39) | ACCAGTCTGGCTGTTTCTGT (SEQ ID NO: 71) |
| MTL2B4 | GGAGAAGCTGATGGTGCAGA (SEQ ID NO: 40) | ACCAACCTTCCCAAGCAAGA (SEQ ID NO: 72) |
| MLTA10 | TCTCACAATCCTGGAGGCTG (SEQ ID NO: 41) | GACCAAGAAGCAAGCCCTCA (SEQ ID NO: 73) |
| THE1D | CACCCTGCTTCTCCTGCT (SEQ ID NO: 42) | AATGCCTGAGACTGGGTGAT (SEQ ID NO: 74) |
| TRIM38/MLT1A | TGGGCTCTTTGGGTGATAGT (SEQ ID NO: 43) | TTGCAGATGGCTACCTTCCT (SEQ ID NO: 75) |

TABLE 4-continued

ERV Primer Sequences

| ERV name | Forward (5'-3') | Reverse (5'-3') |
|---|---|---|
| TRIM38/MLT1J | GCTGTTGCACACATGCTCTT (SEQ ID NO: 44) | GATGTGGAAGTCTGGGAAGC (SEQ ID NO: 76) |
| SPATS2L/MLT1K | CAGATGAAGCCCTCTCTCAGA (SEQ ID NO: 45) | CCTTCCTCTCTCCTGGTGTC (SEQ ID NO: 77) |
| BEND6/PABL_B | GAAGGCACATAACCCCAACC (SEQ ID NO: 46) | GGGTCCAGCTGTGTTTTCTG (SEQ ID NO: 78) |
| AIG1/MLT1A0 | ATGAATGGGATTGGTGGGCT (SEQ ID NO: 47) | TTCTAGAGCCTGGGAAGTCC (SEQ ID NO: 79) |
| MSRB2/MSTA | TAACTGGGTCATGAGGGTGG (SEQ ID NO: 48) | CATTTGCTCGGATTCTGGGG (SEQ ID NO: 80) |
| ANTXR1/LTR79 | AACTCTGGGCTTCCGTTTCC (SEQ ID NO: 49) | AAAGCATGCCTCTTTCCTGC (SEQ ID NO: 81) |
| ADAM19/MER92B | GTTAAGCTTCCCTCCTCCCC (SEQ ID NO: 50) | AGTGAAAAGGCTCAGACCGA (SEQ ID NO: 82) |
| F3/MLT1I | TTCCCTCTGCCCTGATCTAA (SEQ ID NO: 51) | GTCAGTGGCTTACAACAACGT (SEQ ID NO: 83) |
| IFI44L/LTR26 | CTCCAAGGAATTGACTCAGCA (SEQ ID NO: 52) | TCTACCTCCCTGCTGAGTCT (SEQ ID NO: 84) |
| IL32/THE1D | CACCCTGCTTCTCCTGCT (SEQ ID NO: 53) | AATGCCTGAGACTGGGTGAT (SEQ ID NO: 85) |
| HERC3/MSTB | ACCTCCTCTCCACTCTTCCT (SEQ ID NO: 54) | AGTTCTGCAGGCTCTACAGG (SEQ ID NO: 86) |
| TNFRSF9/MLT1I | AGCTGTTACAACATAGTAGCCAC (SEQ ID NO: 55) | GGACAGGGACTGCAAATCTGAT (SEQ ID NO: 87) |
| EPHA3/LTR37A | CTGCTCTGTTCTCGACAGCTT (SEQ ID NO: 56) | CAGCTCCCCTTGAATTGTTTTG (SEQ ID NO: 88) |
| SERPINB9/MER50 | AATGCAAGTGGTACTTTTGCCA (SEQ ID NO: 57) | AAGCCCGATGAATGTCTTCCT (SEQ ID NO: 89) | dsRNA Enrichment

For dsRNA enrichment, RNA was first treated or not for 30 minutes with 50 µg/ml RNase A (Qiagen, Hilden, Germany) in high-salt concentration (NaCl, 0.35 M) to prevent dsRNA degradation. After treatment, RNase A was removed by ethanol precipitation and the product was resuspended in sterile water. Next, RNase A-treated RNA was immunoprecipitated (IP) using the J2 dsRNA-specific antibody (English and Scientific Consulting Kft, Szirák, Hungary). In brief, the product of 9 µg of RNase A-treated RNA was incubated in binding buffer (150 mM NaCl, 50 mM TRIS pH8.0, 1 mM EDTA, 1% NP-40) with 5 µg of J2 antibody rotating overnight at 4° C. J2-bound dsRNA was incubated in biding buffer with 25 µL of Dynabeads Protein G (Thermo Fisher Scientific, Waltham, MA) for 4 hours at 4° C., followed by washes in cold binding buffer. RNA was then extracted with TRIzol Reagent and expression levels of indicated genes were analyzed by qRT-PCR.

Enrichment of dsRNA over ssRNA was then calculated by normalizing the delta Ct of ERVs (dsRNA) against beta-actin (ssRNA).

First Strand cDNA Synthesis and Strand Specific PCR for Detection of Sense and Antisense ERV Transcripts Using TASA-TD Methodology Components from the SuperScript III First-Strand Synthesis System for RT-PCR (Thermo Fisher Scientific, Waltham, MA) were adapted to perform reverse transcription with RNA from H69AR previously pulsed with IFNγ 10 minutes. For first strand cDNA synthesis 400 ng RNA was used for β-actin, MLT1C49, MLT1A and MLT1J. 1 µM of a gene specific primer ligated to a TAG-sequence not specific for the human genome (GSP sense/antisense (RT) TAG) was implemented in the reaction. RNA and primers were preheated at 65° C. for 5 min. For the total reaction: the GSP-TAG, 0.5 mM dNTP, 5 mM MgCl2, 10 mM DTT, 40U RNaseOUT, 100U SuperScriptIII® RT and 240 ng Actinomycin D (Sigma-Aldrich, St. Louis, MO) were added with the RNA for a 20 µl reaction. Synthesis was performed at 50° C. for 50 minutes and terminated at 85° C. for 5 mM. RT with extremely low intrinsic RNase H activity (for cleavage of RNA from RNA/DNA duplexes) and Actinomycin D was added to prevent second strand cDNA RT resulting in antisense artifacts[28]. After cDNA synthesis 2U recombinant RNase H was added to each reaction and incubated 20 minutes at 37° C. Finally, the first strand cDNA mix was ethanol precipitated and resuspended in 10 µl sterile water. Afterwards gene and strand specific qRT-PCR was performed using SYBR green PCR Master Mix. To amplify sense cDNA and antisense cDNA a TAG-primer and GSP sense-primer and a TAG-primer and GSP antisense-primer were used, respectively. Sense and antisense specific qRT-PCR was performed using both sense and antisense cDNA of beta-actin as an internal negative control that was previously demonstrated to have no antisense transcript[29]. The sequences of primers used have been listed in Table 5.

TABLE 5

Primers used for TASA-TD method

| Primer | Sequences for first strand cDNA synthesis (GSP sense/antisense TAG) (5'-3') |
|---|---|
| β-actin sense TAG | GCACACGACGACAGACGACGCACCAAACATGATCTGGGT CATCTTCTC (SEQ ID NO: 90) |
| β-actin antisense TAG | GCACACGACGACAGACGACGCACGCTCGTCGTCGACAAC GGCTCCGGCA (SEQ ID NO: 91) |
| MLT1C49 sense TAG | GCACACGACGACAGACGACGCACTGGAACAGAGCCCTTC CTTG (SEQ ID NO: 92) |
| MLT1C49 antisense TAG | GCACACGACGACAGACGACGCACTATTGCCGTACTGTGG GCTG (SEQ ID NO: 93) |
| MLT1J sense TAG | GCACACGACGACAGACGACGCACGATGTGGAAGTCTGGG AAGC (SEQ ID NO: 94) |
| MLT1J antisense TAG | GCACACGACGACAGACGACGCACGCTGTTGCACACATGC TCTT (SEQ ID NO: 95) |
| MLT1A sense TAG | GCACACGACGACAGACGACGCACTTGCAGATGGCTACCT TCCT (SEQ ID NO: 96) |
| MLT1A antisense TAG | GCACACGACGACAGACGACGCACTGGGCTCTTTGGGTGA TAGT (SEQ ID NO: 97) |

| Primer | Sequences for gene and strand specific qRT-PCR (5'-3') |
|---|---|
| β-actin sense | GCTCGTCGTCGACAACGGCTCCGGCA (SEQ ID NO: 98) |
| β-actin antisense | CAAACATGATCTGGGTCATCTTCTC (SEQ ID NO: 99) |
| MLT1C49 sense | TATTGCCGTACTGTGGGCTG (SEQ ID NO: 100) |
| MLT1C49 antisense | TGGAACAGAGCCCTTCCTTG (SEQ ID NO: 101) |
| MLT1J sense | GCTGTTGCACACATGCTCTT (SEQ ID NO: 102) |
| MLT1J antisense | GATGTGGAAGTCTGGGAAGC (SEQ ID NO: 103) |
| MLT1A sense | TGGGCTCTTTGGGTGATAGT (SEQ ID NO: 104) |
| MLT1A antisense | TTGCAGATGGCTACCTTCCT (SEQ ID NO: 105) |
| TAG sequence | GCACACGACGACAGACGACGCAC (SEQ ID NO: 106) |

CRISPR-Cas9 Gene Editing and Lentiviral Infection

Oligonucleotides coding for guide RNAs that target STING and MAVS genes were chosen from the Avana library and the Brunello library[30]. A non-targeting sgRNA from the Gecko library v2 was used as a dummy sgRNA for control[31]. Lenti CRISPRv2 vectors were cloned as previously described[31,32]. sgRNA target sequences are described on Table 6.

HEK-293T cells were transduced with lentiCRISPRv2 using X-treme Gene 9 (Roche, Basel, Switzerland) according to the manufacturer's instructions. On day 2, target cells were seeded, and allowed to adhere overnight. On day 3 the supernatant of transduced HEK293T cells was collected and added to the target cells through a 0.45 μm filter. Supernatant from transduced HEK293T cells was again collected and added to target cells on day 4. On day 5, puromycin or blasticidin was added to select infected cells (for four days).

TABLE 6

CRISPR-Cas9 sgRNAs target sequences

| Target Gene | sgRNA Target Sequence |
|---|---|
| MAVS | AGTACTTCATTGCGGCACTG (SEQ ID NO: 107) |
| STING | GGTACCGGGGCAGCTACTGG (SEQ ID NO: 108) |
| sgCTRL | ATCGTTTCGCTTAACGGCG (SEQ ID NO: 109) |

Poly(I:C) Treatment

For Poly(I:C) dsRNA treatment experiments, H69ARsgCTRL and H69ARsgMAVS cells were plated in RPMI media, transfected with 0.5 μg/mL Poly(I:C) HMW (InvivoGen, Sand Diego, CA) using XtremeGene HP transfection reagent (Sigma-Aldrich, St. Louis, MO) and cultured for 72 hours. On day 3 after transfection, conditioned media was recovered and CXCL10 protein expression was quantified using Human CXCL10/IP-10 Quantikine ELISA kit (R&D Systems, Minneapolis, MN). RNA was extracted and expression levels of relevant genes were analyzed by qRT-PCR.

Immunohistochemical Staining

After deparaffinizing tissue blocks, antigen retrieval was achieved by wet autoclave (121 degrees Celsius, 15 min) in Antigen Retrieval Solution, pH 9 (Dako, S2367) for p-TBK1. In order to block endogenous peroxide enzyme, tissue sections were incubated for 30 minutes using Peroxidase-Blocking Solution (Dako, S2023). Then, to block non-specific background staining, tissue sections were incubated for 20 minutes with Protein Block (Dako, X0909) (human tissue) or Mouse on Mouse blocking reagent (Vector Laboratories, MKB-2213) (mouse tissue). Primary antibody specific for pTBK1 (Cell Signaling Technology, 5483; 1:50 dilution) was applied, and slides were incubated for 16 hours at 4° C. Visualization was achieved using EnVision™+/HRP, Rabbit (Dako, K4003) for pTBK1, followed by diaminobenzidine (Dako, K3468), and hematoxylin counterstain. Expression levels of pTBK1 were evaluated by two pathologists who were blinded to other data.

Multiplexed Immunofluorescence

Multiplex Immunofluorescent staining was performed overnight for approximately 12 hours on BOND RX fully automated stainers (Leica Biosystems) as previously described[33]. Briefly, tissue sections of 5-μm thick FFPE were baked for 3 hours at 60° C. before loading into the BOND RX. Slides were deparaffinized (BOND DeWax Solution, Leica Biosystems) and rehydrated with series of graded ethanol to deionized water. Antigen retrieval was performed in BOND Epitope Retrieval Solution 1 (ER1, Leica Biosystems) at pH 6 for 10 minutes at 98° C. Deparaffinization, rehydration and antigen retrieval were all pre-programmed and executed by the BOND RX. Next, slides were serially stained with primary antibodies, such as anti-CD8 (clone C8/144B; DAKO, dilution 1:5000). Incubation time per primary antibody was 40 minutes. Subsequently, anti-rabbit Polymeric Horseradish Peroxidase (Poly-HRP, BOND Polymer Refine Detection Kit, Leica Biosystems) was applied as a secondary label with an incubation time of 10 minutes. Signal for antibody complexes was labeled and visualized by their corresponding Opal Fluorophore Reagents (PerkinElmer) by incubating the slides for 5 minutes. The same process was repeated for the following antibodies/fluorescent dyes. Slides were air dried, mounted with Prolong Diamond Anti-fade mounting medium (#P36965, Life Technologies) and stored in a light-proof box at 4° C. prior to imaging. The target antigens, antibody clones, and dilutions for markers included in this report and details of controls are listed in Table 7.

TABLE 7

Antibodies used for multiplexed immunofluorescence assay.

| Primary Antibody | Clone ID/Company | Dilution | Opal Kit Fluor | Opal Fluor Dilution |
|---|---|---|---|---|
| Anti-CD8 | C8/144B, DAKO | 1:5000 | Opal 520 | 1:100 |
| Anti-CD4 | 4B12, DAKO | 1:250 | Opal 540 | 1:200 |
| Cytokeratin | AE1/AE3/DAKO | 1:2000 | Opal 690 | 1:50 |

Table summarizing target antigens, antibody clones, dilutions and detail of controls used for multiplexed immunofluorescence staining of NSCLC human specimens used to generate PDOTS.

Image Acquisition and Analysis

Image acquisition was performed using the Mantra multispectral imaging platform (Vectra 3, PerkinElmer, Hopkinton, MA) as previously described[33]. Areas with non-tumor or residual normal tissue (i.e. residual lymph node) were excluded from the analysis. Representative regions of interest were chosen by the pathologist, and 5-7 fields of view (FOVs) were acquired at 20× resolution as multispectral images. Image Analysis was performed using the Inform 2.3 Image Analysis Software (PerkinElmer, Hopkinton, MA).

OncoPanel Assay

Somatic mutations, copy number variations and structural variants in parental H69 cells and H69M-PD-L$^{low}$/H69M-PD-L1$^{high}$ subclones were evaluated by performing the OncoPanel assay from the Center for Advanced Molecular Diagnostics from Brighman and Women's Hospital.

This OncoPanel assay surveys exonic DNA sequences of 300 cancer genes and 113 introns across 35 genes for rearrangement detection. DNA was isolated from cell lines and analyzed by massively parallel sequencing using a solution-phase Agilent SureSelect hybrid capture kit and an Illumina HiSeq 2500 sequencer.

The 300 genes are: ABL1, AKT1, AKT2, AKT3, ALK, ALOX12B, APC, AR, ARAF, ARID1A, ARID1B, ARID2, ASXL1, ATM, ATRX, AURKA, AURKB, AXL, B2M, BAP1, BCL2, BCL2L1, BCL2L12, BCL6, BCOR, BCORL1, BLM, BMPR1A, BRAF, BRCA1, BRCA2, BRD4, BRIP1, BUB1B, CADM2, CARD11, CBL, CBLB, CCND1, CCND2, CCND3, CCNE1, CD274, CD58, CD79B, CDC73, CDH1, CDK1, CDK2, CDK4, CDK5, CDK6, CDK9, CDKN1A, CDKN1B, CDKN1C, CDKN2A, CDKN2B, CDKN2C, CEBPA, CHEK2, CIITA, CREBBP, CRKL, CRLF2, CRTC1, CRTC2, CSF1R, CSF3R, CTNNB1, CUX1, CYLD, DDB2, DDR2, DEPDC5, DICER1, DIS3, DMD, DNMT3A, EED, EGFR, EP300, EPHA3, EPHA5, EPHA7, ERBB2, ERBB3, ERBB4, ERCC2, ERCC3, ERCC4, ERCC5, ESR1, ETV1, ETV4, ETV5, ETV6, EWSR1, EXT1, EXT2, EZH2, FAM46C, FANCA, FANCC, FANCD2, FANCE, FANCF, FANCG, FAS, FBXW7, FGFR1, FGFR2, FGFR3, FGFR4, FH, FKBP9, FLCN, FLT1, FLT3, FLT4, FUS, GATA3, GATA4, GATA6, GLI1, GLI2, GLI3, GNA11, GNAQ, GNAS, GNB2L1, GPC3, GSTM5, H3F3A, HNF1A, HRAS, ID3, IDH1, IDH2, IGF1R, IKZF1, IKZF3, INSIG1, JAK2, JAK3, KCNIP1, KDM5C, KDM6A, DM6B, KDR, KEAP1, KIT, KRAS, LINC00894, LMO1, LMO2, LMO3, MAP2K1, MAP2K4, MAP3K1, MAPK1, MCL1, MDM2, MDM4, MECOM, MEF2B, MEN1, MET, MITF, MLH1, MLL (KMT2A), MLL2(KTM2D), MPL, MSH2, SH6, MTOR, MUTYH, MYB, MYBL1, MYC, MYCL1(MYCL), MYCN, MYD88, NBN, NEGR1, NF1, NF2, NFE2L2, NFKBIA, NFKBIZ, NIOC2-1, NOTCH1, NOTCH2, NPM1, NPRL2, NPRL3, NRAS, NTRK1, NTRK2, NTRK3, PALB2, PARK2, PAX5, PBRM1, PDCD1LG2, PDGFRA, PDGFRB, PHF6, PHOX2B, PIK3C2B, PIK3CA, PIK3R1, PIM1, PMS1, PMS2, PNRC1, PRAME, PRDM1, PRF1, PRKAR1A, PRKCI, PRKCZ, PRKDC, PRPF40B, PRPF8, PSMD13, PTCH1, PTEN, PTK2, PTPN11, PTPRD, QKI, RAD21, RAF1, RARA, RB1, RBL2, RECQL4, REL, RET, RFWD2, RHEB, RHPN2, ROS1, RPL26, RUNX1, SBDS, SDHA, SDHAF2, SDHB, SDHC, SDHD, SETBP1, SETD2, SF1, SF3B1, SH2B3, SLITRK6, SMAD2, SMAD4, SMARCA4, SMARCB1, SMCIA, SMC3, SMO, SOCS1, SOX2, SOX9, SQSTM1, SRC, SRSF2, STAG1, STAG2, STAT3, STAT6, STK11, SUFU, SUZ12, SYK, TCF3, TCF7L1, TCF7L2, TERC, TERT, TET2, TLR4, TNFAIP3, TP53, TSC1, TSC2, U2AF1, VHL, WRN, WT1, XPA, XPC, XPO1, ZNF217, ZNF708, ZRSR2.

Intronic regions are tiled on specific introns of ABL1, AKT3, ALK, BCL2, BCL6, BRAF, CIITA, EGFR, ERG, ETV1, EWSR1, FGFR1, FGFR2, FGFR3, FUS, IGH, IGL, JAK2, MLL, MYC, NPM1, NTRK1, PAX5, PDGFRA, PDGFRB, PPARG, RAF1, RARA, RET, ROS1, SS18, TRA, TRB, TRG, TMPRSS2.

ATAC-Sequencing and Analysis

ATAC sequencing was performed on H69 and H69AR cells according to[34].

Briefly, 40-50,000 cells were sorted per biological replicate, which were then washed once in cold PBS and lysed in 50 µL cold lysis buffer (10 mM Tris-HCl, pH 7.4, 10 mM NaCl, 3 mM MgCl2, 0.1% IGEPAL CA-630). Lysed nuclei were incubated in Tn5 transposition reaction mix and purified using MinElute Reaction Cleanup kit (Qiagen). ATAC-seq fragments from one set of replicates for H69 and H69AR cells were size selected for fragments between 115 and 600 bp using Pippin Prep 2% Agarose Gel Cassettes and the Pippin Prep DNA Size Selection System (Sage Science). Post size-selection, ATAC libraries were amplified and Nextera sequencing primers ligated using Polymerase Chain Reaction (PCR). Finally, PCR primers were removed using Agencourt AMPure XP bead cleanup (Beckman Coulter/Agencourt) and library quality was verified using a Tapestation machine. High quality 'multiplexed' DNA libraries were sequenced on the Illumina HiSeq2000.

The ends of the paired-end fragments are used as cut sites and enriched peaks were called with MACS2 with following parameters (-nomodel-extsize 200-shift-100-g hs-B-no-lambda). For IGV visualization, shifted bedGraph were converted to wig files at 10 bp resolution and normalized to read counts by wigmath tool of JavaGenomic toolkit.

Genomic Analysis and SPARCS Gene Set Derivation

The H69 vs H69M expression microarray data analyzed in this study were obtained from the publicly available dataset GSE45120.

ChIP-seq data for STAT1 and IRF1 data on CD14+ monocytes were retrieved from GEO database (GSE43036). Replicates data for each ChIP were aggregated into a single wiggle file and visualized in IGV genome browser at the locus of TRIM22 gene[35].

Genomic coordinates of all 3'UTR from NCBI RefSeq transcripts were intersected with all repeat elements that are 50 bp or longer and have its family name containing a string 'ERV' from UCSC Repeat Masker. Those 5880 3'UTRs that overlap with any ERVs were collapsed to the gene level. Those 1,080 unique genes were further used to find overlaps with differentially expressed gene from an analysis comparing H69M vs H69. Of 452 significantly upregulated genes (adjP<1E-4 and logFC>2) in H69M, 22 genes were found overlapped. As only 86 genes were identified at the same threshold, the same number of genes (452) most significantly downregulated genes at logFC<1 were used to find overlaps with the genes containing ERV in its 3' UTR (25 genes).

Gene Set Enrichment Analysis

SPARCS signature was created by overlapping 3'UTR repeat elements from Ref Seq with genes upregulated in H69M when compared to parental H69[5]. The SPARCS gene set scores across CCLE (broadinstitute.org/CCLE) or TCGA (Pancan12)[17] were derived by using ssGSEA algorithm[36]. These scores were used to identify top associated features from the matching datasets containing profiles of mRNA, pathways (MsigDB), and mutations/copy number variation data (broadinstitute.org/CCLE). To quantify the degree of association, an information-theoretic measure Information Coefficient (IC)[18] was used and an empirical permutation test for statistical significance calculations.

Statistical Analyses

All graphs depict mean±s.d. unless otherwise indicated. Tests for differences between two groups were performed using two-tailed unpaired Student's t-test or Mann-Whitney's two-tailed test, as specified in the figure legends. Two-way ANOVA with a Sidak post hoc test was performed to compare tumor growth between groups in xenograft studies. P values were considered significant if less than 0.05. Asterisks used to indicate significance correspond with: *p<0.05, p<0.01, *p<0.001. GraphPad Prism7 was used for statistical analysis of experiments, data processing and presentation.

REFERENCES

1 Hanahan, D. & Weinberg, R. A. Hallmarks of cancer: the next generation. Cell 144, 646-674, doi:10.1016/j.cell.2011.02.013 (2011).
2 Marusyk, A. et al. Non-cell-autonomous driving of tumour growth supports sub-clonal heterogeneity. Nature 514, 54-58, doi:10.1038/nature13556 (2014).
3 Junttila, M. R. & de Sauvage, F. J. Influence of tumour micro-environment heterogeneity on therapeutic response. Nature 501, 346-354, doi:10.1038/nature12626 (2013).
4 Tabassum, D. P. & Polyak, K. Tumorigenesis: it takes a village. Nat Rev Cancer 15, 473-483, doi:10.1038/nrc3971 (2015).
5 Canadas, I. et al. Targeting epithelial-to-mesenchymal transition with Met inhibitors reverts chemoresistance in small cell lung cancer. Clin Cancer Res 20, 938-950, doi:10.1158/1078-0432.CCR-13-1330 (2014).
6 Calbo, J. et al. A functional role for tumor cell heterogeneity in a mouse model of small cell lung cancer. Cancer Cell 19, 244-256, doi:10.1016/j.ccr.2010.12.021 (2011).
7 Konieczkowski, D. J. et al. A melanoma cell state distinction influences sensitivity to MAPK pathway inhibitors. Cancer Discov 4, 816-827, doi:10.1158/2159-8290.CD-13-0424 (2014).
8 Tirosh, I. et al. Dissecting the multicellular ecosystem of metastatic melanoma by single-cell RNA-seq. Science 352, 189-196, doi:10.1126/science.aad0501 (2016).
9 Crescenzo, R. et al. Convergent mutations and kinase fusions lead to oncogenic STAT3 activation in anaplastic large cell lymphoma. Cancer Cell 27, 516-532, doi:10.1016/j.ccell.2015.03.006 (2015).
10 Wu, X. et al. AXL kinase as a novel target for cancer therapy. Oncotarget 5, 9546-9563, doi:10.18632/oncotarget.2542 (2014).
11 Chiappinelli, K. B. et al. Inhibiting DNA Methylation Causes an Interferon Response in Cancer via dsRNA Including Endogenous Retroviruses. Cell 162, 974-986, doi:10.1016/j.cell.2015.07.011 (2015).
12 Roulois, D. et al. DNA-Demethylating Agents Target Colorectal Cancer Cells by Inducing Viral Mimicry by Endogenous Transcripts. Cell 162, 961-973, doi:10.1016/j.cell.2015.07.056 (2015).
13 Chuong, E. B., Elde, N. C. & Feschotte, C. Regulatory evolution of innate immunity through co-option of endogenous retroviruses. Science 351, 1083-1087, doi:10.1126/science.aad5497 (2016).
14 Gao, D. et al. Cyclic GMP-AMP synthase is an innate immune sensor of HIV and other retroviruses. Science 341, 903-906, doi:10.1126/science.1240933 (2013).
15 Poirier, J. T. et al. DNA methylation in small cell lung cancer defines distinct disease subtypes and correlates with high expression of EZH2. Oncogene 34, 5869-5878, doi:10.1038/onc.2015.38 (2015).
16 Henke, C. et al. Selective expression of sense and antisense transcripts of the sushi-ichi-related retrotransposon-derived family during mouse placentogenesis. Retrovirology 12, 9, doi:10.1186/s12977-015-0138-8 (2015).
17 Hoadley, K. A. et al. Multiplatform analysis of 12 cancer types reveals molecular classification within and across tissues of origin. Cell 158, 929-944, doi:10.1016/j.cell.2014.06.049 (2014).
18 Kim, J. W. et al. Characterizing genomic alterations in cancer by complementary functional associations. Nat Biotechnol 34, 539-546, doi:10.1038/nbt.3527 (2016).
19 Rhodes, D. A., Reith, W. & Trowsdale, J. Regulation of Immunity by Butyrophilins. Annu Rev Immunol 34, 151-172, doi:10.1146/annurev-immunol-041015-055435 (2016).
20 Bindea, G. et al. Spatiotemporal dynamics of intratumoral immune cells reveal the immune landscape in human cancer. Immunity 39, 782-795, doi:10.1016/j.immuni.2013.10.003 (2013).
21 Jenkins, R. W. et al. Ex Vivo Profiling of PD-1 Blockade Using Organotypic Tumor Spheroids. Cancer Discov, doi:10.1158/2159-8290.CD-17-0833 (2017).
22 Pan, D. et al. A major chromatin regulator determines resistance of tumor cells to T cell-mediated killing. Science, doi:10.1126/science.aao1710 (2018).
23 Miao, D. et al. Genomic correlates of response to immune checkpoint therapies in clear cell renal cell carcinoma. Science, doi:10.1126/science.aan5952 (2018).
24 Manguso, R. T. et al. In vivo CRISPR screening identifies Ptpn2 as a cancer immunotherapy target. Nature 547, 413-418, doi:10.1038/nature23270 (2017).

25 Peng, D. et al. Epigenetic silencing of TH1-type chemokines shapes tumour immunity and immunotherapy. *Nature* 527, 249-253, doi:10.1038/nature15520 (2015).
26 Christensen, C. L. et al. Targeting transcriptional addictions in small cell lung cancer with a covalent CDK7 inhibitor. *Cancer Cell* 26, 909-922, doi:10.1016/j.ccell.2014.10.019 (2014).
27 Aref, A. R. et al. Screening therapeutic EMT blocking agents in a three-dimensional microenvironment. *Integr Biol (Camb)* 5, 381-389, doi:10.1039/c2ib20209c (2013).
28 Perocchi, F., Xu, Z., Clauder-Munster, S. & Steinmetz, L. M. Antisense artifacts in transcriptome microarray experiments are resolved by actinomycin D. *Nucleic Acids Res* 35, e128, doi:10.1093/nar/gkm683 (2007).
29 Chen, J. et al. Over 20% of human transcripts might form sense-antisense pairs. *Nucleic Acids Res* 32, 4812-4820, doi:10.1093/nar/gkh818 (2004).
30 Doench, J. G. et al. Optimized sgRNA design to maximize activity and minimize off-target effects of CRISPR-Cas9. *Nat Biotechnol* 34, 184-191, doi:10.1038/nbt.3437 (2016).
31 Sanjana, N. E., Shalem, 0. & Zhang, F. Improved vectors and genome-wide libraries for CRISPR screening. *Nat Methods* 11, 783-784, doi:10.1038/nmeth.3047 (2014).
32 Shalem, O. et al. Genome-scale CRISPR-Cas9 knockout screening in human cells. *Science* 343, 84-87, doi: 10.1126/science.1247005 (2014).
33 Carey, C. D. et al. Topological analysis reveals a PD-L1-associated microenvironmental niche for Reed-Sternberg cells in Hodgkin lymphoma. *Blood* 130, 2420-2430, doi: 10.1182/blood-2017-03-770719 (2017).
34 Sen, D. R. et al. The epigenetic landscape of T cell exhaustion. *Science* 354, 1165-1169, doi:10.1126/science.aae0491 (2016).
35 Qiao, Y. et al. Synergistic activation of inflammatory cytokine genes by interferon-gamma-induced chromatin remodeling and toll-like receptor signaling. *Immunity* 39, 454-469, doi:10.1016/j.immuni.2013.08.009 (2013).
36 Barbie, D. A. et al. Systematic RNA interference reveals that oncogenic KRAS-driven cancers require TBK1. *Nature* 462, 108-112, doi:10.1038/nature08460 (2009).

Example 2: STING Levels

STING Levels Vary Widely in KRAS Mutant Lung Cancer and Correlate with LKB1 and DNMT1 Status KRAS mutant non-small cell lung cancer (NSCLC) is a heterogeneous disease, and co-mutation of the tumor suppressor genes p53 or LKB1 defines different subtypes. KRAS; p53 mutant (KP) or KRAS;LKB1 mutant (KL) NSCLC cells exhibit divergent gene expression profiles and sensitivity to immune therapies. For example, KL NSCLC showed significantly lower expression of immune checkpoint molecules such as PD-L1 compared with KP NSCLC, implying less efficacy to PD-L1 targeted therapy in KL NSCLC patients (2, 3)

Using the Cancer Cell Line Encyclopedia (CCLE) database (4), differentially expressed genes between KP and KL cell lines were first extracted. Of those genes, 48 genes were highly expressed in KP cell lines, and also annotated as immune-related genes based on Gene Ontology (GO) term. TMEM173/STING (hereafter STING) is a critical regulator of innate immune response to cytosolic double strand DNA, and one of the top-ranked genes in this list. It was next demonstrated that STING expression was higher in KP cell lines in both mRNA and protein levels (FIGS. 15A and 15B). Since KRAS/LKB1/p53 mutant cells also showed lower expression compared with KP cells (HCC44, H2122, H1355, H23), these data suggested that the dominant feature associated with STING expression was LKB1 as opposed to p53 mutation status (loss of LKB1=low STING levels).

Given these data, it was next examined whether LKB1 directly regulates STING expression in KRAS mutant lung cancer. Interestingly, LKB1 reconstitution clearly increased STING expression in specific KL cell lines such as H1944, H2122 and H1355 (FIG. 16A). On the other hand, other KL cell lines such as A549, A427 and HCC44 were insensitive to LKB1 reconstitution (FIG. 16A). Since LKB1 loss leads to hyperactive DNA methyltransferase (DNMT) activity (5), which could silence STING epigenetically, it was wondered whether baseline DNMT1 expression might modulate this relationship in KL cells. Indeed, KL cell lines that were insensitive to LKB1 reconstitution expressed higher levels of DNMT1 than the sensitive lines (FIG. 16B). Interestingly, LKB1 reconstitution in the presence of a DNMT inhibitor in A549 cells (KL DNMT high cell line) was able to restore STING expression (FIG. 16C). Together, these data reveal that (1) LKB1 directly up-regulates STING expression in KRAS mutant lung cancer cells and (2) STING gene can be silenced by DNA methylation, and that DNA hypomethylation of the STING gene locus is required for LKB1 to regulate STING expression.

Figure 17A:
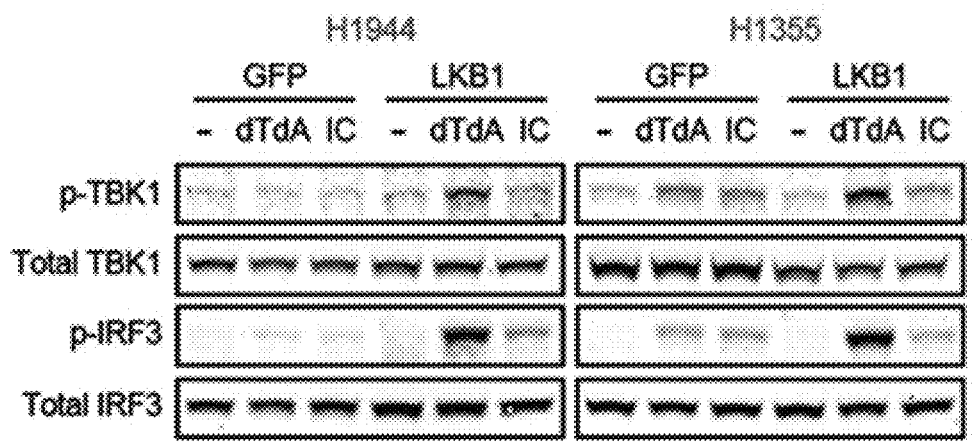
FIGS. 17A and 17B.
Figure 17B:
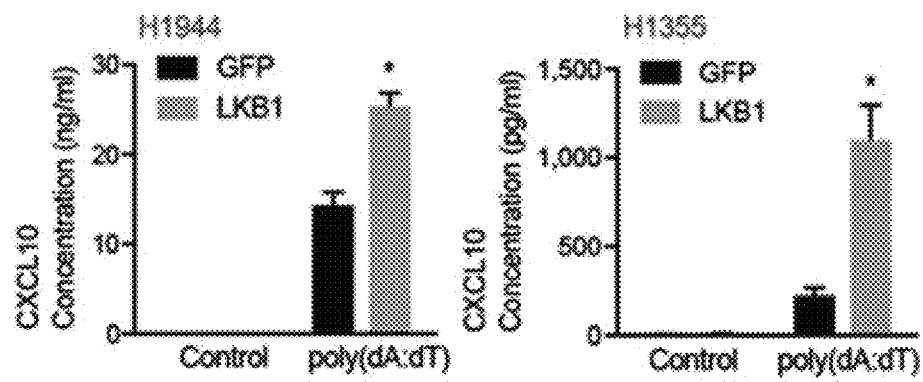

It was next examined whether increased STING expression following LKB1 reconstitution in KL cells altered their innate immune responsiveness to dsDNA. Transfection of a synthetic analogue of B-DNA, poly(dA:dT), strongly activated STING downstream pathway including TBK1 and IRF3 in LKB1 reconstituted KL cells compared with control cells (FIG. 17A). Poly(dA:dT) stimulation also promoted secretion of CXCL10, a key IRF3 target, specifically in LKB1 reconstituted cells (FIG. 17B). These results confirm that increased STING expression following LKB1 reconstitution contribute to enhanced innate immune response to cytosolic double-strand DNA.

Regulation of STING by EZH2 in Small Cell Lung Cancer

More broadly, epigenetic silencing, including regulation of specific histone modifications, is increasingly recognized in addition to DNA methylation as an important determinant in cancer immunology and immunotherapy response. For example, EZH2, which promotes histone H3K27 trimethylation and silencing of gene transcription, has been shown to play a key role in regulating Th1 chemokine expression and CD8(+) T cell infiltration in certain tumors (6), although the mechanism has been incompletely characterized. Interestingly, recent studies have implicated Endogenous Retrovirus (ERV) reactivation following DNA methyltransferase (DNMT) as a specific mechanism that may prime tumor immune responses through recognition of dsRNA and potentially dsDNA, suggesting a potentially synergistic approach to enhance immunogenicity in combination with PD-1 immune checkpoint blockade (7, 8).

Along these lines, by exploiting a human Small Cell Lung Cancer Model (SCLC) that exhibits tumor cell heterogeneity (H69 cells), an epigenetically regulated subclass of ERVs that promotes pathologic innate immune signaling, termed "Stimulated 3 Prime Antisense Retroviral Coding Sequences" (SPARCS) was recently identified (Canadas et al., Nature Medicine, in revision). These ERVs are poised to undergo positive feedback signal amplification due to their antisense localization in 3' UTRs of IFN stimulated genes, resulting dsRNA production, viral sensing, and positive feedback induction of their expression by IFN. Whereas neuroendocrine SCLC cells and other epithelial cancer cell lines silence these genes, mesenchymal subclones with high AXL/MET expression and low EZH2 levels are particularly susceptible to triggering SPARCS expression when exposed to IFNγ. Furthermore, it was directly demonstrated that these ERVs are silenced by EZH2, since treatment with an EZH2 inhibitor (GSK126) induced their reactivation in parental neuroendocrine H69 cells.

Figure 18:
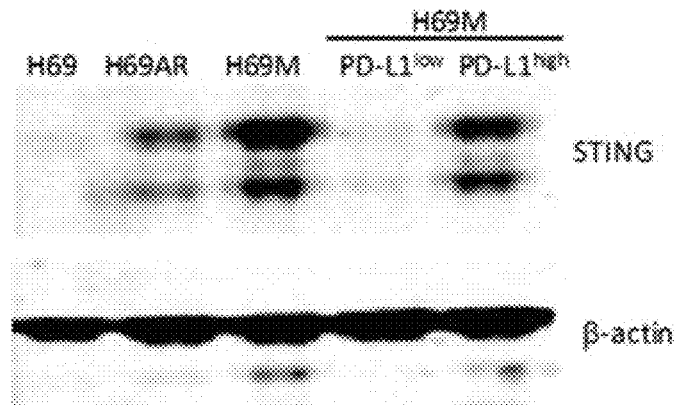
FIG. 18 shows increased STING expression in SCLC mesenchymal subclones. Immunoblot of STING and β-actin levels in H69 (neuroendocrine) or H69AR and H69M (mesenchymal) subclones.
Figure 21:
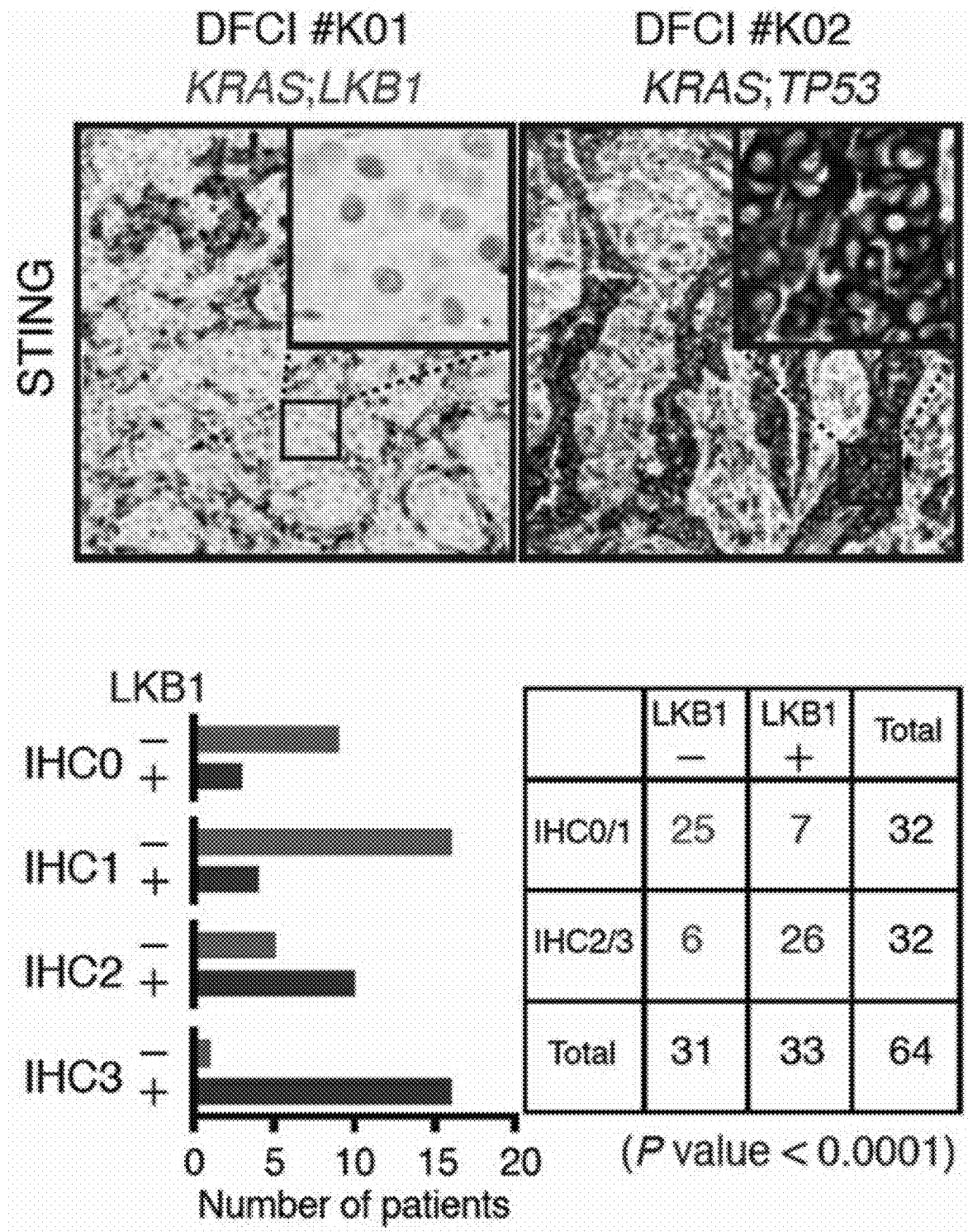
FIG. 21 shows representative STING IHC images of primary KL and KP non-small cell lung cancer (NSCLC) samples (upper panel). Insets highlight tumor cell STING expression. STING intensity in cancer cells was scored in a blinded manner (lower panel) on a scale of 0-3. IHC0: No staining, IHC1: low staining, IHC2: moderate staining, IHC3: high staining.

Given the above observations differences in STING levels between the parental neuroendocrine cell line H69 and the derivative drug-resistant subclones H69M and H69AR were also examined. Interestingly it was found that, in contrast to H69 cells, the resistant subclones expressed high levels of STING, as well as the H69M-PD-L1 high subpopulation (FIG. 18). Using ATAC seq and H3K27Ac ChIP seq the development of peaks in the 5' promoter region of TMEM173 as well as 3' enhancer in these tumor cell subclones relative to the parental 1169 cell line was further confirmed.

Variability of STING Expression Across Human Cancer Types

To determine the broader relevance of STING expression in cancer, as well as specific features linked to the SPARCS$^{high}$ state, STING expression across SPARCS$^{high}$ and SPARCS$^{low}$ cell lines was explored using the Cancer Cell Line Encyclopedia (CCLE) database. Interestingly, a robust and significant association of SPARCS$^{high}$ cell lines with high levels of STING was observed when compared with SPARCS$^{low}$ cell lines (FIG. 20A). 16 cell lines with high, intermediate, or low SPARCS signature expression were therefore selected and STING protein levels were determined. Of note, SPARCS$^{high}$ cells tightly correlated with particularly high protein expression of STING compared with a total lack of expression of this protein in SPARCS$^{low}$ cells (FIG. 20B). The only exception among the SPARC$^{high}$ cell lines that failed to express STING was HCC44, one of the KL cell lines lacking LKB1 and with high DNMT expression (FIG. 16).

Finally, it was observed that within this larger panel of cell lines, triple negative breast cancer (TNBC) cells (MDA-MB-231, HCC1143, MDA-MB-468) were STING positive, whereas estrogen receptor positive (ER+) cells (T47D, MDA-MB-453) were STING negative. Therefore a larger panel of breast cancer cell lines was characterized to determine if this trend held up. Indeed, whereas 5/6 TNBC cell expressed detectable levels of STING (1569, 1143, 70, 468, and 231), all 3 ER+ cell lines were STING negative (CAMA-1, T47D, and MCF7). These data suggest that TNBC in particular is a tumor type in which focused examination of STING levels in tumors and deployment of STING agonists+/−PD-1 blockade may have significant therapeutic impact. As above, it is also likely that epigenetic inhibitors (e.g. DNMT or EZH2) may convert STING$^{low}$ TNBC tumors or ER+ cell lines into STING$^{high}$ and prime them to respond to STING directed immunotherapy approaches.

REFERENCES

1. Barber G N. STING: infection, inflammation and cancer. *Nat Rev Immunol.* 2015; 15(12):760-70.
2. Skoulidis F, Byers L A, Diao L, Papadimitrakopoulou V A, Tong P, Izzo J, Behrens C, Kadara H, Parra E R, Canales J R, et al. Co-occurring Genomic Alterations Define Major Subsets of KRAS-Mutant Lung Adenocarcinoma with Distinct Biology, Immune Profiles, and Therapeutic Vulnerabilities. *Cancer Discov.* 2015; 5(8): 860-77.
3. Koyama S, Akbay E A, Li Y Y, Aref A R, Skoulidis F, Herter-Sprie G S, Buczkowski K A, Liu Y, Awad M M, Denning W L, et al. STK11/LKB1 deficiency promotes neutrophil recruitment and proinflammatory cytokine production to suppress T cell activity in the lung tumor microenvironment. *Cancer Res.* 2016.
4. Barretina J, Caponigro G, Stransky N, Venkatesan K, Margolin A A, Kim S, Wilson C J, Lehar J, Kryukov G V, Sonkin D, et al. The Cancer Cell Line Encyclopedia enables predictive modelling of anticancer drug sensitivity. *Nature.* 2012; 483(7391):603-7.
5. Kottakis F, Nicolay B N, Roumane A, Karnik R, Gu H, Nagle J M, Boukhali M, Hayward M C, Li Y Y, Chen T, et al. LKB1 loss links serine metabolism to DNA methylation and tumorigenesis. *Nature.* 2016; 539(7629):390-5.
6. Peng D, Kryczek I, Nagarsheth N, Zhao L, Wei S, Wang W, Sun Y, Zhao E, Vatan L, Szeliga W, et al. Epigenetic silencing of TH1-type chemokines shapes tumour immunity and immunotherapy. *Nature.* 2015; 527(7577):249-53.
7. Chiappinelli K B, Strissel P L, Desrichard A, Li H, Henke C, Akman B, Hein A, Rote N S, Cope L M, Snyder A, et al. Inhibiting DNA Methylation Causes an Interferon Response in Cancer via dsRNA Including Endogenous Retroviruses. *Cell.* 2015; 162(5):974-86.
8. Roulois D, Loo Yau H, Singhania R, Wang Y, Danesh A, Shen S Y, Han H, Liang G, Jones P A, Pugh T J, et al. DNA-Demethylating Agents Target Colorectal Cancer Cells by Inducing Viral Mimicry by Endogenous Transcripts. *Cell.* 2015; 162(5):961-73.

Example 3: STING Levels in Breast Cancer Subtypes

Figures 22A, 22B:
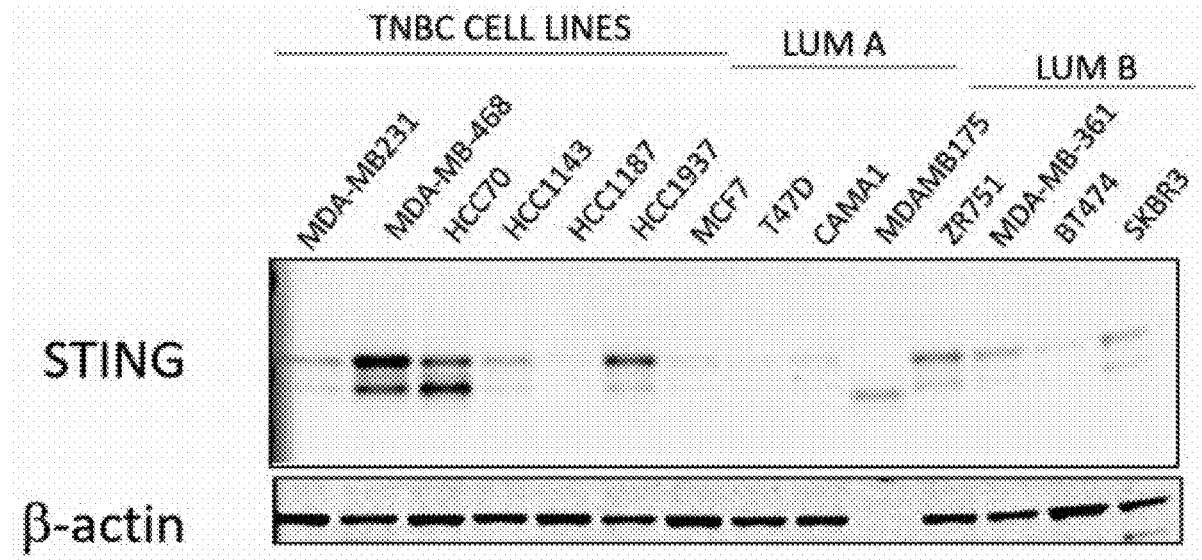
FIGS. 22A-22D show that triple negative breast cancer (TNBC) and luminal B breast cancer cell lines have elevated STING levels and TNBC cell lines are responsive to a STING agonist.
Figure 22C:
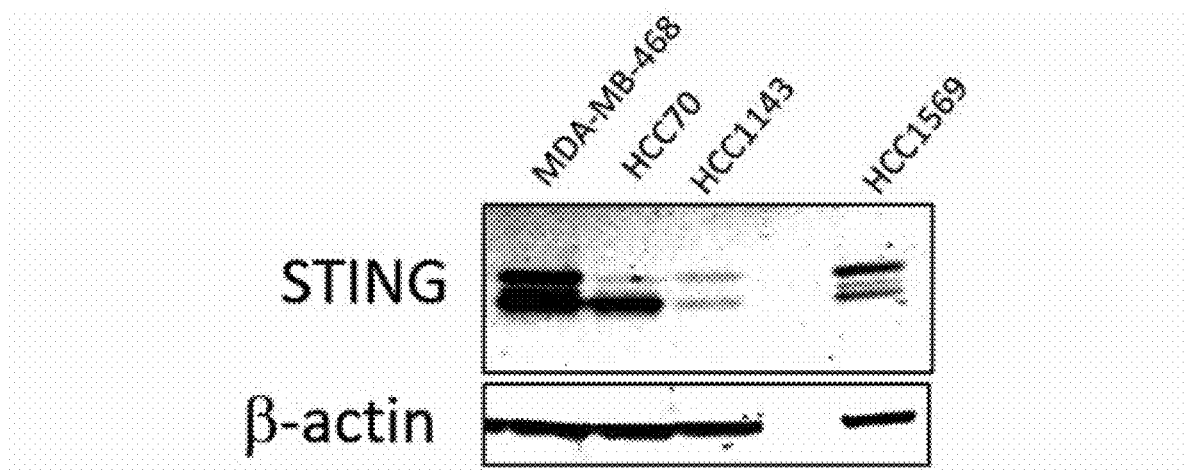

STING protein expression was measured in different breast cancer cell subtypes by western blot analysis on protein extracts from the breast cancer cell lines. Western results are shown in FIGS. 22A and 22C. STING protein levels are shown relative to β-actin control protein levels. Genotypes of the cell lines (ER+/−, PR+/−, and HER2+/−) are shown in FIG. 22B. The data presented herein demonstrates that STING levels are generally increased in TNBC (Triple Negative Breast Cancer) and luminal B cancer cell subtypes.

Figure 22D:
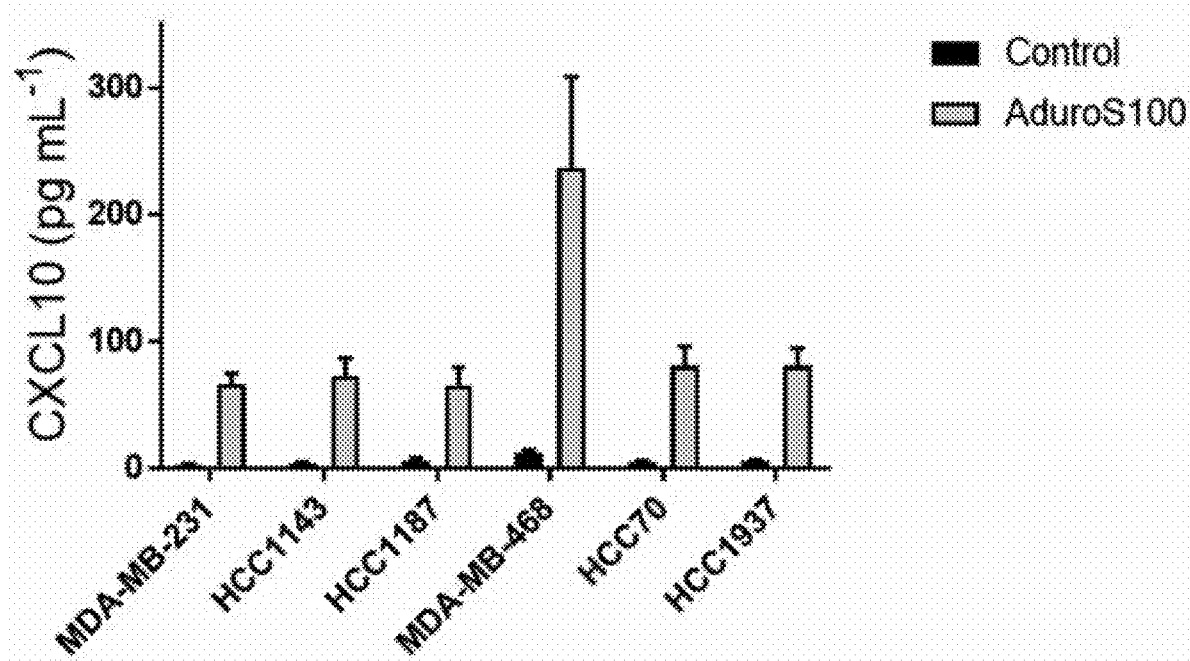

TNBC cell lines were also assayed for their responsiveness to the STING agonist AduroS100. Cells were treated with AduroS100 or a control and CXCL10 levels secreted into the supernatant were measured. As is shown in FIG. 22D, all TNBC cell lines showed elevated levels of the CXCL10 chemokine when treated with AduroS100 relative to a control, indicating that TNBC cells are responsive to treatment with a STING agonist, regardless of STING levels.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for treating cancer in a subject comprising:
   (i) obtaining a biological sample obtained from the subject having cancer, wherein the cancer is lung cancer;
   (ii) determining the level of Stimulator of IFN Genes (STING); and
   (iii) administering an effective amount of a therapy to the subject when the determined level of STING in the biological sample is below a reference value, thereby treating cancer in the subject, wherein the therapy is a DNA methyltransferase inhibitor and/or an EZH2 inhibitor, wherein the DNA methyltransferase inhibitor and/or EZH2 inhibitor is GSK126, azacitidine, or decitabine.

2. The method of claim 1, wherein the biological sample is a biopsy sample.

3. The method of claim 1, wherein the level of STING is the level of STING mRNA.

4. The method of claim 1, wherein the level of STING is the level of STING protein.

5. The method of claim 1, wherein the cancer is a non-small cell lung cancer (NSCLC).

6. The method of claim 1, wherein the reference value is the level of STING calculated from a control.

7. The method of claim 6, wherein the level of STING is 50% or more below the reference value of STING calculated from the control.

8. The method of claim 7, wherein the level of STING is determined in the same tissue type as a the biological sample from a normal subject.

9. The method of claim 6, wherein the level of STING is 5% or more below the reference value of STING calculated from the control.

10. A method for increasing STING expression in lung cancer cells in a subject comprising:
    (i) obtaining a biological sample obtained from the subject;
    (ii) determining the level of Stimulator of IFN Genes (STING); and
    (iii) administering an effective amount of a DNA methyltransferase inhibitor and/or an EZH2 inhibitor to the subject when the determined level of STING in the biological sample is below a reference value, thereby increasing STING expression in the lung cancer cells, wherein the DNA methyltransferase inhibitor and/or EZH2 inhibitor is GSK126, azacitidine, or decitabine.

11. The method of claim 10, wherein the biological sample is a biopsy sample.

12. The method of claim 10, wherein the level of STING is the level of STING mRNA.

13. The method of claim 10, wherein the level of STING is the level of STING protein.

14. The method of claim 10, wherein the cancer is a non-small cell lung cancer (NSCLC).

15. The method of claim 10, wherein the reference value is the level of STING calculated from a control.

16. The method of claim 15, wherein the level of STING is 50% or more below the reference value of STING calculated from the control.

17. The method of claim 15, wherein the level of STING is 5% or more below the reference value of STING calculated from the control.

\* \* \* \* \*

SEQUENCE LISTING

<160> NUMBER OF SEQ ID NOS: 110

<210> SEQ ID NO 1
<211> LENGTH: 379
<212> TYPE: PRT
<213> ORGANISM: Artificial Sequence
<220> FEATURE:
<223> OTHER INFORMATION: Synthetic polypeptide

<400> SEQUENCE: 1

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
                20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
            115                 120                 125

Ala Leu Asn Ile Leu Leu Gly Leu Lys Gly Leu Ala Pro Ala Glu Ile
            130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
            195                 200                 205

Pro Asp Asn Leu Ser Met Ala Asp Pro Asn Ile Arg Phe Leu Asp Lys
            210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
            275                 280                 285

Lys Leu Phe Cys Arg Thr Leu Glu Asp Ile Leu Ala Asp Ala Pro Glu
            290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
            355                 360                 365

Glu Lys Pro Leu Pro Leu Arg Thr Asp Phe Ser
            370                 375

<210> SEQ ID NO 2
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 2
cagattggct acccaactgt t                                             21

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
tatggtggtg ccgactacaa                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
ccctgcagag gctgataaag                                               20

<210> SEQ ID NO 5
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 5
tcggtaactg acttgaatgt cca                                           23

<210> SEQ ID NO 6
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 6
atgaccaaca agtgtctcct cc                                            22

<210> SEQ ID NO 7
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 7
gcttgggatg agaccctcct a                                             21

<210> SEQ ID NO 8
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 8
gtggcattca aggagtacct c                                             21

<210> SEQ ID NO 9
<211> LENGTH: 24
<212> TYPE: DNA
<213> ORGANISM: Artificial Sequence

```
<220> FEATURE:
<223> OTHER INFORMATION: Synthetic polynucleotide

<400> SEQUENCE: 9
attacaacac tgccaagggc gtgt                                              24

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10
cgagagctac acgttcacgg                                                   20

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11
gacgccatca acaccgagtt                                                   20

<210> SEQ ID NO 12
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 12
ctgccgcttt gcaggtgta                                                    19

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
ccccagtcac ctgctgttat                                                   20

<210> SEQ ID NO 14
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 14
ggaaggtgta atccgtctcc ac                                                22

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 15
tgcttgtcca gatgacttcg                                                   20
```

```
<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 16
gccaggttat ccagcacatt                                           20

<210> SEQ ID NO 17
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 17
tcgcttccct gttttagctg c                                         21

<210> SEQ ID NO 18
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 18
ggaatccaag caagttgtag ctc                                       23

<210> SEQ ID NO 19
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 19
cccaccccct gtatcacac                                            19

<210> SEQ ID NO 20
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 20
tgatggcctt cgattctgga tt                                        22

<210> SEQ ID NO 21
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 21
ggagcacctc catgacccag tgca                                      24

<210> SEQ ID NO 22
<211> LENGTH: 21
<212> TYPE: DNA
<213> ORGANISM: Artificial Sequence
<220> FEATURE:
<223> OTHER INFORMATION: Synthetic polynucleotide
```

```
<400> SEQUENCE: 22
gggtgtcgag ggaaaaatag g                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 23
ctttgtcgtt ggttagctgg t                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 24
cattgtgggc aaggtgctat t                                              21

<210> SEQ ID NO 25
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 25
tggaatcctg aacccacttc                                                20

<210> SEQ ID NO 26
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 26
gaattcagtg ccactaagca gac                                            23

<210> SEQ ID NO 27
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 27
ggagcttcct gattggcaga                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 28
gcagggagga ttgaaagaaa                                                20

<210> SEQ ID NO 29
```

-continued

```
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 29
aggaagcagc aaatggctaa                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30
agcagatagc ccagacctca                                              20

<210> SEQ ID NO 31
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 31
atatccctca ccacgatcct aata                                         24

<210> SEQ ID NO 32
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 32
tcttggagtc ctcactcaaa ctc                                          23

<210> SEQ ID NO 33
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 33
caggaaacta actttcagcc aga                                          23

<210> SEQ ID NO 34
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 34
atatcctgcc tggatggggt                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 35
```
tgcctgtctc caaacacagt                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 36
tattgccgta ctgtgggctg                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 37
tgtgtcctcc cccttctctt                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 38
ccctaaagag gcaggacacc                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 39
cctcctgagc cagagtaggt                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 40
ggagaagctg atggtgcaga                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 41
tctcacaatc ctggaggctg                                               20

<210> SEQ ID NO 42
<211> LENGTH: 18
<212> TYPE: DNA

```
<213> ORGANISM: Artificial Sequence
<220> FEATURE:
<223> OTHER INFORMATION: Synthetic polynucleotide

<400> SEQUENCE: 42
caccctgctt ctcctgct                                                   18

<210> SEQ ID NO 43
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 43
tgggctcttt gggtgatagt                                                 20

<210> SEQ ID NO 44
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 44
gctgttgcac acatgctctt                                                 20

<210> SEQ ID NO 45
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 45
cagatgaagc cctctctcag a                                               21

<210> SEQ ID NO 46
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 46
gaaggcacat aaccccaacc                                                 20

<210> SEQ ID NO 47
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 47
atgaatggga ttggtgggct                                                 20

<210> SEQ ID NO 48
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 48
taactgggtc atgagggtgg                                                 20
```

<210> SEQ ID NO 49
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 49
aactctgggc ttccgtttcc                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 50
gttaagcttc cctcctcccc                                              20

<210> SEQ ID NO 51
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 51
ttccctctgc cctgatctaa                                              20

<210> SEQ ID NO 52
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 52
ctccaaggaa ttgactcagc a                                            21

<210> SEQ ID NO 53
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 53
caccctgctt ctcctgct                                                18

<210> SEQ ID NO 54
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 54
acctcctctc cactcttcct                                              20

<210> SEQ ID NO 55
<211> LENGTH: 23
<212> TYPE: DNA
<213> ORGANISM: Artificial Sequence
<220> FEATURE:

```
<223> OTHER INFORMATION: Synthetic polynucleotide

<400> SEQUENCE: 55
agctgttaca acatagtagc cac                                              23

<210> SEQ ID NO 56
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 56
ctgctctgtt ctcgacagct t                                                21

<210> SEQ ID NO 57
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 57
aatgcaagtg gtactttgc ca                                                22

<210> SEQ ID NO 58
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 58
tcggtatatc caagacatga tcc                                              23

<210> SEQ ID NO 59
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 59
atgtagggtg gcaagcactg                                                  20

<210> SEQ ID NO 60
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 60
tggtgctgac ttcaagaacg                                                  20

<210> SEQ ID NO 61
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 61
caaattaagg agcgggtcaa                                                  20
```

```
<210> SEQ ID NO 62
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 62
caaagctctg cccactaagg                                               20

<210> SEQ ID NO 63
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 63
ccctctgtag tgcaaagact gata                                          24

<210> SEQ ID NO 64
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 64
actgctgcaa ctacccttaa aca                                           23

<210> SEQ ID NO 65
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 65
taaagagggc atggagtaat tga                                           23

<210> SEQ ID NO 66
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 66
gagcttctta gtcctcctgt gt                                            22

<210> SEQ ID NO 67
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 67
tacgggctga gcttgagttg                                               20

<210> SEQ ID NO 68
<211> LENGTH: 20
<212> TYPE: DNA
<213> ORGANISM: Artificial Sequence
<220> FEATURE:
<223> OTHER INFORMATION: Synthetic polynucleotide
```

```
<400> SEQUENCE: 68
tggaacagag cccttccttg                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 69
gcctgtggat gtgcccttat                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 70
tcaagcaatc gtcaaccaga                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 71
accagtctgg ctgtttctgt                                              20

<210> SEQ ID NO 72
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 72
accaaccttc ccaagcaaga                                              20

<210> SEQ ID NO 73
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 73
gaccaagaag caagccctca                                              20

<210> SEQ ID NO 74
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 74
aatgcctgag actgggtgat                                              20

<210> SEQ ID NO 75
<211> LENGTH: 20
```

```
<212> TYPE: DNA
<213> ORGANISM: Artificial Sequence
<220> FEATURE:
<223> OTHER INFORMATION: Synthetic polynucleotide

<400> SEQUENCE: 75
ttgcagatgg ctaccttcct                                              20

<210> SEQ ID NO 76
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 76
gatgtggaag tctgggaagc                                              20

<210> SEQ ID NO 77
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 77
ccttcctctc tcctggtgtc                                              20

<210> SEQ ID NO 78
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 78
gggtccagct gtgttttctg                                              20

<210> SEQ ID NO 79
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 79
ttctagagcc tgggaagtcc                                              20

<210> SEQ ID NO 80
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 80
catttgctcg gattctgggg                                              20

<210> SEQ ID NO 81
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 81
```
aaagcatgcc tctttcctgc                                              20

<210> SEQ ID NO 82
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 82
agtgaaaagg ctcagaccga                                              20

<210> SEQ ID NO 83
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 83
gtcagtggct tacaacaacg t                                            21

<210> SEQ ID NO 84
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 84
tctacctccc tgctgagtct                                              20

<210> SEQ ID NO 85
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 85
aatgcctgag actgggtgat                                              20

<210> SEQ ID NO 86
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 86
agttctgcag gctctacagg                                              20

<210> SEQ ID NO 87
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 87
ggacagggac tgcaaatctg at                                           22

<210> SEQ ID NO 88
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 88
cagctcccct tgaattgttt ttg                                              23

<210> SEQ ID NO 89
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 89
aagcccgatg aatgtcttcc t                                                21

<210> SEQ ID NO 90
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 90
gcacacgacg acagacgacg caccaaacat gatctgggtc atcttctc                   48

<210> SEQ ID NO 91
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 91
gcacacgacg acagacgacg cacgctcgtc gtcgacaacg gctccggca                  49

<210> SEQ ID NO 92
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 92
gcacacgacg acagacgacg cactggaaca gagcccttcc ttg                        43

<210> SEQ ID NO 93
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 93
gcacacgacg acagacgacg cactattgcc gtactgtggg ctg                        43

<210> SEQ ID NO 94
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 94
gcacacgacg acagacgacg cacgatgtgg aagtctggga agc                        43

<210> SEQ ID NO 95
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 95
gcacacgacg acagacgacg cacgctgttg cacacatgct ctt                43

<210> SEQ ID NO 96
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 96
gcacacgacg acagacgacg cacttgcaga tggctacctt cct                43

<210> SEQ ID NO 97
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 97
gcacacgacg acagacgacg cactgggctc tttgggtgat agt                43

<210> SEQ ID NO 98
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 98
gctcgtcgtc gacaacggct ccggca                                   26

<210> SEQ ID NO 99
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 99
caaacatgat ctgggtcatc ttctc                                    25

<210> SEQ ID NO 100
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 100
tattgccgta ctgtgggctg                                          20

<210> SEQ ID NO 101
<211> LENGTH: 20
<212> TYPE: DNA
<213> ORGANISM: Artificial Sequence
<220> FEATURE:
<223> OTHER INFORMATION: Synthetic polynucleotide

```
<400> SEQUENCE: 101
tggaacagag cccttccttg                                        20

<210> SEQ ID NO 102
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 102
gctgttgcac acatgctctt                                        20

<210> SEQ ID NO 103
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 103
gatgtggaag tctgggaagc                                        20

<210> SEQ ID NO 104
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 104
tgggctcttt gggtgatagt                                        20

<210> SEQ ID NO 105
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 105
ttgcagatgg ctaccttcct                                        20

<210> SEQ ID NO 106
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 106
gcacacgacg acagacgacg cac                                    23

<210> SEQ ID NO 107
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 107
agtacttcat tgcggcactg                                        20

<210> SEQ ID NO 108
```

```
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 108
ggtaccgggg cagctactgg                                                    20

<210> SEQ ID NO 109
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 109
atcgtttcgc ttaacggcg                                                     19

<210> SEQ ID NO 110
<211> LENGTH: 166
<212> TYPE: PRT
<213> ORGANISM: Artificial Sequence
<220> FEATURE:
<223> OTHER INFORMATION: Synthetic polypeptide

<400> SEQUENCE: 110

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165
```